(12) United States Patent
Kanstrup et al.

(10) Patent No.: US 7,235,538 B2
(45) Date of Patent: Jun. 26, 2007

(54) HETEROCYCLIC COMPOUNDS, WHICH ARE INHIBITORS OF THE ENZYME DPP-IV

(75) Inventors: Anders Bendtz Kanstrup, Espergaerde (DK); Lise Brown Christiansen, Lyngby (DK); Jane Marie Lundbeck, Glostrup (DK); Christian K. Sams, Frederiksberg (DK); Marit Kristiansen, Soborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/621,302

(22) Filed: Jul. 17, 2003

(65) Prior Publication Data

US 2004/0034014 A1 Feb. 19, 2004

Related U.S. Application Data

(63) Continuation of application No. 09/935,149, filed on Aug. 22, 2001, now abandoned, which is a continuation of application No. PCT/DK01/00467, filed on Jul. 4, 2001.

(60) Provisional application No. 60/223,240, filed on Aug. 4, 2000.

(30) Foreign Application Priority Data

Jul. 4, 2000 (DK) ............................... 2000 01040

(51) Int. Cl.
*A61K 31/522* (2006.01)
*A61K 3/10* (2006.01)
*A61K 3/04* (2006.01)
*C07D 473/08* (2006.01)
*C07D 473/06* (2006.01)

(52) U.S. Cl. .................. 514/81; 514/234.2; 514/218; 514/212.02; 514/263.2; 514/263.22; 540/575; 544/244; 544/118; 544/61; 544/269; 544/271; 544/272; 544/231

(58) Field of Classification Search ............... 514/81, 514/234.2, 218, 212.02, 263.2, 263.22; 544/271, 544/231, 269, 272, 61, 118, 244; 540/575
See application file for complete search history.

(56) References Cited

U.S. PATENT DOCUMENTS

| 3,896,119 A | | 7/1975 | Klingler |
| 4,636,229 A | * | 1/1987 | Itoh et al. ..................... 96/14 |
| 4,719,245 A | * | 1/1988 | Regelman .................... 521/128 |
| 5,461,059 A | * | 10/1995 | Bonnet et al. ............. 514/252.18 |
| 6,124,305 A | | 9/2000 | Villhauer ..................... 514/272 |
| 6,806,270 B2 | * | 10/2004 | Biaggioni et al. ........ 514/234.2 |
| 6,815,446 B1 | * | 11/2004 | Biaggioni et al. ........ 514/263.2 |
| 6,825,349 B2 | * | 11/2004 | Kalla et al. ................ 544/267 |
| 7,074,798 B2 | * | 7/2006 | Yoshikawa et al. ...... 514/263.2 |
| 2002/0198205 A1 | * | 12/2002 | Himmelsbach et al. .. 514/234.5 |
| 2003/0087904 A1 | * | 5/2003 | Biaggioni et al. ........ 514/234.5 |
| 2004/0023149 A1 | * | 2/2004 | Roussilhe et al. .......... 430/267 |
| 2004/0116328 A1 | * | 6/2004 | Yoshikawa et al. ............ 514/2 |
| 2004/0170586 A1 | * | 9/2004 | Ferrari et al. .................. 424/63 |

FOREIGN PATENT DOCUMENTS

| JP | 37-4895 | * | 6/1972 |
| WO | WO 91/07945 | | 6/1991 |
| WO | WO 92/05175 | | 4/1992 |
| WO | WO 98/19998 | | 5/1998 |
| WO | WO 99/38501 | | 8/1999 |
| WO | WO 00/34241 | | 6/2000 |

OTHER PUBLICATIONS

MSN Encarta® Dictionary entry for "aryl" <http://encarta.msn.com/encnet/features/dictionary/DictionaryResults.aspx?refid=1861587031> downloaded from the Internet Sep. 23, 2004.*
Romanenko, Farm. Zh. (Kiev) (5) 41-4, 1986 and translation.*
Holst et al., Diabetes, vol. 47, pp. 1663-1670 (1998).
Abstract of Kubota et al., Yakugaku Zasshi, vol. 89, pp. 441-445 (1969).
Abstract of Kleine et al., Arzneim.-Forsch., vol. 19, pp. 1854-1855 (1969).
Abstract of Romanenko et al., Farm. Zh. (Kiev), vol. 5, pp. 41-44 (1986).
Abstract of Samura et al., Khim.-Farm. Zh., vol. 20, pp. 52-55 (1986).

(Continued)

*Primary Examiner*—Mark L. Berch
(74) *Attorney, Agent, or Firm*—Rosemarie R. Wilk-Orescan; Richard W. Bork

(57) ABSTRACT

The present invention relates to therapeutically active and selective inhibitors of the enzyme DPP-IV, which are of formula I

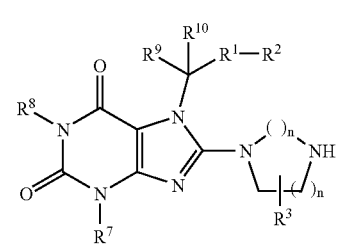

wherein each n is one or two independently and $R^1$, $R^2$, $R^3$, $R^6$, $R^7$, $R^9$, and $R^{10}$ are defined herein. The present invention also relates to pharmaceutical compositions comprising the compounds of formula I and the use of the compounds for treating diseases that are associated with proteins that are subject to inactivation by DPP-IV, such as type-2 diabetes and obesity.

10 Claims, No Drawings

OTHER PUBLICATIONS

Abstract of Gorczyca et al., Farmaco, Ed. Sci., vol. 29, pp. 802-810 (1974).

Abstract of Zimmer et al., Eur. J. Org. Chem., vol. 9, pp. 2419-2428 (1999).

Abstract of Gutorov et al., Khim.-Farm. Zh., vol. 10, pp. 61-64 (1976).

Abstract of Cygankiewicz et al., Acta Pol. Pharm., vol. 34, pp. 607-612 (1977).

Abstract of Khaliullin et al., Bashk. Khim. Zh., vol. 4, pp. 59-62 (1997).

Abstract of Martinson et al., Mol. Pharmacol., vol. 31, pp. 247-252 (1987).

Abstract of Skul'skaya et al., Farm. Zh. (Kiev), vol. 4, pp. 34-39 (1989).

Abstract of Mazur et al., Farm. Zh. (Kiev), vol. 3, pp. 82-84 (1996).

Abstract of Gorczya et al., Acta Pol. Pharm., vol. 39, pp. 315-321 (1982).

* cited by examiner

HETEROCYCLIC COMPOUNDS, WHICH ARE INHIBITORS OF THE ENZYME DPP-IV

CROSS-REFERENCE TO RELATED APPLICATIONS

This application is a continuation of Ser. No. 09/935,149, filed Aug. 22, 2001 now abandoned, which is a continuation of PCT application PCT/DK01/00467 filed Jul. 4, 2001, and claims the benefit of U.S. provisional application Ser. No. 60/223,240, filed Aug. 4, 2000 and of Danish application no. PA 2000 01040 filed Jul. 4, 2000, the contents of each of which are hereby incorporated by reference.

FIELD OF INVENTION

The present invention relates to therapeutically active and selective inhibitors of the enzyme DPP-IV, pharmaceutical compositions comprising the compounds and the use of such compounds for and the manufacture of medicaments for treating diseases that are associated with proteins which are subject to inactivation by DPP-IV, such as type 2 diabetes and obesity, as well as methods for treating diseases that are associated with proteins which are subject to inactivation by DPP-IV, such as type 2 diabetes and obesity.

BACKGROUND OF THE INVENTION

Dipeptidyl peptidase-IV (DPP-IV), a serine protease belonging to the group of post-proline/alanine cleaving amino-dipeptidases, specifically removes the two N-terminal amino acids from proteins having proline or alanine in position 2. Although the physiological role of DPP-IV has not been completely established, it is believed to play an important role in neuropeptide metabolism, T-cell activation, gastric ulceration, functional dyspepsia, obesity, appetite regulation, impaired fasting glucose (IFG) and diabetes.

DPP-IV has been implicated in the control of glucose metabolism because its substrates include the insulinotropic hormones Glucagon like peptide-1 (GLP-1) and Gastric inhibitory peptide (GIP). GLP-1 and GIP are active only in their intact forms; removal of their two N-terminal amino acids inactivates them.

In vivo administration of synthetic inhibitors of DPP-IV prevents N-terminal degradation of GLP-1 and GIP, resulting in higher plasma concentrations of these hormones, increased insulin secretion and, therefore, improved glucose tolerance. Therefore, such inhibitors have been proposed for the treatment of patients with Type 2 diabetes, a disease characterised by decreased glucose tolerance. (Hoist, J. J.; Deacon, C. F. Diabetes 47 (1998) 1663–70)

Diabetic dyslipidemia is characterized by multiple lipoprotein defects, including moderately high serum levels of cholesterol and triglycerides, small LDL particles, and low levels of HDL cholesterol. The results of recent clinical trials reveal beneficial effects of cholesterol-lowering therapy in diabetic and non-diabetic patients, thus supporting increased emphasis on treatment of diabetic dyslipidemia. The National Cholesterol Education Program's Adult Treatment Panel II advocated this need for intensive treatment of diabetic dyslipidemia.

Obesity is a well-known risk factor for the development of many very common diseases such as atherosclerosis, hypertension and diabetes. The incidence of obese people and thereby also these diseases is increasing throughout the entire industrialised world. Except for exercise, diet and food restriction no convincing pharmacological treatment for reducing body weight effectively and acceptably currently exist. However, due to its indirect but important effect as a risk factor in mortal and common diseases it will be important to find treatment for obesity or appetite regulation. Even mild obesity increases the risk for premature death, diabetes, hypertension, atherosclerosis, gallbladder disease and certain types of cancer. In the industrialised western world the prevalence of obesity has increased significantly in the past few decades. Because of the high prevalence of obesity and its health consequences, its prevention and treatment should be a high public health priority.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today. Several compounds have been shown to inhibit DPP-IV, but all of these have limitations in relation to the potency, stability, and pharmacodynamic properties.

Such compounds have e.g. been disclosed in WO 98/19998, WO 00/34241, U.S. Pat. No. 6,124,305 (Novartis AG) and WO 99/38501 (Trustees of Tufts University). The compounds of the present invention constitutes a completely novel class of DPP-IV inhibitors, structurally unrelated to any DPP-IV inhibitors known so far. They are furthermore potent and stable and thus offers a solution to the problems associated with the presently known DPP-IV inhibitors.

SUMMARY OF THE INVENTION

The present invention provides compounds of formula I

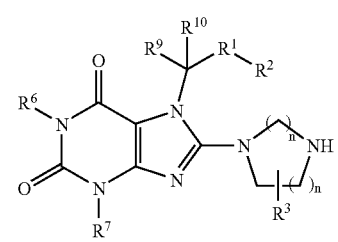

wherein
each n is one or two independently
R$^1$ is C=O; C=S; C$_1$–C$_2$ alkyl optionally substituted with one or more R$^4$ independently; C$_2$ alkenyl substituted with one or more R$^4$ independently; C$_2$ alkynyl; C$_3$–C$_7$ cycloalkyl optionally substituted with one or more R$^4$ independently; C$_3$–C$_7$ cycloheteroalkyl optionally substituted with one or more R$^4$ independently; aryl optionally substituted with one or more R$^4$ independently; aryl C$_1$–C$_3$ alkyl optionally substituted with one or more R$^4$ independently; heteroaryl optionally substituited with one or more R$^4$ independently; heteroaryl C$_1$–C$_3$ alkyl optionally substituted with one or more R$^4$ independently; perhalo C$_1$–C$_{10}$ alkyl; perhalo C$_1$–C$_{10}$ alkyloxy;
R$^2$ is H; C$_1$–C$_7$ alkyl optionally substituted with one or more R$^4$ independently; C$_2$–C$_7$ alkenyl optionally substituted with one or more R$^4$ independently; C$_2$–C$_7$ alkynyl optionally substituted with one or more R$^4$ independently; C$_3$–C$_7$ cycloalkyl optionally substituted with one or more R$^4$ independently; C$_3$–C$_7$ cycloheteroalkyl optionally substituted with one or more R$^4$ independently; aryl optionally substituted with one or more R⁴ independently; aryl C₁–C₃ alkyl optionally substituted with one or more R⁴ independently; heteroaryl C₁–C₃ alkyl optionally substituted with one or more R⁴ independently; heteroaryl optionally substituted with one or more R⁴ independently, —SH; —SR⁵; SO₂R⁵; SO₂R⁵; —CHO; —CH(OR⁵)₂; carboxy; —CO₂R⁴; NHCONNH₂; —NHCSNH₂; —NHCONH₂; —NHCOR⁴; —NHSO₂R⁵; —O—CO— (C₁–C₅) alkyl optionally substituted with one or more R⁴ independently; cyano; nitro; halogen; hydroxy; perhalo C₁–C₇ alkyl; perhalo C₁–C₇ alkyloxy; —SO₂NH₂; —SO₂NH(R⁵); —SO₂(R⁵)₂; —CONH₂; —CSNH₂; —CON₂H₃; —CONH(R⁵); —CON(R⁵)₂; C₁–C₁₀ alkyloxy optionally substituted with R⁴ independently; C₂–C₁₀ alkenyloxy optionally substituted with R⁴; C₂–C₁₀ alkynyloxy optionally substituted with R⁴ independently, aryloxy optionally substituted with R⁴ independently; heteroaryloxy optionally substituted with R⁴ independently;

R³ is H; C₁–C₁₀ alkyl optionally substituted with one or more R⁴ independently; C₂–C₁₀ alkenyl optionally substituted with one or more R⁴ independently; C₂–C₁₀ alkynyl optionally substituted with one or more R⁴ independently; C₃–C₇ cycloalkyl optionally substituted with one or more R⁴ independently; C₃–C₇ cycloheteroalkyl optionally substituted with one or more R⁴ independently; aryl optionally substituted with one or more R⁴ independently; aryl C₁–C₃ alkyl optionally substituted with one or more R⁴ independently; heteroaryl C₁–C₃ alkyl optionally substituted with one or more R⁴ independently; heteroaryl optionally substituted with one or more R⁴ independently; C₁–C₁₀ alkyl-NH(CH₂)₁₋₄NH-aryl optionally substituted with one or more R⁴ independently; C₁–C₁₀ alkyl-NH(CH₂)₁₋₄NH-heteroaryl optionally substituted with one or more R⁴ independently; C₁–C₁₀ alkyl-O(CH₂)₁₋₄NH-aryl optionally substituted with one or more R⁴ independently; C₁–C₁₀ alkyl-O(CH₂C₁₋₄NH-heteroaryl optionally substituted with one or more R⁴ independently; C₁–C₁₀ alkyl-O(CH₂)₁₋₄O-aryl optionally substituted with one or more R⁴ independently; C₁–C₁₀ alkyl-O(CH₂)₁₋₄O-heteroaryl optionally substituted with one or more R⁴ independently; C₁–C₁₀ alkyl-S(CH₂)₁₋₄NH-aryl optionally substituted with one or more R⁴ independently; C₁–C₁₀ alkyl-S(CH₂)₁₋₄NH-heteroaryl optionally substituted with one or more R⁴ independently; C₁–C₁₀ alkyl-S(CH₂)₁₋₄S-aryl optionally substituted with one or more R⁴ independently; C₁–C₁₀ alkyl-S(CH₂)₁₋₄S-heteroaryl optionally substituted with one or more R⁴ independently; C₁–C₁₀ alkyl-O—C₁–C₅alkyl optionally substituted with one or more R⁴; —NHCOR⁴; —NHSO₂R⁵; —O—CO—(C₁–C₅) alkyl optionally substituted with one or more R⁴ independently; —SH; —SR⁵; —SOR⁵; —SO₂R⁵; —CHO; —CH(OR⁵)₂; carboxy; cyano; nitro; halogen; hydroxy; —SO₂NH₂; —SO₂NH(R⁵); —SO₂N(R⁵)₂; —CONH₂; —CONH(R⁵); —CON(R⁵)₂; —CSNH₂; —CONHNH₂; —CO2R⁴; —NHCNHNH₂; —NHCSNH₂; —NHCONH₂;

R⁴ is C₁–C₁₀ alkyl optionally substituted with one or more R⁸ independently; C₂–C₁₀ alkenyl optionally substituted with one or more R⁸ independently; C₂–C₁₀ alkynyl optionally substituted with one or more R⁸ independently; C₃–C₇ cycloalkyl optionally substituted with one or more R⁸ independently; C₃–C₇ cycloheteroalkyl optionally substituted with one or more R⁸ independently; aryl optionally substituted with one or more R⁸ independently; heteroaryl optionally substituted with one or more R⁸ independently; amino; amino substituted with one or more C₁–C₁₀ alkyl optionally substituted with one or more R⁸; amino substituted with one or two aryl optionally substituted with one or more R⁸ independently; heteroaryl optionally substituted with one or more R⁸ independently; =O; =S; —CO—R5; —COOR5; —O—CO—(C₁–C₅) alkyl optionally substituted with one or more R⁸ independently; NH(CH₂)₁₋₄NH-aryl; NH(CH₂)₁₋₄NH-heteroaryl; —NHCOR⁵; —SOR⁵; SO₂R⁵; carboxy; cyano; N-hydroxyimino; nitro; halogen; hydroxy; perhalo C₁–C₁₀ alkyl; perhalo C₁–C₁₀ alkyloxy; —SH; —SR⁵; —SO₃H; —SO₃R⁵; —SO₂R⁵; —SO₂NH₂; —SO₂NH(R⁵); —SO₂N(R⁵)₂; —CONH₂; —CONH(R⁵); —CON(R⁵)₂; C₁–C₁₀ alkyloxy optionally substituted with one or more R⁸ independently; C₂–C₁₀ alkenyloxy optionally substituted with one or more R⁸ independently; C₂–C₁₀ alkynyloxy optionally substituted with one or more R⁸ independently; aryloxy optionally substituted with one or more R⁸ independently; heteroaryloxy optionally substituted with one or more R⁸ independently; and two R⁴ attached to the same carbon atom may form a spiroheterocyclic system, preferably hydantoin; thiohydantoin; oxazolidine-2,5-dione;

R⁵ is C₁–C₁₀ alkyl optionally substituted with one or more R⁸ independently; C₂–C₁₀ alkenyl optionally substituted with one or more R⁸ independently; C₂–C₁₀ alkynyl optionally substituted with one or more R⁸ independently; C₃–C₇ cycloalkyl optionally substituted with one or more R⁸ independently; C₃–C₇ cycloheteroalkyl optionally substituted with one or more R⁸ independently; aryl optionally substituted with one or more R⁸ independently; aryl. C₁–C₅ alkyl optionally substituted with one or more R⁸ independently; heteroaryl optionally substituted with one or more R⁸ independently; heteroaryl C₁–C₅ alkyl optionally substituted with one or more R⁸ independently;

R⁶ is H; C₁–C₁₀ alkyl optionally substituted with one or more R⁴ independently; C₂–C₁₀ alkenyl optionally substituted with one or more R⁴ independently; C₂–C₁₀ alkynyl optionally substituted with one or more R⁴ independently; C₃–C₇ cycloalkyl optionally substituted with one or more R⁴ independently; C₃–C₇ cycloheteroalkyl optionally substituted with one or more R⁴ independently; aryl optionally substituted with one or more R⁴ independently; heteroaryl optionally substituted with one or more R⁴ independently;

R⁷ is H; C₁–C₁₀ alkyl optionally substituted with one or more R⁴ independently; C₂–C₁₀ alkenyl optionally substituted with one or more R⁴ independently; C₂–C₁₀ alkynyl optionally substituted with one or more R⁴ independently; C₃–C₇ cycloalkyl optionally substituted with one or more R⁴ independently; C₃–C₇ cycloheteroalkyl optionally substituted with one or more R⁴ independently; aryl optionally substituted with one or more R⁴ independently; heteroaryl optionally substituted with one or more R⁴ independently;

R⁸ is H, amidoxime; nitro, tetrazole; pentafluorophenyl; —CH₂OH; —CHO; —C(OCH₃)₂; —COCH₃; —CF₃; —CCl₃; —OCF₃; —OCH₃; —CN; —CO₂H; —CO₂CH₃; —CONH₂; —CSNH₂; —CON₂H₃; —SO₃H; —SO₂NH₂; —SO₂NHCH₃; —SO₂N(CH₃)₂; —SO₂ (1-piperazinyl); —SO₂ (4-methylpiperazin-1-yl); —SO₂ (pyrrolidin-1-yl); —SO₂ (piperidin-1-yl); —SO₂ (morpholin-4-yl); N-hydroxyimino; —NH₂; —NHCH₃; —N(CH₃)₂; —NHCNHNH₂; —NHCNHNHCH₃; —NHCSNH₂; —NHCSNHCH₃; —NHCONH₂; —NHCONHCH₃; —NHCOCH₃; —NHSO₂CH₃; piperazinyl; morhpolin-4-yl; thiomorpholin-4-yl; pyrrolidin-1-yl; piperidin-1-yl; halogen; —OH;

—SH; —SCH₃; -aminoacetyl; —OPO₃H; —OPO₂OCH₃; —PO₃H₂; —PO(OCH₃)₂; PO(OH)(OCH₃);

$R^9$ is H; halogen; $C_1$–$C_{10}$ alkyl optionally substituted with one or more $R^4$ independently $R^{10}$ is H; halogen;

or, $R^9$ and $R^{10}$ may be connected to form a cyclopropyl ring;

or a salt thereof with a pharmaceutically acceptable acid or base;

with the exception of the following compounds:
1,3-dimethyl-7-(2-oxo-propyl)-8-piperazin-1-yl-3,7-dihydro-purine-2,6-dione,
1,3,1',3',7'-pentamethyl-8-piperazin-1-yl-3,7,3',7'-tetrahydro-7,8'-methanediyl-bis-purine-2,6-dione,
3,4,5-trimethoxy-benzoic acid 2-(1,3-dimethyl-2,6-dioxo-8-piperazin-1-yl-1,2,3,6-tetrahydro-purin-7-yl)-ethyl ester,
7-[2-Hydroxy-3-(4-methoxy-phenoxy)-propyl]-3-methyl-8-piperazin-1-yl-3,7-dihydro-purine-2,6-dione,
7-[2-hydroxy-2-(4-nitro-phenyl)-ethyl]-3-methyl-8-piperazin-1-yl-3,7,8,9-tetrahydro-purine-2,6-dione,
7-Benzyl-3-methyl-8-piperazin-1-yl-3,7-dihydro-purine-2,6-dione,
7-(4-Chloro-benzyl)-3-methyl-8-piperazin-1-yl-3,7-dihydro-purine-2,6-dione,
7-(2-Chloro-benzyl)-3-methyl-8-piperazin-1-yl-3,7-dihydro-purine-2,6-dione,
7-Ethyl-3-methyl-8-piperazin-1-yl-3,7-dihydro-purine-2,6-dione,
3-Methyl-8-piperazin-1-yl-1,7-dipropyl-3,7-dihydro-purine-2,6-dione,
3-Methyl-7-(3-methyl-butyl)-8-piperazin-1-yl-3,7-dihydro-purine-2,6-dione,
7-Butyl-3-methyl-8-piperazin-1-yl-3,7-dihydro-purine-2,6-dione,
3-Methyl-7-(3-phenyl-propyl)-8-piperazin-1-yl-3,7-dihydro-purine-2,6-dione,
7-But-2-enyl-3-methyl-8-piperazin-1-yl-3,7-dihydro-purine-2,6-dione,
7-(3-Chloro-but-2-enyl)-3-methyl-8-piperazin-1-yl-3,7-dihydro-purine-2,6-dione,
7-Heptyl-3-methyl-8-piperazin-1-yl-3,7-dihydro-purine-2,6-dione,
3-Methyl-7-(1-phenyl-ethyl)-8-piperazin-1-yl-3,7-dihydro-purine-2,6-dione,
3-Methyl-7-(3-methyl-benzyl)-8-piperazin 1-yl-3,7-dihydro-purine-2,6-dione,
3-Methyl-7-propyl-8-piperazin-1-yl-3,7-dihydro-purine-2,6-dione, and
3-Methyl-7-pentyl-8-piperazin-1-yl-3,7-dihydro-purine-2,6-dione.

Compounds of formula I may be used for the manufacture of a medicament for treating diseases that are associated with proteins which are subject to inactivation by DPP-IV.

In another aspect, the invention relates to the use of compounds of formula II wherein
$A^1$ is a carbon or nitrogen atom
The A-ring may be substituted with one or more $R^3$
$B^1$ and $B^2$ are carbon or nitrogen atoms, independently,
each $B^3$ is a carbon, nitrogen, oxygen, or sulfur atom, independently, each $n_1$, $n_2$, $n_3$, $n_4$ is one or two, independently,
$D^3$, $D^4$, and $D^5$ may be absent, in which case $D^1$ and $D^2$ may each be optionally substituted with one or two $R^2$, independently,
$D^1$, $D^2$, $D^3$, $D^4$, and each $D^5$ may independently be a carbon, nitrogen, oxygen, or a sulfur atom, or C=O, or C=S;
the bonds in the B-ring may be saturated or unsaturated, such that the B-ring may be a five-membered or a six-membered carbocyclic or heterocyclic ring, which may be fully saturated, or partially or fully unsaturated;
the bonds in the D-ring, when present, may be saturated or unsaturated, such that the D-ring may be a five-membered or a six-membered carbocyclic or heterocyclic ring, which may be fully saturated, or partially or fully unsaturated;
$R^1$ is C=O; C=C; $C_1$–$C_2$ alkyl optionally substituted with one or more $R^4$ independently; $C_2$ alkenyl substituted with one or more $R^4$ independently; $C_2$ alkynyl; $C_3$–$C_7$ cycloalkyl optionally substituted with one or more $R^4$ independently; $C_3$–$C_7$ cycloheteroalkyl optionally substituted with one or more $R^4$ independently; aryl optionally substituted with one or more $R^4$ independently; aryl $C_1$–$C_3$ alkyl optionally substituted with one or more $R^4$ independently; heteroaryl optionally substituted with one or more $R^4$ independently; heteroaryl $C_1$–$C_3$ alkyl optionally substituted with one or more $R^4$ independently; perhalo $C_1$–$C_{10}$ alkyl; perhalo $C_1$–$C_{10}$ alkyloxy;

Each $R^2$ is independently H; $C_1$–$C_7$ alkyl optionally substituted with one or more $R^4$ independently; $C_2$–$C_7$ alkenyl optionally substituted with one or more $R^4$ independently; $C_2$–$C_7$ alkynyl optionally substituted with one or more $R^4$ independently; $C_3$–$C_7$ cycloalkyl optionally substituted with one or more $R^4$ independently; $C_3$–$C_7$ cycloheteroalkyl optionally substituted with one or more $R^4$ independently; aryl optionally substituted with one or more $R^4$ independently; aryl $C_1$–$C_3$ alkyl optionally substituted with one or more $R^4$ independently; heteroaryl $C_1$–$C_3$ alkyl optionally substituted with one or more $R^4$ independently; heteroaryl optionally substituted with one or more $R^4$ independently, —SH; —SR⁵; SOR⁵; SO₂R⁵; —CHO; —CH(OR⁵)₂; carboxy; —CO₂R⁴; NHCONNH₂; —NHCSNH₂; —NHCONH₂; —NHCOR⁴; —NHSO₂R⁵; —O—CO—($C_1$–$C_5$) alkyl optionally substituted with one or more $R^4$ independently; cyano; nitro; halogen; hydroxy; —SO₂NH₂; —SO₂NH(R⁵); —SO₂(R⁵)₂; —CONH₂; —CSNH₂; —CON₂H₃; —CONH(R⁵);

—CON(R$^5$)$_2$; C$_1$–C$_{10}$ alkyloxy optionally substituted with R$^4$ independently; C$_2$–C$_{10}$ alkenyloxy optionally substituted with R$^4$; C$_2$–C$_{10}$ alkynyloxy optionally substituted with R$^4$ independently, aryloxy optionally substituted with R$^4$ independently; heteroaryloxy optionally substituted with R$^4$ independently;

R$^3$ is H; C$_1$–C$_{10}$ alkyl optionally substituted with one or more R$^4$ independently; C$_2$–C$_{10}$ alkenyl optionally substituted with one or more R$^4$ independently; C$_2$–C$_{10}$ alkynyl optionally substituted with one or more R$^4$ independently; C$_3$–C$_7$ cycloalkyl optionally substituted with one or more R$^4$ independently; C$_2$–C$_6$ cycloheteroalkyl optionally substituted with one or more R$^4$ independently; aryl optionally substituted with one or more R$^4$ independently; aryl C$_1$–C$_3$ alkyl optionally substituted with one or more R$^4$ independently; heteroaryl C$_1$–C$_3$ alkyl optionally substituted with one or more R$^4$ independently; heteroaryl optionally substituted with one or more R$^4$ independently; C$_1$–C$_{10}$alkyl-NH(CH$_2$)$_{1-4}$NH-aryl optionally substituted with one or more R$^4$ independently; C$_1$–C$_{10}$alkyl-NH(CH$_2$)$_{1-4}$NH-heteroaryl optionally substituted with one or more R$^4$ independently; C$_1$–C$_{10}$alkyl-O(CH$_2$)$_{1-4}$NH-aryl optionally substituted with one or more R$^4$ independently; C$_1$–C$_{10}$alkyl-O(CH$_2$)$_{1-4}$NH-heteroaryl optionally substituted with one or more R$^4$ independently; C$_1$–C$_{10}$alkyl-O(CH$_2$)$_{1-4}$O-aryl optionally substituted with one or more R$^4$ independently; C$_1$–C$_{10}$alkyl-O(CH$_2$)$_{1-4}$O-heteroaryl optionally substituted with one or more R$^4$ independently; C$_1$–C$_{10}$alkyl-S(CH$_2$)$_{1-4}$NH-aryl optionally substituted with one or more R$^4$ independently; C$_1$–C$_{10}$alkyl-S(CH$_2$)$_{1-4}$NH-heteroaryl optionally substituted with one or more R$^4$ independently; C$_1$–C$_{10}$ alkyl-S(CH$_2$)$_{1-4}$S-aryl optionally substituted with one or more R$^4$ independently; C$_1$–C$_{10}$alkyl-S(CH$_2$)$_{1-4}$S-heteroaryl optionally substituted with one or more R$^4$ independently; C$_1$–C$_{10}$alkyl-O—C$_1$–C$_5$alkyl optionally substituted with one or more R$^4$; —NHCOR$^4$; —NHSO$_2$R5; —O—CO—(C$_1$–C$_5$) alkyl optionally substituted with one or more R$^4$ independently; —SH; —SR$^5$; —SOR$^5$; —SO$_2$R$^5$; —CHO; —CH(OR$^5$)$_2$; carboxy; cyano; nitro; halogen; hydroxy; —SO$_2$NH$_2$; —SO$_2$NH(R$^5$); —SO$_2$N(R$^5$)$_2$; —CONH$_2$; —CONH(R$^5$); —CON(R$^5$)$_2$; —CSNH$_2$; —CONHNH$_2$; —CO2R$^4$; —NHCNHNH$_2$; —NHCSNH$_2$; —NHCONH$_2$; —NHCOR$^4$; —NHSO$_2$R$^5$;

R$^4$ is C$_1$–C$_{10}$ alkyl optionally substituted with one or more R$^8$ independently; C$_2$–C$_{10}$ alkenyl optionally substituted with one or more R$^8$ independently; C$_2$–C$_{10}$ alkynyl optionally substituted with one or more R$^8$ independently; C$_3$–C$_7$ cycloalkyl optionally substituted with one or more R$^8$ independently; C$_2$–C$_6$ cycloheteroalkyl optionally substituted with one or more R$^8$ independently; aryl optionally substituted with one or more R$^8$ independently; heteroaryl optionally substituted with one or more R$^8$ independently; amino; amino substituted with one or more C$_1$–C$_{10}$ alkyl optionally substituted with one or more R$^8$; amino substituted with one or two aryl optionally substituted with one or more R$^8$ independently; heteroaryl optionally substituted with one or more R$^8$ independently; =O; =S; —CO—R5; —COOR5; —O—CO—(C$_1$–C$_5$) alkyl optionally substituted with one or more R$^8$ independently; NH(CH$_2$)$_{1-4}$NH-aryl; NH(CH$_2$)$_{1-4}$NH-heteroaryl; —NHCOR$^5$; —SOR$^5$; SO$_2$R$^5$; carboxy; cyano; N-hydroxyimino; nitro; halogen; hydroxy; perhaloalkyl; perhaloalkyloxy; —SH; —SR$^5$; —SO$_3$H; —SO$_3$R$^5$; —SO$_2$R$^5$; —SO$_2$NH$_2$; —SO$_2$NH(R$^5$); —SO$_2$N(R$^5$)$_2$; —CONH$_2$; —CONH(R$^5$); —CON(R$^5$)$_2$; C$_1$–C$_{10}$ alkyloxy optionally substituted with one or more R$^8$ independently; C$_2$–C$_{10}$ alkenyloxy optionally substituted with one or more R$^8$ independently; C$_2$–C$_{10}$ alkynyloxy optionally substituted with one or more R$^8$ independently; aryloxy optionally substituted with one or more R$^8$ independently; heteroaryloxy optionally substituted with one or more R$^8$ independently; two R$^4$ attached to the same carbon may form a spiroheterocyclic system such as hydantoin; thiohydantoin; oxazolidine-2,5-dione;

R$^5$ is C$_1$–C$_{10}$ alkyl optionally substituted with one or more R$^8$ independently; C$_2$–C$_{10}$ alkenyl optionally substituted with one or more R$^8$ independently; C$_2$–C$_{10}$ alkynyl optionally substituted with one or more R$^8$ independently; C$_3$–C$_7$ cycloalkyl optionally substituted with one or more R$^8$ independently; C$_3$–C$_7$ cycloheteroalkyl optionally substituted with one or more R$^8$ independently; aryl optionally substituted with one or more R$^8$ independently; aryl C$_1$–C$_5$ alkyl optionally substituted with one or more R$^8$ independently; heteroaryl optionally substituted with one or more R$^8$ independently; heteroaryl C$_1$–C$_5$ alkyl optionally substituted with one or more R$^8$ independently;

R$^8$ is H, amidoxime; nitro, tetrazole; pentafluorophenyl; —CH$_2$OH; —CHO; —C(OCH$_3$)$_2$; —COCH$_3$; —CF$_3$; —CCl$_3$; —OCF$_3$; —OCH$_3$; —CN; —CO$_2$H; —CO$_2$CH$_3$; —CONH$_2$; —CSNH$_2$; —CON$_2$H$_3$; —SO$_3$H; —SO$_2$NH$_2$; —SO$_2$NHCH$_3$; —SO$_2$N(CH$_3$)$_2$; —SO$_2$ (1-piperazinyl); —SO$_2$ (-4-methylpiperazin-1-yl); —SO$_2$ (pyrrolidin-1-yl); —SO$_2$ (piperidin-1-yl); —SO$_2$ (morpholin-4-yl); N-hydroxyimino; —NH$_2$; —NHCH$_3$; —N(CH$_3$)$_2$; —NHCNHNH$_2$; —NHCNHNHCH$_3$; —NHCSNH$_2$; —NHCSNHCH$_3$; —NHCONH$_2$; —NHCONHCH$_3$; —NHCOCH$_3$; —NHSO$_2$CH$_3$; piperazinyl; morhpolin-4-yl; thiomorpholin-4-yl); pyrrolidin-1-yl; piperidin-1-yl; halogen; —OH; —SH; —SCH$_3$; -aminoacetyl; —OPO$_3$H; —OPO$_2$OCH$_3$; —PO$_3$H$_2$; —PO(OCH$_3$)$_2$; PO(OH) (OCH$_3$);

R$^9$ is H; halogen; C$_1$–C$_{10}$ alkyl optionally substituted with one or more R$^4$ independently R$^{10}$ is H; halogen;

R9 and R10 may be connected to form a cyclopropyl ring or a salt thereof with a pharmaceutically acceptable acid or base;

for the manufacture of a medicament for treating diseases that are associated with proteins which are subject to inactivation by DPP-IV.

DETAILED DESCRIPTION OF THE INVENTION

Definitions

The term "DPP-IV" as used herein is intended to mean Dipeptidyl peptidase IV (EC 3.4.14.5; DPP-IV), also known as CD26. DPP-IV cleaves a dipeptide from the N terminus of a polypeptide chain containing a proline or alanine residue in the penultimate position. The term "treatment" is defined as the management and care of a patient for the purpose of combating the disease, condition, or disorder and includes the administration of a compound of the present invention to prevent the onset of the symptoms or complications, or alleviating the symptoms or complications, or eliminating the disease, condition, or disorder. The term "beta cell degeneration" is intended to mean loss of beta cell function, beta cell dysfunction, and death of beta cells, such as necrosis or apoptosis of beta cells. The term "C$_1$–C$_{10}$alkyl" as used herein, alone or in combination, refers to a straight or branched; saturated hydrocarbon chain having from 1–10 carbon atoms such as but not limited to e.g. methyl, ethyl, n-propyl, isopropyl, n-butyl, sec. Butyl, isobutyl, tert. Butyl, n-pentyl, 2-methylbutyl, 3-methylbutyl, n-hexyl, 4-methylpentyl, neopentyl, 2,2-dimethylpropyl and the like.

The term "$C_2$–$C_{10}$-alkenyl" used herein, alone or in combination, refers to a straight or branched, unsaturated hydrocarbon chain having from 2–10 carbon atoms and at least one double bond such as but not limited to vinyl, 1-propenyl, allyl, isopropenyl, n-butenyl, n-pentenyl and n-hexenyl and the like.

The term "$C_2$–$C_{10}$ alkynyl" as used herein, alone or in combination, refers to an unsaturated hydrocarbon chain having from 2–10 carbon atoms and at least one triple bond such as but not limited to —C≡CH, —C≡CCH$_3$, —CH$_2$C≡CH, —CH$_2$—CH$_2$—C≡CH, —CH(CH$_3$)C≡CH and the like.

The term "$C_{1-10}$-alkoxy" as used herein, alone or in combination is intended to include those $C_{1-10}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy and hexoxy. Examples of branched alkoxy are isopropoxy, sec-butoxy, tert-butoxy, isopentoxy and isohexoxy. Example of cyclic alkoxy are cyclopropyloxy, cyclobutyloxy, cyclopentyloxy and cyclohexyloxy.

The term "$C_3$–$C_{10}$ cycloalkyl" as used herein refers to a radical of one or more saturated cyclic hydrocarbon having from 3–10 carbon atoms such as but not limited to cyclopropyl, cyclobutyl, cyclopentyl, cyclohexyl, adamantyl and the like.

The term "$C_5$–$C_{10}$ cycloalkenyl" as used herein refers to a radical of one or more cyclic hydrocarbon having at least one double bond having from 5–10 carbon atoms such as but not limited to cyclopentenyl, cyclohexenyl and the like The term "$C_2$–$C_6$ cycloheteroalkyl" as used herein refers to a radical of totally saturated heterocycle like a cyclic hydrocarbon containing one or more heteroatoms selected from nitrogen, oxygen and sulphur independently in the cycle such as pyrrolidine (1-pyrrolidine; 2-pyrrolidine; 3-pyrrolidine; 4-pyrrolidine; 5-pyrrolidine); pyrazolidine (1-pyrazolidine; 2-pyrazolidine; 3-pyrazolidine; 4-pyrazolidine; 5-pyrazolidine); imidazolidine (1-imidazolidine; 2-imidazolidine; 3-imidazolidine; 4-imidazolidine; 5-imidazolidine); thiazolidine (2-thiazolidine; 3-thiazolidine; 4-thiazolidine; 5-thiazolidine); piperidine (1-piperidine; 2-piperidine; 3-piperidine; 4-piperidine; 5-piperidine; 6-piperidine); piperazine (1-piperazine; 2-piperazine; 3-piperazine; 4-piperazine; 5-piperazine; 6-piperazine); morpholine (2-morpholine; 3-morpholine; 4-morpholine; 5-morpholine; 6-morpholine); thiomorpholine (2-thiomorpholine; 3-thiomorpholine; 4-thiomorpholine; 5-thiomorpholine; 6-thiomorpholine); 1,2-oxathiolane (3-(1,2-oxathiolane); 4-(1,2-oxathiolane); 5-(1,2-oxathiolane); 1,3-dioxolane (2-(1,3-dioxolane); 4-(1,3-dioxolane); 5-(1,3-dioxolane); tetrahydropyrane; (2-tetrahydropyrane; 3-tetrahydropyrane; 4-tetrahydropyrane; 5-tetrahydropyrane; 6-tetrahydropyrane); hexahydropyridazine (1-(hexahydropyridazine); 2-(hexahydropyridazine); 3-(hexahydropyridazine); 4-(hexahydropyridazine); 5-(hexahydropyridazine); 6-(hexahydropyridazine)).

The term "aryl" as used herein is defined as carbocyclic aromatic ring systems. Aryl is also intended to include the partially hydrogenated derivatives of the carbocyclic systems.

The term "heteroaryl" as used herein includes heterocyclic unsaturated ring systems containing one or more heteroatoms selected from nitrogen, oxygen and sulphur such as furyl, thienyl, pyrrolyl, heteroaryl is also intended to include the partially hydrogenated derivatives of the heterocyclic systems enumerated below.

The terms "aryl" and "heteroaryl" as used herein refers to an aryl which can be optionally substituted or a heteroaryl which can be optionally substituted and includes phenyl, biphenyl, indenyl, naphthyl (1-naphthyl, 2-naphthyl), N-hydroxytetrazolyl, N-hydroxyfriazolyl, N-hydroxyimidazolyl, anthracenyl (1-anthracenyl, 2-anthracenyl, 3-anthracenyl), thiophenyl (2-thienyl, 3-thienyl), futyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1 ,2,3-triazol- 1-yl, 1 ,2,3-triazol-2-yl 1 ,2,3-triazol-4-yl, 1 ,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3- pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]fiiranyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl).

The term halogen as used herein refers to fluorine, chlorine, bromine or iodine.

In the compounds of formula I, $R^2$ is preferably H; $C_2$–$C_7$ alkenyl optionally substituted with one or more $R^4$ independently; $C_2$–$C_7$ alkynyl optionally substituted with one or more $R^4$ independently; $C_3$–$C_7$ cycloalkyl optionally substituted with one or more $R^4$ independently; $C_3$–$C_7$ cycloheteroalkyl optionally substituted with one or more $R^4$ independently; aryl optionally substituted with one or more $R^4$ independently; aryl $C_1$–$C_3$ alkyl optionally substituted with one or more $R^4$ independently; heteroaryl $C_1$–$C_3$ alkyl optionally substituted with one or more $R^4$ independently;

heteroaryl optionally substituted with one or more $R^4$ independently, —SH; —$SR^5$; $SOR^5$; $SO_2R^5$; —CHO; —CH$(OR^5)_2$; carboxy; —$CO_2R^4$; $NHCONNH_2$; —$NHCSNH_2$; —$NHCONH_2$; —$NHCOR^4$; —$NHSO_2R^5$; —$NHCOR^4$; —$NHSO_2R^5$; —O—CO—($C_1$–$C_5$) alkyl optionally substituted with one or more $R^4$ independently; cyano; nitro; halogen; hydroxy; perhalo $C_1$–$C_7$ alkyl; perhalo $C_1$–$C_7$ alkyloxy; —$SO_2NH_2$; —$SO_2NH(R^5)$; —$SO_2(R^5)_2$; —$CONH_2$; —$CSNH_2$; —$CON_2H_3$; —$CONH(R^5)$; —$CON(R^5)_2$; $C_1$–$C_1$, alkyloxy optionally substituted with $R^4$ independently; $C_2$–$C_{10}$ alkenyloxy optionally substituted with $R^4$; $C_2$–$C_{10}$ alkynyloxy optionally substituted with $R^4$ independently, aryloxy optionally substituted with $R^4$ independently; heteroaryloxy optionally substituted with $R^4$ independently.

More specifically, in the compounds of formula I, $R^2$ may be H; $C_3$–$C_7$ cycloalkyl optionally substituted with one or more $R^4$ independently; $C_3$–$C_7$ cycloheteroalkyl optionally substituted with one or more $R^4$ independently; aryl optionally substituted with one or more $R^4$ independently; aryl $C_1$–$C_3$ alkyl optionally substituted with one or more $R^4$ independently; heteroaryl $C_1$–$C_3$ alkyl optionally substituted with one or more $R^4$ independently; heteroaryl optionally substituted with one or more $R^4$ independently, —SH; —$SR^5$; $SOR^5$; $SO_2R^5$; —CHO; —$CH(OR^5)_2$; carboxy; —$CO_2R^4$; $NHCONNH_2$; —$NHCSNH_2$; —$NHCONH_2$; —$NHCOR^4$; —$NHSO_2R^5$; —O—CO—($C_1$–$C_5$) alkyl optionally substituted with one or more $R^4$ independently; cyano; nitro; halogen; hydroxy; perhalo $C_1$–$C_7$ alkyl; perhalo $C_1$–$C_7$ alkyloxy; —$SO_2NH_2$; —$SO_2NH(R^5)$; —$SO_2(R^5)_2$; —$CONH_2$; —$CSNH_2$; —$CON_2H_3$; —$CONH(R^5)$; —$CON(R^5)_2$; $C_1$–$C_{10}$ alkyloxy optionally substituted with $R^4$ independently; $C_2$–$C_{10}$ alkenyloxy optionally substituted with $R^4$; $C_2$–$C_{10}$ alkynyloxy optionally substituted with $R^4$ independently, aryloxy optionally substituted with $R^4$ independently; heteroaryloxy optionally substituted with $R^4$ independently.

Alternatively, in the compounds of formula I, $R^2$ may be H. In this embodiment, $R^1$ may preferably be C=O; C=S; $C_1$–$C_2$ alkyl substituted with one or more $R^4$ independently; $C_2$ alkenyl substituted with one or more $R^4$ independently; $C_2$ alkynyl; $C_3$–$C_7$ cycloalkyl optionally substituted with one or more $R^4$ independently; $C_3$–$C_7$ cycloheteroalkyl optionally substituted with one or more $R^4$ independently; aryl substituted with one or more $R^4$ independently; aryl $C_1$–$C_3$ alkyl substituted with one or more $R^4$ independently; heteroaryl substituted with one or more $R^4$ independently; heteroaryl $C_1$–$C_3$ alkyl substituted with one or more $R^4$ independently.

In the compounds of formula I, $R^9$ is preferably H, and $R^{10}$ is preferably H.

In the compounds of formula I, $R^6$ and $R^7$ may independently be H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$ alkynyl optionally substituted with one or more $R^4$ independently; $C_3$–$C_7$ cycloalkyl optionally substituted with one or more $R^4$ independently; $C_3$–$C_7$ cycloheteroalkyl optionally substituted with one or more $R^4$ independently; heteroaryl optionally substituted with one or more $R^4$ independently. In particular, $R^6$ and $R^7$ may independently be H; $C_1$–$C_{10}$ alkyl optionally substituted with one or more $R^4$ independently. More particularly, $R^6$ and $R^7$ may independently be H; $C_1$–$C_{10}$ alkyl.

When $R^{10}$ is H, $R^6$ and $R^7$ may independently be H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$ alkynyl optionally substituted with one or more $R^4$ independently; $C_3$–$C_7$ cycloalkyl optionally substituted with one or more $R^4$ independently.

In the compounds of formula I, $R^4$ may be piperidino optionally substituted with one or more $R^8$ independently; piperazino optionally substituted with one or more $R^8$ independently; morpholino optionally substituted with one or more $R^8$ independently; thiomorpholino optionally substituted with one or more $R^8$ independently; pyrrolidino optionally substituted with one or more $R^8$ independently. In this embodiment, $R^6$ and $R^7$ may independently be H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$ alkynyl optionally substituted with one or more $R^4$ independently.

Preferred Compounds

7-Benzyl-8-(6-hydroxymethyl-[1,4]diazepan-1-yl)-1,3-dimethyl-3,7-dihydropurine-2,6-dione.
7-Benzyl-8-(6-hydroxy-[1,4]diazepan-1-yl)-1,3-dimethyl-3,7-dihydropurine-2,6-dione
7-Benzyl-8-(3-hydroxymethyl-[1,4]diazepan-1-yl)-1,3-dimethyl-3,7-dihydropurine-2,6-dione
7-Benzyl-1,3-dimethyl-8-piperazin-1-yl-3,7-dihydropurine-2,6-dione
1,3-Dimethyl-7-(4-methylbenzyl)-8-piperazin-1-yl-3,7-dihydropurine-2,6-dione
3-(1,3-Dimethyl-2,6-dioxo-8-piperazin-1-yl-1,2,3,6-tetrahydropurin-7-ylmethyl) benzonitrile
2-(1,3-Dimethyl-2,6-dioxo-8-piperazin-1-yl-1,2,3,6-tetrahydropurin-7-ylmethyl) benzonitrile.
1,3-Dimethyl-7-(1-phenylethyl)-8-piperazin-1-yl-3,7-dihydropurine-2,6-dione
7-(2-Iodobenzyl)-1,3-dimethyl-8-piperazin-1-yl-3,7-dihydropurine-2,6-dione
1,3-Dimethyl-8-piperazin-1-yl-7-(2-trifluoromethylbenzyl)-3,7-dihydropurine-2,6-dione
1,3-Dimethyl-7-naphthalen-1-ylmethyl-8-piperazin-1-yl-3,7-dihydropurine-2,6-dione
1,3-Dimethyl-7-naphthalen-2-ylmethyl-8-piperazin-1-yl-3,7-dihydropurine-2,6-dione
7-(3-Bromobenzyl)-1,3-dimethyl-8-piperazin-1-yl-3,7-dihydropurine-2,6-dione
7-Benzyl-8-(3-isopropylpiperazin-1-yl)-1,3-dimethyl-3,7-dihydropurine-2,6-dione
7-Benzyl-8-[1,4]diazepan-1-yl-1,3-dimethyl-3,7-dihydropurine-2,6-dione
1,3-Dimethyl-7-(2-oxo-2-pyrrolidin-1-yl-ethyl)-8-piperazin-1-yl-3,7-dihydro-purine-2,6-dione
2-(8-[1,4]Diazepan-1-yl-1,3-dimethyl-2,6-dioxo-1,2,3,6-tetrahydro-purin-7-ylmethyl)-benzonitrile
8-[1,4]Diazepan-1-yl-7-(2-iodo-benzyl)-1,3-dimethyl-3,7-dihydro-purine-2,6-dione
7-(2-Difluoromethoxy-benzyl)-1,3-dimethyl-8-piperazin-1-yl-3,7-dihydro-purine-2,6-dione
7-(2,3-Dimethoxy-benzyl)-1,3-dimethyl-8-piperazin-1-yl-3,7-dihydro-purine-2,6-dione
1,3-Dimethyl-8-piperazin-1-yl-7-(2-trifluoromethoxy-benzyl)-3,7-dihydro-purine-2,6-dione
1,3-Dimethyl-8-piperazin-1-yl-7-(2-trifluoromethylsultanyl-benzyl)-3,7-dihydro-purine-2,6-dione
4-(1,3-Dimethyl-2,6-dioxo-8-piperazin-1-yl-1,2,3,6-tetrahydro-purin-7-yl)-butyronitrile
R)-7-Benzyl-8-(3-isopropylpiperazin-1-yl)-1,3-dimethyl-3,7-dihydropurine-2,6-dione S)-7-Benzyl-8-(3-isopropylpiperazin-1-yl)-1,3-dimethyl-3,7-dihydropurine-2,6-dione
7-Benzyl-8-(6,9-diazaspiro[4.5]dec-9-yl)-1,3-dimethyl-3,7-dihydropurine-2,6-dione
7-Benzyl-8-(piperazin-3-spiro-3'-bicyclo[2,2,1]heptane-1-yl)-1,3-dimethyl-3,7-dihydropurine-2,6-dione
8-[1,4]Diazepan-1-yl-7-(2-methoxy-benzyl)-1,3-dimethyl-3,7-dihydro-purine-2,6-dione
8-[1,4]Diazepan-1-yl-1,3-dimethyl-7-naphthalen-1-ylmethyl-3,7-dihydro-purine-2,6-dione
8-[1,4]Diazepan-1-yl-7-(2-fluoro-benzyl)-1,3-dimethyl-3,7-dihydro-purine-2,6-dione
8-[1,4]Diazepan-1-yl-1,3-dimethyl-7-(2-methyl-benzyl)-3,7-dihydro-purine-2,6-dione
7-(2-Chloro-benzyl)-8-[1,4]diazepan-1-yl-1,3-dimethyl-3,7-dihydro-purine-2,6-dione
7-(2-Bromo-benzyl)-8-[1,4]diazepan-1-yl-1,3-dimethyl-3,7-dihydro-purine-2,6-dione
8-[1,4]Diazepan-1-yl-1,3-dimethyl-7-(2-trifluoromethyl-benzyl)-3,7-dihydro-purine-2,6-dione
8-[1,4]Diazepan-1-yl-1,3-dimethyl-7-(2-nitro-benzyl)-3,7-dihydro-purine-2,6-dione
3-Benzyl-8-piperazin-1-yl-7-(2-trifluoromethyl-benzyl)-3,7-dihydro-purine-2,6-dione
3,7-Dibenzyl-1-(2-hydroxy-ethyl)-8-piperazin-1-yl-3,7-dihydro-purine-2,6-dione
3-Benzyl-7-phenethyl-8-piperazin-1-yl-3,7-dihydro-purine-2,6-dione
3,7-Dibenzyl-8-[1,4]diazepan-1-yl-3,7-dihydro-purine-2,6-dione
7-Benzyl-8-[1,4]diazepan-1-yl-3-methyl-3,7-dihydro-purine-2,6-dione
3,7-Dibenzyl-8-[1,4]diazepan-1-yl-1-propyl-3,7-dihydro-purine-2,6-dione
3,7-Dibenzyl-8-[1,4]diazepan-1-yl-1-(2-hydroxy-ethy)-3,7-dihydro-purine-2,6-dione
2-(3,7-Dibenzyl-8-[1,4]diazepan-1-yl-2,6-dioxo-2,3,6,7-tetrahydro-purin-1-yl) —N,N-diethyl-acetamide
1,3,7-Tribenzyl-8-piperazin-1-yl-3,7-dihydro-purine-2,6-dione
1,3,7-Tribenzyl-8-[1,4]diazepan-1-yl-3,7-dihydro-purine-2,6-dione
(S)-7-Benzyl-8-(3-benzyloxymethylpiperazin-1-yl)-1,3-dimethyl-3,7-dihydropurine-2,6-dione
3,7-Dibenzyl-8-piperazin-1-yl-1-propyl-3,7-dihydro-purine-2,6-dione
3,7-Dibenzyl-8-[1,4]diazepan-1-yl-1-propyl-3,7-dihydro-purine-2,6-dione
3,7-Dibenzyl-8-piperazin-1-yl-3,7-dihydro-purine-2,6-dione
3,7-Dibenzyl-8-[1,4]diazepan-1-yl-3,7-dihydro-purine-2,6-dione
2-(3-Benzyl-2,6-dioxo-8-piperazin-1-yl-1-propyl-1,2,3,6-tetrahydro-purin-7-ylmethyl)-benzonitrile
2-(3-Benzyl-8-[1,4]diazepan-1-yl-2,6-dioxo-1-propyl-1,2,3,6-tetrahydro-purin-7-ylmethyl)-benzonitrile
2-(3-Benzyl-2,6-dioxo-8-piperazin-1-yl-1,2,3,6-tetrahydro-purin-7-ylmethy-1)-benzonitrile
2-(3-Benzyl-8-[1,4]diazepan-1-yl-2,6-dioxo-1,2,3,6-tetrahydro-purin-7-ylmethyl)-benzonitrile
3-Benzyl-7-(2-iodo-benzyl)-8-piperazin-1-yl-1-propyl-3,7-dihydro-purine-2,6-dione
3-Benzyl-8-[1,4]diazepan-1-yl-7-(2-iodo-benzyl)-1-propyl-3,7-dihydro-purine-2,6-dione
3-Benzyl-7-(2-iodo-benzyl)-8-piperazin-1-yl-3,7-dihydro-purine-2,6-dione
3-Benzyl-8-[1,4]diazepan-1-yl-7-(2-iodo-benzyl)-3,7-dihydro-purine-2,6-dione
7-Benzyl-3-methyl-8-piperazin-1-yl-1-propyl-3,7-dihydro-purine-2,6-dione
7-Benzyl-8-[1,4]diazepan-1-yl-3-methyl-1-propyl-3,7-dihydro-purine-2,6-dione
7-Benzyl-3-methyl-8-piperazin-1-yl-3,7-dihydro-purine-2,6-dione
7-Benzyl-8-[1,4]diazepan-1-yl-3-methyl-3,7-dihydro-purine-2,6-dione
2-(3-Methyl-2,6-dioxo-8-piperazin-1-yl-1-propyl-1,2,3,6-tetrahydro-purin-7-ylmethyl)-benzonitrile
2-(8-[1,4]Diazepan-1-yl-3-methyl-2,6-dioxo-1-propyl-1,2,3,6-tetrahydro-purin-7-ylmethyl)-benzonitrile
2-(8-[1,4]Diazepan-1-yl-3-methyl-2,6-dioxo-1,2,3,6-tetrahydro-purin-7-ylmethyl)-benzonitrile
7-(2-Iodo-benzyl)-3-methyl-8-piperazin-1-yl-1-propyl-3,7-dihydro-purine-2,6-dione
8-[1,4]Diazepan-1-yl-7-(2-iodo-benzyl)-3-methyl-1-propyl-3,7-dihydropurine-2,6-dione
7-(2-Iodo-benzyl)-3-methyl-8-piperazin-1-yl-3,7-dihydro-purine-2,6-dione
8-[1,4]Diazepan-1-yl-7-(2-iodo-benzyl)-3-methyl-3,7-dihydro-purine-2,6-dione
3-Benzyl-8-[1,4]diazepan-1-yl-1-(3-hydroxy-propyl)-7-(2-iodo-benzyl)-3,7-dihydro-purine-2,6-dione
3-Benzyl-8-[1,4]diazepan-1-yl-1-(2-ethoxy-ethyl)-7-(2-iodo-benzyl)-3,7-dihydro-purine-2,6-dione
7-Benzyl-8-[1,4]diazepan-1-yl-3-methyl-1-(3-phenyl-allyl)-3,7-dihydro-purine-2,6-dione
7-Benzyl-8-[1,4]diazepan-1-yl-3-methyl-1-(2-oxo-2-phenyl-ethyl)-3,7-dihydro-purine-2,6-dione
2-(7-Benzyl-8-[1,4]diazepan-1-yl-3-methyl-2,6-dioxo-2,3,6,7-tetrahydro-purin-1-ylmethyl)-benzonitrile
(7-Benzyl-8-[1,4]diazepan-1-yl-3-methyl-2,6-dioxo-2,3,6,7-tetrahydro-purin-1-yl)-acetonitrile
3-Methyl-7-(2-methyl-thiazol-4-ylmethyl)-8-piperazin-1-yl-3,7-dihydro-purine-2,6-dione
8-[1,4]Diazepan-1-yl-3-methyl-7-(2-methyl-thiazol-4-ylmethyl)-3,7-dihydro-purine-2,6-dione
3-Methyl-7-(2-oxo-2-phenyl-ethyl)-8-piperazin-1-yl-3,7-dihydro-purine-2,6-dione
8-[1,4]Diazepan-1-yl-3-methyl-7-(2-oxo-2-phenyl-ethyl)-3,7-dihydro-purine-2,6-dione
8-[1,4]Diazepan-1-yl-3-methyl-7-phenethyl-3,7-dihydro-purine-2,6-dione
8-[1,4]Diazepan-1-yl-1-(3-hydroxy-propyl)-7-(2-iodo-benzyl)-3-methyl-3,7-dihydro-purine-2,6-dione
1-(3-Hydroxy-propyl)-7-(2-iodo-benzyl)-3-methyl-8-piperazin-1-yl-3,7-dihydro-purine-2,6-dione
8-[1,4]Diazepan-1-yl-1-(2-ethoxy-ethyl)-7-(2-iodo-benzyl)-3-methyl-3,7-dihydro-purine-2,6-dione
1-(2-Ethoxy-ethyl)-7-(2-iodo-benzyl)-3-methyl-8-piperazin-1-yl-3,7-dihydro-purine-2,6-dione
8-[1,4]Diazepan-1-yl-7-(2-iodo-benzyl)-3-methyl-1-(2-phenoxy-ethyl)-3,7-dihydro-purine-2,6-dione
8-[1,4]Diazepan-1-yl-7-(2-iodo-benzyl)-1-[2-(2-methoxy-ethoxy)-ethyl]-3-methyl-3,7-dihydro-purine-2,6-dione
7-(2-Iodo-benzyl)-1-[2-(2-methoxy-ethoxy)-ethyl]-3-methyl-8-piperazin-1-yl-3,7-dihydro-purine-2,6-dione
8-[1,4]Diazepan-1-yl-1-(3,5-dimethoxy-benzyl)-7-(2-iodo-benzyl)-3-methyl-3,7-dihydro-purine-2,6-dione
8-[1,4]Diazepan-1-yl-7-(2-iodo-benzyl)-1-(3-methoxy-benzyl)-3-methyl-3,7-dihydro-purine-2,6-dione
7-Biphenyl-2-ylmethyl-8-[1,4]diazepan-1-yl-3-methyl-3,7-dihydro-purine-2,6-dione 7-(2-Bromo-benzyl)-8-[1,4]diazepan-1-yl-3-methyl-3,7-dihydro-purine-2,6-dione
7-(2-Chloro-benzyl)-8-[1,4]diazepan-1-yl-3-methyl-3,7-dihydro-purine-2,6-dione
7-Benzyl-8-(3,5-dimethyl-piperazin-1-yl)-1,3-dimethyl-3,7-dihydro-purine-2,6-dione
7-(4-Methoxybenzyl)-1,3-dimethyl-8-piperazin-1-yl-3,7-dihydropurine-2,6-dione
(1,3-Dimethyl-2,6-dioxo-8-piperazin-1-yl-1,2,3,6-tetrahydropurin-7-yl)-phenylacetic acid methyl ester
7-(5-Chloro-2-nitrobenzyl)-1,3-dimethyl-8-piperazin-1-yl-3,7-dihydropurine-2,6-dione
4-(1,3-Dimethyl-2,6-dioxo-8-piperazin-1-yl-1,2,3,6-tetrahydropurin-7-ylmethyl) benzonitrile
7-(4-Methanesulfonylbenzyl)-1,3-dimethyl-8-piperazin-1-yl-3,7-dihydropurine-2,6-dione
7-(2-Fluoro-6-nitrobenzyl)-1,3-dimethyl-8-piperazin-1-yl-3,7-dihydropurine-2,6-dione
7-(4-Benzyloxybenzyl)-1,3-dimethyl-8-piperazin-1-yl-3,7-dihydropurine-2,6-dione
7-(2,4-Dichlorobenzyl)-1,3-dimethyl-8-piperazin-1-yl-3,7-dihydropurine-2,6-dione
1,3-Dimethyl-8-piperazin-1-yl-7-(4-trifluoromethylbenzyl)-3,7-dihydropurine-2,6-dione
7-Biphenyl-4-ylmethyl-1,3-dimethyl-8-piperazin-1-yl-3,7-dihydropurine-2,6-dione
3-(1,3-Dimethyl-2,6-dioxo-8-piperazin-1-yl-1,2,3,6-tetrahydropurin-7-ylmethyl) benzoic acid methyl ester
4-(1,3-Dimethyl-2,6-dioxo-8-piperazin-1-yl-1,2,3,6-tetrahydropurin-7-ylmethyl) benzoic acid methyl ester
7-Biphenyl-2-ylmethyl-1,3-dimethyl-8-piperazin-1-yl-3,7-dihydropurine-2,6-dione
7-(4-tert-Butylbenzyl)-1,3-dimethyl-8-piperazin-1-yl-3,7-dihydropurine-2,6-dione
1,3-Dimethyl-8-piperazin-1-yl-7-(4-trifluoromethoxybenzyl)-3,7-dihydropurine-2,6-dione
7-(3,4-Dichlorobenzyl)-1,3-dimethyl-8-piperazin-1-yl-3,7-dihydropurine-2,6-dione
1,3-Dimethyl-8-piperazin-1-yl-7-(4-[1,2,3]thiadiazol-4-ylbenzyl)-3,7-dihydropurine-2,6-dione
4-(1,3-Dimethyl-2,6-dioxo-8-piperazin-1-yl-1,2,3,6-tetrahydropurin-7-ylmethyl)-3-methoxybenzoic acid methyl ester
7-Cyclohexylmethyl-1,3-dimethyl-8-piperazin-1-yl-3,7-dihydro-purine-2,6-dione
7-Benzyl-8-(2,5-diaza-bicyclo[2.2.1]hept-2-yl)-1,3-dimethyl-3,7-dihydro-purine-2,6-dione
8-(6-Benzyl-[1,4]diazepan-1-yl)-7-(2-iodo-benzyl)-1,3-dimethyl-3,7-dihydro-purine-2,6-dione
(S)-7=Benzyl-8-(3-hydroxymethylpiperazin-1-yl)-1,3-dimethyl-3,7-dihydropurine-2,6-dione
8-[1,4]Diazepan-1-yl-1,3-dimethyl-7-(2-oxo-2-pyrrolidin-1-yl-ethyl)-3,7-dihydro-purine-2,6-dione
7-(2-Iodo-benzyl)-1,3-dimethyl-8-(6-pyridin-2-ylmethyl-[1,4]diazepan-1-yl)-3,7-dihydro-purine-2,6-dione
7-(2-Bromo-benzyl)-1,3-dimethyl-8-(6-pyridin-2-ylmethyl-[1,4]diazepan-1-yl)-3,7-dihydro-purine-2,6-dione
(S) 7-Benzyl-8-(3-benzyl-piperazin-1-yl)-1,3-dimethyl-3,7-dihydro-purine-2,6-dione
7-Benzyl-1,3-dimethyl-8-(3-phenethyl-piperazin-1-yl)-3,7-dihydro-purine-2,6-dione
(R)-7-Benzyl-8-(3-benzylpiperazin-1-yl)-1,3-dimethyl-3,7-dihydropurine-2,6-dione
7-Benzyl-8-(3-(2-hydroxy-benzyl)-piperazin-1-yl)-1,3-dimethyl-3,7-dihydro-purine-2,6-dione
7-Benzyl-8-(3-(2-methoxy-benzyl)-piperazin-1-yl)1,3-dimethyl-3,7-dihydro-purine-2,6-dione
(R)-7-Benzyl-8-(3-(4-methoxy-benzyl)-piperazin-1-yl)1,3-dimethyl-3,7-dihydro-purine-2,6-dione
(R)-7-Benzyl-8-(3-(4-hydroxy-benzyl)-piperazin-1-yl)-1,3-dimethyl-3,7-dihydro-purine-2,6-dione
(R)-7-Benzyl-1,3-dimethyl-8-(3-(4-nitro-benzyl)-piperazin-1-yl)-3,7-dihydro-purine-2,6-dione
(R)-7-Benzyl-8-(3-(4-fluorobenzyl)-piperazin-1-yl)-1,3-dimethyl-3,7-dihydro-purine-2,6-dione
(R)-4-(4-(7-Benzyl-1,3-dimethyl-2,6-dioxo-2,3,6,7-tetrahydro-1H-purin-8-yl)-piperazin-2-ylmethyl)-benzonitrile
(R)-6-(8-(3-Benzyl-piperazin-1-yl)-1,3-dimethyl-2,6-dioxo-1,2,3,6-tetrahydro-purin-7-ylmethyl)-nicotinonitrile
(R)-7-Benzyl-1,3-dimethyl-8-(3-thiazol-4-ylmethyl-piperazin-1-yl)-3,7-dihydro-purine-2,6-dione
(R)-2-[1,3-Dimethyl-2,6-dioxo-8-(3-thiophen-2-ylmethyl-piperazin-1-yl)-1,2,3,6-tetrahydro-purin-7-ylmethyl]-benzonitrile
7-Benzyl-8-[1,4]diazepan-1-yl-3-methyl-1-(tetrahydro-furan-2-ylmethyl)-3,7-dihydro-purine-2,6-dione
7-Benzyl-1-(2-cyclohexyl-ethyl)-B-[1,4]diazepan-1-yl-3-methyl-3,7-dihydro-purine-2,6-dione
7-Benzyl-8-[1,4]diazepan-1-yl-3-methyl-1-(5-methyl-hexyl)-3,7-dihydro-purine-2,6-dione
7-Benzyl-8-[1,4]diazepan-1-yl-3-methyl-1-(3-methyl-butyl)-3,7-dihydro-purine-2,6-dione
7-Benzyl-8-[1,4]diazepan-1-yl-1-(2-ethoxy-ethyl)-3-methyl-3,7-dihydro-purine-2,6-dione
8-[1,4]Diazepan-1-yl-7-(2-iodo-benzyl)-3-methyl-1-(tetrahydro-furan-2-ylmethyl)-3,7-dihydro-purine-2,6-dione
7-(2-Iodo-benzyl)-3-methyl-8-piperazin-1-yl-1-(tetrahydro-furan-2-ylmethyl)-3,7-dihydro-purine-2,6-dione
8-[1,4]Diazepan-1-yl-7-(2-iodo-benzyl)-3-methyl-1-(tetrahydro-pyran-2-ylmethyl)-3,7-dihydro-purine-2,6-dione
7-(2-Iodo-benzyl)-3-methyl-8-piperazin-1-yl-1-(tetrahydro-pyran-2-ylmethyl)-3,7-dihydro-purine-2,6-dione
7-(2-Iodo-benzyl)-3-methyl-1-(2-phenoxy-ethyl)-8-piperazin-1-yl-3,7-dihydro-purine-2,6-dione
8-[1,4]Diazepan-1-yl-7-(2-iodo-benzyl)-1-(2-methoxy-ethyl)-3-methyl-3,7-dihydro-purine-2,6-dione
7-(2-Iodo-benzyl)-1-(2-methoxy-ethyl)-3-methyl-8-piperazin-1-yl-3,7-dihydro-purine-2,6-dione
1-(2-Benzyloxy-ethyl)-8-[1,4]diazepan-1-yl-7-(?-iodo-benzyl)-3-methyl-3,7-dihydro-purine-2,6-dione
1-(2-Benzyloxy-ethyl)-7-(2-iodo-benzyl)-3-methyl-8-piperazin-1-yl-3,7-dihydro-purine-2,6-dione
1-(3,5-Dimethoxy-benzyl)-7-(2-iodo-benzyl)-3-methyl-8-piperazin-1-yl-3,7-dihydro-purine-2,6-dione
7-(2-Iodo-benzyl)-1-(3-methoxy-benzyl)-3-methyl-8-piperazin-1-yl-3,7-dihydro-purine-2,6-dione
8-[1,4]Diazepan-1-yl-7-(2-iodo-benzyl)-3-methyl-1-(3-trifluoromethoxy-benzyl)-3,7-dihydro-purine-2,6-dione
7-(2-Iodo-benzyl)-3-methyl-8-piperazin-1-yl-1-(3-trifluoromethoxy-benzyl)-3,7-dihydro-purine-2,6-dione
8-[1,4]Diazepan-1-yl-1-(2-hydroxy-propyl)-7-(2-iodo-benzyl)-3-methyl-3,7-dihydro-purine-2,6-dione
8-[1,4]Diazepan-1-yl-1-(2,2-diethoxy-ethyl)-7-(2-iodo-benzyl)-3-methyl-3,7-dihydro-purine-2,6-dion
8-[1,4]Diazepan-1-yl—(2,2-dimethoxy-ethyl)-7-(2-iodo-benzyl)-3-methyl-3,7-dihydro-purine-2,6-dione
8-[1,4]Diazepan-1-yl-1-(2-[1,3]dioxolan-2-yl-ethyl)-7-(2-iodo-benzyl)-3-methyl-3,7-dihydro-purine-2,6-dione
1-(2-[1,3]Dioxolan-2-yl-ethyl)-7-(2-iodo-benzyl)-3-methyl-8-piperazin-1-yl-3,7-dihydro-purine-2,6-dione
1-[1,3]Dioxolan-2-ylmethyl-7-(2-iodo-benzyl)-3-methyl-8-piperazin-1-yl-3,7-dihydro-purine-2,6-dione
8-[1,4]Diazepan-1-yl-1-(2-[t,3]dioxan-2-yl-ethyl)-7-(2-iodo-benzyl)-3-methyl-3,7-dihydro-purine-2,6-dione 1-(2-[1,3]Dioxan-2-yl-ethyl)-7-(2-iodo-benzyl)-3-methyl-8-piperazin-1-yl-3,7-dihydro-purine-2,6-dione
8-[1,4]Diazepan-1-yl-1-(2,3-dihydroxy-propyl)-7-(2-iodo-benzyl)-3-methyl-3,7-dihydro-purine-2,6-dione
1-(2,3-Dihydroxy-propyl)-7-(-iodo-benzyl)-3-methyl-8-piperazin-1-yl-3,7-dihydro-purine-2,6-dione
8-[1,4]Diazepan-1-yl-1-(3-hydroxy-2-methyl-propyl)-7-(2-iodo-benzyl)-3-methyl-3,7-dihydro-purine-2,6-dione
1-(3-Hydroxy-2-methyl-propyl)-7-(2-iodo-benzyl)-3-methyl-8-piperazin-1-yl-3,7-dihydro-purine-2,6-dione
8-[1,4]Diazepan-1-yl-7-(2-iodo-benzyl)-3-methyl-1-[3-(tetrahydro-pyran-2-yloxy)-propyl]-3,7-dihydropurine-2,6-dione
8-[1,4]Diazepan-1-yl-1-(2-fluoro-ethyl)-7-(2-iodo-benzyl)-3-methyl-3,7-dihydro-purine-2,6-dione
7-Benzyl-8-[1,4]diazepan-1-yl-1-(3-hydroxy-propyl)-3-methyl-3,7-dihydro-purine-2,6-dione
7-Biphenyl-2-ylmethyl-8-[1,4]diazepan-1-yl-3-methyl-3,7-dihydro-purine-2,6-dione In another aspect, the invention provides compounds in one of the three groups A, B and C.

Group A:

In the compounds of group A, the invention provides compounds of formula I

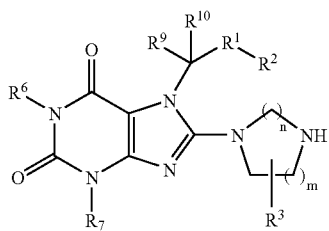

I wherein
n and m is one or two independently;
$R^1$ is C=O; C=S; $C_1$–$C_2$ alkyl; $C_2$ alkenyl; $C_2$ alkynyl; $C_3$–$C_7$ cycloalkyl; $C_3$–$C_7$ cycloheteroalkyl; aryl; aryl-$C_1$–$C_3$ alkyl; heteroaryl; heteroaryl-$C_1$–$C_3$ alkyl, wherein each alkyl, alkenyl, cycloalkyl, cycloheteroalkyl, aryl, aryl-$C_1$–$C_3$ alkyl, heteroaryl, or heteroaryl-$C_1$–$C_3$ alkyl is optionally substituted with one or more $R^4$ independently;
$R^2$ is H; $C_1$–$C_7$ alkyl; $C_2$–$C_7$ alkenyl; $C_2$–$C_7$ alkynyl; $C_3$–$C_7$ cycloalkyl; $C_3$–$C_7$ cycloheteroalkyl; aryl; aryl-$C_1$–$C_3$ alkyl; heteroaryl-$C_1$–$C_3$ alkyl; heteroaryl; cyano; halogen; hydroxy, nitro; —SH; —$SR^5$; —$SOR^5$; —$SO_2R^5$; carboxy; —$CO_2R^4$; —$CON(R^5)_2$; $C_1$–$C_{10}$ alkyloxy; $C_2$–$C_{10}$ alkenyloxy; $C_2$–$C_{10}$ alkynyloxy, aryloxy; heteroaryloxy, wherein each alkyl, alkenyl, alkynyl, cycloalkyl, cycloheteroalkyl, aryl, aryl-$C_1$–$C_3$ alkyl, heteroaryl, heteroaryl-$C_1$–$C_3$ alkyl, alkyloxy; alkenyloxy; alkynyloxy, aryloxy, or heteroaryloxy is optionally substituted with one or more $R^{11}$ independently;
$R^3$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; aryl-$C_1$–$C_3$ alkyl; heteroaryl-$C_1$–$C_3$ alkyl; heteroaryl; $C_1$–$C_{10}$alkyl-O–$C_1$–$C_5$alkyl; carboxy; cyano; nitro; halogen; hydroxy; wherein each alkyl, alkenyl, alkynyl, cycloalkyl, cycloheteroalkyl, aryl, aryl-$C_1$–$C_3$ alkyl, heteroaryl-$C_1$–$C_3$ alkyl, heteroaryl, or alkyl-O-alkyl is optionally substituted with one or more $R^{12}$ independently; two $R^3$ attached to the same carbon atom may form a spiro system;

$R^4$, $R^{11}$, $R^{12}$, and $R^{17}$ are independently $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; heteroaryl; cyano; halogen; hydroxy, nitro; trifluormethyl; $N(R^{13})_2$; =O; =S; $C_1$–$C_{10}$ alkyloxy; $C_2$–$C_{10}$ alkenyloxy; $C_2$–$C_{10}$ alkynyloxy; aryloxy; heteroaryloxy, wherein each alkyl, alkenyl, alkynyl, cycloalkyl, cycloheteroalkyl, aryl, heteroaryl, alkyloxy; alkenyloxy; alkynyloxy, aryloxy, or heteroaryloxy is optionally substituted with one or more $R^8$ independently; two $R^4$ attached to the same carbon atom may form a spiroheterocyclic system, preferably hydantoine; thiohydantoine; oxazolidine-2,5-dione;
$R^5$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; aryl-$C_1$–$C_5$ alkyl; heteroaryl; heteroaryl-$C_1$–$C_5$ alkyl, wherein each alkyl, alkenyl, alkynyl, cycloalkyl, cycloheteroalkyl, aryl, aryl alkyl, heteroaryl, or heteroaryl alkyl is optionally substituted with one or more $R^{14}$ independently;
$R^6$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; heteroaryl, wherein each each alkyl, alkenyl, alkynyl, cycloalkyl, cycloheteroalkyl, aryl, or heteroaryl is optionally substituted with one or more $R^{15}$ independently;
$R^7$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; heteroaryl, wherein each each alkyl, alkenyl, alkynyl, cycloalkyl, cycloheteroalkyl, aryl, or heteroaryl is optionally substituted with one or more $R^{16}$ independently;
$R^8$, $R^{14}$, $R^{15}$, and $R^{16}$ are independently H; nitro; —$OCH_3$; cyano; halogen; —OH; —SH; —$SCH_3$;
$R^9$ is H; halogen; $C_1$–$C_{10}$ alkyl or aryl, wherein alkyl or aryl is optionally substituted with one or more $R^{17}$ independently
$R^{10}$ is H; halogen;
or, $R^9$ and $R^{10}$ may be connected to form a cyclopropyl ring;
$R^{13}$ is H; $C_1$–$C_{10}$ alkyl or aryl;

or a salt thereof with a pharmaceutically acceptable acid or base;

with the exception of the following compounds:
1,3-dimethyl-7-(2-oxo-propyl)-8-piperazin-1-yl-3,7-dihydro-purine-2,6-dione,
1,3,1',3',7'-pentamethyl-8-piperazin-1-yl-3,7,3',7'-tetrahydro-7,8'-methanediyl-bis-purine-2,6-dione,
3,4,5-trimethoxy-benzoic acid 2-(1,3-dimethyl-2,6-dioxo-8-piperazin-1-yl-1,2,3,6-tetrahydro-purin-7-yl)-ethyl ester,
7-[2-Hydroxy-3-(4-methoxy-phenoxy)-propyl]-3-methyl-8-piperazin-1-yl-3,7-dihydro-purine-2,6-dione,
7-[2-hydroxy-2-(4-nitro-phenyl)-ethyl]-3-methyl-8-piperazin-1-yl-3,7,8,9-tetrahydro-purine-2,6-dione,
7-Benzyl-3-methyl-8-piperazin-1-yl-3,7-dihydro-purine-2,6-dione,
7-(4-Chloro-benzyl)-3-methyl-8-piperazin-1-yl-3,7-dihydro-purine-2,6-dione,
7-(2-Chloro-benzyl)-3-methyl-8-piperazin-1-yl-3,7-dihydro-purine-2,6-dione,
7-Ethyl-3-methyl-8-piperazin-1-yl-3,7-dihydro-purine-2,6-dione,
3-Methyl-8-piperazin-1-yl-1,7-dipropyl-3,7-dihydro-purine-2,6-dione,
3-Methyl-7-(3-methyl-butyl)-8-piperazin-1-yl-3,7-dihydro-purine-2,6-dione,
7-Butyl-3-methyl-8-piperazin-1-yl-3,7-dihydro-purine-2,6-dione,
3-Methyl-7-(3-phenyl-propyl)-8-piperazin-1-yl-3,7-dihydro-purine-2,6-dione, 7-But-2-enyl-3-methyl-8-piperazin-1-yl-3,7-dihydro-purine-2,6-dione,
7-(3-Chloro-but-2-enyl)-3-methyl-8-piperazin-1-yl-3,7-dihydro-purine-2,6-dione,
7-Heptyl-3-methyl-8-piperazin-1-yl-3,7-dihydro-purine-2,6-dione,
3-Methyl-7-(1-phenyl-ethyl)-8-piperazin-1-yl-3,7-dihydro-purine-2,6-dione,
3-Methyl-7-(3-methyl-benzyl),-8-piperazin-1-yl-3,7-dihydro-purine-2,6-dione,
3-Methyl-7-propyl-8-piperazin-1-yl-3,7-dihydro-purine-2,6-dione, and
3-Methyl-7-pentyl-8-piperazin-1-yl-3,7-dihydro-purine-2,6-dione.

Group B:

In the compounds of group B, the invention provides compounds of formula I

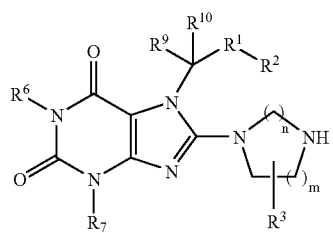

I wherein n and m is one or two independently;

with the proviso that if n is 2 then m is also 2;

$R^1$ is C=O; C=S; $C_1$–$C_2$ alkyl; $C_2$ alkenyl; C2 alkynyl $C_3$–$C_7$ cycloalkyl; $C_3$–$C_7$ cycloheteroalkyl; aryl; aryl-$C_1$–$C_3$ alkyl; heteroaryl; heteroaryl-$C_1$–$C_3$ alkyl, wherein each alkyl, alkenyl, cycloalkyl, cycloheteroalkyl, aryl, aryl-$C_1$–$C_3$ alkyl, heteroaryl, or heteroaryl-$C_1$–$C_3$ alkyl is optionally substituted with one or more $R^4$ independently;

$R^2$ is H; $C_1$–$C_7$ alkyl; $C_2$–$C_7$ alkenyl; $C_2$–$C_7$ alkynyl; $C_3$–$C_7$ cycloalkyl; $C_3$–$C_7$ cycloheteroalkyl; aryl; aryl-$C_1$–$C_3$ alkyl; heteroaryl-$C_1$–$C_3$ alkyl; heteroaryl; cyano; halogen; hydroxy, nitro; —SH; —$SR^5$; —$SOR^5$; —$SO_2R^5$; carboxy; —$CO_2R^4$; —CON($R^5$)$_2$; $C_1$–$C_{10}$ alkyloxy; $C_2$–$C_{10}$ alkenyloxy; $C_2$–$C_{10}$ alkynyloxy, aryloxy; heteroaryloxy, wherein each alkyl, alkenyl, alkynyl, cycloalkyl, cycloheteroalkyl, aryl, aryl-$C_1$–$C_3$ alkyl, heteroaryl, heteroaryl-$C_1$–$C_3$ alkyl, alkyloxy; alkenyloxy; alkynyloxy, aryloxy, or heteroaryloxy is optionally substituted with one or more $R^{11}$ independently;

$R^3$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; aryl-$C_1$–$C_3$ alkyl; heteroaryl-$C_1$–$C_3$ alkyl; heteroaryl; $C_1$–$C_{10}$ alkyl-O—$C_1$–$C_5$alkyl; carboxy; cyano; nitro; halogen; hydroxy; wherein each alkyl, alkenyl, alkynyl, cycloalkyl, cycloheteroalkyl, aryl, aryl-$C_1$–$C_3$ alkyl, heteroaryl-$C_1$–$C_3$ alkyl, heteroaryl, or alkyl-O-alkyl is optionally substituted with one or more $R^{12}$ independently; two $R^3$ attached to the same carbon atom may form a spiro system;

$R^4$, $R^{11}$, $R^{12}$, and $R^{17}$ are independently $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; heteroaryl; cyano; halogen; hydroxy, nitro; trifluormethyl; N($R^{13}$)$_2$; =O; =S; $C_1$–$C_{10}$ alkyloxy; $C_2$–$C_{10}$ alkenyloxy; $C^2$–$C_{10}$ alkynyloxy; aryloxy; heteroaryloxy, wherein each alkyl, alkenyl, alkynyl, cycloalkyl, cycloheteroalkyl, aryl, heteroaryl, alkyloxy; alkenyloxy; alkynyloxy, aryloxy, or heteroaryloxy is optionally substituted with one or more $R^8$ independently; two $R^4$ attached to the same carbon atom may form a spiroheterocyclic system, preferably hydantoine; thiohydantoine; oxazolidine-2,5-dione;

$R^5$ is H; $C_1$–$C_{10}$ alkyl; $C_2$–$C_{10}$alkenyl; $C_2$–$C_{10}$ alkynyl; $C_3$–$C_7$ cycloalkyl; $C_3$–$C_7$ cycloheteroalkyl; aryl; aryl-$C_1$–$C_5$ alkyl; heteroaryl; heteroaryl-$C_1$–$C_5$ alkyl, wherein each alkyl, alkenyl, alkynyl, cycloalkyl, cycloheteroalkyl, aryl, aryl alkyl, heteroaryl, or heteroaryl alkyl is optionally substituted with one or more $R^{14}$ independently;

$R^6$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; heteroaryl, wherein each each alkyl, alkenyl, alkynyl, cycloalkyl, cycloheteroalkyl, aryl, or heteroaryl is optionally substituted with one or more $R^{15}$ independently;

$R^7$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; heteroaryl, wherein each each alkyl, alkenyl, alkynyl, cycloalkyl, cycloheteroalkyl, aryl, or heteroaryl is optionally substituted with one or more $R^{16}$ independently;

$R^8$, $R^{14}$, $R^{15}$, and $R^{16}$ are independently H; nitro; —$OCH_3$; cyano; halogen; —OH; —SH; —$SCH_3$;

$R^9$ is H; halogen; $C_1$–$C_{10}$ alkyl optionally substituted with one or more $R^{17}$ independently $R^{10}$ is H; halogen;

or, $R^9$ and $R^{10}$ may be connected to form a cyclopropyl ring;

$R^{13}$ is H; $C_1$–$C_{10}$ alkyl or aryl;

or a salt thereof with a pharmaceutically acceptable acid or base.

Group C:

In the compounds of group C, the invention provides compounds of formula I

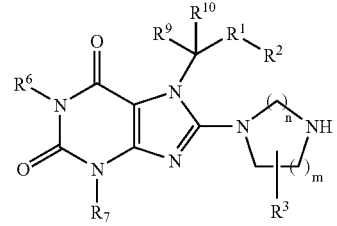

I wherein n and m is one or two independently;

$R^1$ is C=O; C=S; $C_1$–$C_2$ alkyl; $C_2$ alkenyl; $C_2$ alkynyl $C_3$–$C_7$ cycloalkyl; $C_3$–$C_7$ cycloheteroalkyl; aryl; aryl-$C_1$–$C_3$ alkyl; heteroaryl; heteroaryl-$C_1$–$C_3$ alkyl, wherein each alkyl, alkenyl, cycloalkyl, cycloheteroalkyl, aryl, aryl-$C_1$–$C_3$ alkyl, heteroaryl, or heteroaryl-$C_1$–$C_3$ alkyl is optionally substituted with one or more $R^4$ independently;

$R^2$ is H; $C_1$–$C_7$ alkyl; $C_2$–$C_7$ alkenyl; $C_2$–$C_7$ alkynyl; $C_3$–$C_7$ cycloalkyl; $C_3$–$C_7$ cycloheteroalkyl; aryl; aryl-$C_1$–$C_3$ alkyl; heteroaryl-$C_1$–$C_3$ alkyl; heteroaryl; cyano; halogen; hydroxy, nitro; —SH; —$SR^5$; —$SOR^5$; —$SO_2R^5$; carboxy; —$CO_2R^4$; —CON($R^5$)$_2$; $C_1$–$C_{10}$ alkyloxy; $C_2$–$C_{10}$ alkenyloxy; $C_2$–$C_{10}$ alkynyloxy, aryloxy; heteroaryloxy, wherein each alkyl, alkenyl, alkynyl, cycloalkyl, cycloheteroalkyl, aryl, aryl-$C_1$–$C_3$ alkyl, heteroaryl, heteroaryl- $C_1$–$C_3$ alkyl, alkyloxy; alkenyloxy; alkynyloxy, aryloxy, or heteroaryloxy is optionally substituted with one or more $R^{11}$ independently;

$R^3$ is $C_1$–$C_{10}$ alkyl; $C_2$–$C_{10}$ alkenyl; $C_2$–$C_{10}$alkynyl; $C_3$–$C_7$ cycloalkyl; $C_3$–$C_7$ cycloheteroalkyl; aryl; aryl-$C_1$–$C_3$ alkyl; heteroaryl-$C_1$–$C_3$ alkyl; heteroaryl; $C_1$–$C_{10}$ alkyl-O—$C_1$–$C_5$alkyl; carboxy; cyano; nitro; halogen; hydroxy; wherein each alkyl, alkenyl, alkynyl, cycloalkyl, cycloheteroalkyl, aryl, aryl-$C_1$–$C_3$ alkyl, heteroaryl-$C_1$–$C_3$ alkyl, heteroaryl, or alkyl-O-alkyl is optionally substituted with one or more $R^{12}$ independently; two $R^8$ attached to the same carbon atom may form a spiro system;

$R^4$, $R^{11}$, $R^{12}$, and $R^{17}$ are independently $C_1$–$C_{10}$ alkyl; $C_2$–$C_{10}$ alkenyl; $C_2$–$C_{10}$alkynyl; $C_3$–$C_7$ cycloalkyl; $C_3$–$C_7$ cycloheteroalkyl; aryl; heteroaryl; cyano; halogen; hydroxy, nitro; trifluormethyl; $N(R^{13})_2$; =O; =S; $C_1$–$C_{10}$ alkyloxy; $C_2$–$C_{10}$ alkenyloxy; $C_2$–$C_{10}$ alkynyloxy; aryloxy; heteroaryloxy, wherein each alkyl, alkenyl, alkynyl, cycloalkyl, cycloheteroalkyl, aryl, heteroaryl, alkyloxy; alkenyloxy; alkynyloxy, aryloxy, or heteroaryloxy is optionally substituted with one or more $R^8$ independently; two $R^4$ attached to the same carbon atom may form a spiroheterocyclic system, preferably hydantoine; thiohydantoine; oxazolidine-2,5-dione;

$R^5$ is H; $C_1$–$C_{10}$ alkyl; $C_2$–$C_{10}$alkenyl; $C_2$–$C_{10}$ alkynyl; $C_3$–$C_7$ cycloalkyl; $C_3$–$C_7$ cycloheteroalkyl; aryl; aryl-$C_1$–$C_5$ alkyl; heteroaryl; heteroaryl-$C_1$–$C_5$ alkyl, wherein each alkyl, alkenyl, alkynyl, cycloalkyl, cycloheteroalkyl, aryl, aryl alkyl, heteroaryl, or heteroaryl alkyl is optionally substituted with one or more $R^{14}$ independently;

$R^6$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; heteroaryl, wherein each each alkyl, alkenyl, alkynyl, cycloalkyl, cycloheteroalkyl, aryl, or heteroaryl is optionally substituted with one or more $R^{15}$ independently;

$R^7$ is H; $C_1$–$C_{10}$ alkyl; $C_2$–$C_{10}$ alkenyl; $C_2$–$C_{10}$ alkynyl; $C_3$–$C_7$ cycloalkyl; $C_3$–$C_7$ cycloheteroalkyl; aryl; heteroaryl, wherein each each alkyl, alkenyl, alkynyl, cycloalkyl, cycloheteroalkyl, aryl, or heteroaryl is optionally substituted with one or more $R^{16}$ independently;

$R^8$, $R^{14}$, $R^{15}$, and $R^{16}$ are independently H; nitro; —OCH$_3$; cyano; halogen; —OH; —SH; —SCH$_3$;

$R^9$ is H; halogen; $C_1$–$C_{10}$ alkyl optionally substituted with one or more $R^{17}$ independently $R^{10}$ is H; halogen; or, $R^9$ and $R^{10}$ may be connected to form a cyclopropyl ring; $R^{13}$ is H; $C_1$–$C_{10}$ alkyl or aryl;

or a salt thereof with a pharmaceutically acceptable acid or base.

In a further embodiment of the compounds of group A, B and C, $R^1$ is C=O; $C_1$–$C_2$ alkyl; $C_2$ alkenyl; $C_2$ alkynyl; $C_3$–$C_7$ cycloalkyl; $C_3$–$C_7$ cycloheteroalkyl; aryl; or heteroaryl, wherein each alkyl, alkenyl, cycloalkyl, cycloheteroalkyl, aryl, or heteroaryl is optionally substituted with one or more $R^4$ independently.

In a further embodiment of the compounds of group A, B and C, $R^1$ is C=O; $C_1$–$C_2$alkyl; $C_3$–$C_7$ cycloalkyl; aryl; or heteroaryl, wherein each alkyl, cycloalkyl, aryl, or heteroaryl is optionally substituted with one or more $R^4$ independently.

In a further embodiment of the compounds of group A, B and C, $R^1$ is C=O or aryl optionally substituted with one or more $R^4$ independently.

In a further embodiment of the compounds of group A, B and C, $R^1$ is aryl optionally substituted with one or more $R^4$ independently.

In a further embodiment of the compounds of group A, B and C, $R^1$ is aryl.

In a further embodiment of the compounds of group A, B and C, $R^1$ is phenyl.

In a further embodiment of the compounds of group A, B and C, $R^2$ is H; $C_1$–$C_7$ alkyl; $C_2$–$C_7$ alkenyl; $C_2$–$C_7$ alkynyl; $C_3$–$C_7$ cycloalkyl; $C_3$–$C_7$ cycloheteroalkyl; aryl; heteroaryl; cyano; halogen; hydroxy, nitro; —SH; —SR$^5$; —SOR$^5$; —SO$_2$R$^5$; —CO$_2$R$^4$; $C_1$–$C_{10}$ alkyloxy; $C_2$–$C_{10}$ alkenyloxy; $C_2$–$C_{10}$ alkynyloxy, wherein each alkyl, alkenyl, alkynyl, cycloalkyl, cycloheteroalkyl, aryl, heteroaryl, alkyloxy, alkenyloxy, or alkynyloxy is optionally substituted with one or more $R^{11}$ independently.

In a further embodiment of the compounds of group A, B and C, $R^2$ is H; $C_1$–$C_7$ alkyl; $C_3$–$C_7$ cycloheteroalkyl; aryl; cyano; halogen; nitro; —SR$^5$; —SO$_2$R$^5$; —CO$_2$R$^4$; or $C_1$–$C_{10}$ alkyloxy; wherein each alkyl, cycloheteroalkyl, aryl, or alkyloxy is optionally substituted with one or more $R^{11}$ independently.

In a further embodiment of the compounds of group A, B and C, $R^2$ is H; $C_1$–$C_7$ alkyl; $C_3$–$C_7$ cycloheteroalkyl; aryl; cyano; halogen; —CO$_2$R$^4$; or $C_1$–$C_{10}$ alkyloxy; wherein each alkyl, cycloheteroalkyl, aryl, or alkyloxy is optionally substituted with one or more $R^{11}$ independently.

In a further embodiment of the compounds of group A, B and C, $R^2$ is H; $C_1$–$C_7$ alkyl; cyano; halogen; or $C_1$–$C_{10}$ alkyloxy; wherein each alkyl or alkyloxy is optionally substituted with one or more $R^{11}$ independently.

In a further embodiment of the compounds of group A, B and C, $R^2$ is H; cyano or halogen.

In a further embodiment of the compounds of group A, B and C $R^2$ is H.

In a further embodiment of the compounds of group A and B, $R^3$ is H; $C_1$–$C_{10}$ alkyl; $C_2$–$C_{10}$ alkenyl; $C_2$–$C_{10}$ alkynyl; $C_3$–$C_7$ cycloalkyl; aryl; $C_1$–$C_{10}$alkyl-O—$C_1$–$C_5$alkyl; cyano; nitro; halogen; hydroxy; wherein each alkyl, alkenyl, alkynyl, cycloalkyl, aryl, or alkyl-O-alkyl is optionally substituted with one or more $R^{12}$ independently; two $R^3$ attached to the same carbon atom may form a Spiro system.

In a further embodiment of the compounds of group A and B, $R^3$ is H; $C_1$–$C_{10}$ alkyl; $C_1$–$C_{10}$alkyl-O—$C_1$–$C_5$alkyl; hydroxy; wherein alkyl or alkyl-O-alkyl is optionally substituted with one or more $R^{12}$ independently; two $R^3$ attached to the same carbon atom may form a Spiro system.

In a further embodiment of the compounds of group A and B, $R^3$ is H or $C_1$–$C_{10}$ alkyl optionally substituted with one or more $R^{12}$ independently; two $R^3$ attached to the same carbon atom may form a Spiro system.

In a further embodiment of the compounds of group A and B, $R^3$ is H or $C_1$–$C_{10}$ alkyl.

In a further embodiment of the compounds of group A and B, $R^3$ is methyl, ethyl, or isopropyl.

In a further embodiment of the compounds of group A and B, $R^3$ is H.

In a further embodiment of the compounds of group C, $R^3$ is $C_1$–$C_{10}$ alkyl; $C_2$–$C_{10}$ alkenyl; $C_2$–$C_{10}$ alkynyl; $C_3$–$C_7$ cycloalkyl; aryl; $C_1$–$C_{10}$ alkyl-O—$C_1$–$C_5$alkyl; cyano; nitro; halogen; hydroxy; wherein each alkyl, alkenyl, alkynyl, cycloalkyl, aryl, or alkyl-O-alkyl is optionally substituted with one or more $R^{12}$ independently; two $R^3$ attached to the same carbon atom may form a Spiro system.

In a further embodiment of the compounds of group C, $R^3$ is $C_1$–$C_{10}$ alkyl; $C_1$–$C_{10}$alkyl-O—$C_1$–$C_5$alkyl; hydroxy; wherein alkyl, or alkyl-O-alkyl is optionally substituted with one or more $R^{12}$ independently; two $R^3$ attached to the same carbon atom may form a Spiro system.

In a further embodiment of the compounds of group C, $R^3$ is $C_1$–$C_{10}$ alkyl optionally substituted with one or more $R^{12}$ independently; two $R^3$ attached to the same carbon atom may form a Spiro system.

In a further embodiment of the compounds of group C, $R^3$ is $C_1$–$C_{10}$ alkyl.

In a further embodiment of the compounds of group C, $R^3$ is methyl, ethyl, or isopropyl In a further embodiment of the compounds of group A, B and C, $R^4$ is $C_1$–$C_{10}$ alkyl; $C_2$–$C_{10}$ alkenyl; $C_2$–$C_{10}$ alkynyl; $C_3$–$C_7$ cycloalkyl; aryl; heteroaryl; cyano; halogen; hydroxy, nitro; wherein each alkyl, alkenyl, alkynyl, cycloalkyl, aryl, or heteroaryl is optionally substituted with one or more $R^8$ independently.

In a further embodiment of the compounds of group A, B and C, $R^4$ is $C_1$–$C_{10}$ alkyl; $C_2$–$C_{10}$ alkenyl; or $C_2$–$C_{10}$alkynyl; wherein each alkyl, alkenyl, or alkynyl is optionally substituted with one or more $R^8$ independently.

In a further embodiment of the compounds of group A, B and C, $R^4$ is $C_1$–$C_{10}$ alkyl optionally substituted with one or more $R^8$ independently.

In a further embodiment of the compounds of group A, B and C, $R^4$ is $C_1$–$C_{10}$ alkyl.

In a further embodiment of the compounds of group A, B and C, $R^4$ is methyl.

In a further embodiment of the compounds of group A, B and C, $R^5$ is H; $C_1$–$C_{10}$ alkyl $C_2$–$C_{10}$ alkenyl; $C_2$–$C_{10}$ alkynyl; $C_3$–$C_7$ cycloalkyl; aryl; heteroaryl; wherein each alkyl, alkenyl, alkynyl, cycloalkyl, aryl, or heteroaryl-is optionally substituted with one or more $R^{14}$ independently.

In a further embodiment of the compounds of group A, B and C, $R^5$ is $C_1$–$C_{10}$ alkyl or aryl; wherein each alkyl or aryl is optionally substituted with one or more $R^{14}$ independently.

In a further embodiment of the compounds of group A, B and C, $R^6$ is H; $C_1$–$C_{10}$ alkyl; $C_2$–$C_{10}$alkenyl; $C_2$–$C_{10}$alkynyl; $C_3$–$C_7$ cycloalkyl; or aryl; wherein each each alkyl, alkenyl, alkynyl, cycloalkyl, or aryl is optionally substituted with one or more $R^{15}$ independently.

In a further embodiment of the compounds of group A, B and C, $R^6$ is H; $C_1$–$C_{10}$ alkyl; or $C_2$–$C_{10}$ alkenyl; wherein each each alkyl or alkenyl is optionally substituted with one or more $R^{15}$ independently.

In a further embodiment of the compounds of group A, B and C, $R^6$ is H or $C_1$–$C_{10}$ alkyl optionally substituted with one or more $R^{15}$ independently.

In a further embodiment of the compounds of group A, B and C, $R^6$ is H.

In a further embodiment of the compounds of group A, B and C, $R^6$ is $C_1$–$C_{10}$ alkyl optionally substituted with one or more $R^{15}$ independently.

In a further embodiment of the compounds of group A, B and C, $R^6$ is $C_1$–$C_{10}$ alkyl.

In a further embodiment of the compounds of group A, B and C, $R^6$ is methyl.

In a further embodiment of the compounds of group A, B and C, $R^7$ is H; $C_1$–$C_{10}$ alkyl; $C_2$–$C_{10}$alkenyl; or $C_2$–$C_{10}$alkynyl, wherein each each alkyl, alkenyl, or alkynyl is optionally substituted with one or more $R^{16}$ independently.

In a further embodiment of the compounds of group A, B and C, $R^7$ is $C_1$–$C_{10}$ alkyl optionally substituted with one or more $R^{16}$ independently.

In a further embodiment of the compounds of group A, B and C, $R^7$ is $C_1$–$C_{10}$ alkyl.

In a further embodiment of the compounds of group A, B and C, $R^8$ is —$OCH_3$.

In a further embodiment of the compounds of group A, B and C, $R^9$ is aryl.

In a further embodiment of the compounds of group A, B and C, $R^{11}$ is $C_1$–$C_{10}$ alkyl; aryl; cyano; halogen; wherein each alkyl or aryl is optionally substituted with one or more $R^8$ independently.

In a further embodiment of the compounds of group A, B and C, $R^{11}$ is halogen.

In a further embodiment of the compounds of group A, B and C, $R^{12}$ is $C_1$–$C_{10}$ alkyl; $C_2$–$C_{10}$ alkenyl; $C_2$–$C_{10}$ alkynyl; aryl; heteroaryl; cyano; halogen; hydroxy, nitro; wherein each alkyl, alkenyl, alkynyl, aryl, heteroaryl is optionally substituted with one or more $R^8$ independently.

In a further embodiment of the compounds of group A, B and C, $R^{12}$ is aryl; heteroaryl; or hydroxy; wherein each aryl and heteroaryl is optionally substituted with one or more $R^8$ independently.

In a further embodiment of the compounds of group A, B and C, $R^{12}$ is phenyl, pyridyl, or pyrrolidinyl.

In a further embodiment of the compounds of group A, B and C, $R^{12}$ is hydroxy.

In a further embodiment of the compounds of group A, B and C, $R^{14}$ is halogen.

A further aspect of the invention is a pharmaceutical composition comprising, as an active ingredient, at least one compound of the invention or a pharmaceutically acceptable salt or prodrug or hydrate thereof together with a pharmaceutically acceptable carrier or diluent.

A further aspect of the invention is the use of a compound of the invention for the manufacture of a medicament for treating diseases that are associated with proteins which are subject to inactivation by DPP-IV.

A further aspect of the invention is the use of a compound of the invention for the manufacture of a medicament for treatment of metabolic disorders.

A further aspect of the invention is the use of a compound of the invention for the manufacture of a medicament for blood glucose lowering.

A further aspect of the invention is the use of a compound of the invention for the manufacture of a medicament for treatment of Type 2 diabetes.

A further aspect of the invention is the use of a compound of the invention for the manufacture of a medicament for the treatment of impaired glucose tolerance (IGT).

A further aspect of the invention is the use of a compound of the invention for the, manufacture of a medicament for the treatment of impaired fasting glucose (IFG).

A further aspect of the invention is the use of a compound of the invention for the manufacture of a medicament for prevention of hyperglycemia.

A further aspect of the invention is the use of a compound of the invention for the manufacture of a medicament for delaying the progression of impaired glucose tolerance (IGT) to Type 2 diabetes.

A further aspect of the invention is the use of a compound of the invention for the manufacture of a medicament for delaying the progression of non-insulin requiring Type 2 diabetes to insulin requiring Type 2 diabetes A further aspect of the invention is the use of a compound of the invention for the manufacture of a medicament for increasing the number and/or the size of beta cells in a mammalian subject.

A further aspect of the invention is the use of a compound of the invention for the manufacture of a medicament for treatment of beta cell degeneration, in particular apoptosis of beta cells.

A further aspect of the invention is the use of a compound of the invention for the manufacture of a medicament for the treatment of disorders of food intake.

A further aspect of the invention is the use of a compound of the invention for the manufacture of a medicament for the treatment of obesity.

A further aspect of the invention is the use of a compound of the invention for the manufacture of a medicament for appetite regulation or induction of satiety.

A further aspect of the invention is the use of a compound of the invention for the manufacture of a medicament for the treatment of dyslipidemia.

A further aspect of the invention is the use of a compound of the invention for the manufacture of a medicament for treatment of functional dyspepsia, in particular irritable bowel syndrome.

A further aspect of the invention is a method for the treatment of diseases or disorders associated with proteins that are subject to inactivation by DPP-IV, the method comprising administering to a subject in need thereof an effective amount of a compound of the invention.

A further aspect of the invention is methods of treating the above mentioned diseases, the method comprising administering to a subject in need thereof an effective amount of a compound of the invention.

The compounds of the present invention may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in Journal of Pharmaceutical Science, 66, 2 (1977) which are known to the skilled artisan.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of this invention may form solvates with standard low molecular weight solvents using methods known to the skilled artisan.

It is to be understood that the invention extends to all of the stereo isomeric forms of the claimed compounds, as well as the racemates.

In the compounds of formula II, the bonds in the B-ring may be unsaturated, such that the B-ring is a five-membered or a six-membered carbocyclic or heterocyclic ring, which is fully unsaturated.

In a preferred embodiment of the compounds of formula II, $D^3$, $D^4$ and at least one $D^5$ are present, and $D^1$, $D^2$, $D^3$, $D^4$, and each $D^5$ may independently be a carbon, nitrogen, oxygen, or a sulfur atom; or C=O or C=S, and the bonds in the B-ring are unsaturated, such that the B-ring is a five-membered or a six-membered carbocyclic or heterocyclic ring, which is fully unsaturated.

When a D-ring is present in the compounds of formula II, the bonds in the D-ring are preferably unsaturated, such that the D-ring may be a five-membered or a six-membered carbocyclic or heterocyclic ring, which is fully unsaturated.

In the compounds of formula II, each $n_1$, $n_2$, may be one or two, independently $n_3$ is one, and $n_4$ is two, $D^1$ and $D^2$ may be carbon atoms, $D^4$ and one of the $D^5$ may be nitrogen atoms, and $D^3$ and the other $D^5$ may be C=O, or C=S, the bonds in the B-ring may be unsaturated, such that the B-ring is a five-membered carbocyclic or heterocyclic ring, which is fully unsaturated.

In particular, in the compounds of formula II, $n_1$ is two and each of $n_2$, $n_3$, $n_4$ is one or two, independently.

In a specific embodiment of the compound of formula II, the B-ring is a benzene ring each $n_1$, $n_2$, is one or two, independently, $D^3$, $D^4$, and $D^5$ are absent, such that $D^1$ and $D^2$ may each be optionally substituted with one $R^2$, independently.

Pharmaceutical Compositions

In another aspect, the present invention includes within its scope pharmaceutical compositions comprising, as an active ingredient, at least one compound of the invention which inhibits the enzymatic activity of DPP-IV or a pharmaceutically acceptable salt or prodrug or hydrate thereof together with a pharmaceutically acceptable carrier or diluent. Pharmaceutical compositions containing a compound of the invention of the present invention may be prepared by conventional techniques, e.g. as described in *Remington: The Science and Practise of Pharmacy, 19th Ed.,* 1995. The compositions may appear in conventional forms, for example capsules, tablets, aerosols, solutions, suspensions or topical applications.

Typical compositions include a compound of the invention which inhibits the enzymatic activity of DPP-IV or a pharmaceutically acceptable basic addition salt or prodrug or hydrate thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, dextrin, magnesium carbonate, sugar, cyclodextrin, amylose, magnesium stearate, talc, gelatine, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds. The route of administration may be any route, which effectively transports the active compound of the invention which inhibits the enzymatic activity of DPP-IV to the appropriate or desired site of action, such as oral, nasal, pulmonary, buccal, subdermal, intradermal, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the invention which inhibits the enzymatic activity of DPP-IV, dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
| --- | --- |
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of formula I and formula II may be administered to a mammal, especially a human in need of such treatment, prevention, elimination, alleviation or amelioration of the various diseases as mentioned above, e.g. metabolic disorders, Type 2 diabetes, hyperglycemia, impaired glucose tolerance (IGT), impaired fasting glucose (IFG), beta cell degeneration, apoptosis of beta cells, disorders of food intake, obesity, dyslipidemia, and functional dyspepsia, in particular irritable bowel syndrome. In particular, the compounds of formula I or formula II are contemplated to be useful for the prevention or treatment of Type 2 diabetes. Furthermore, the compounds of formula I or formula II may be useful for blood glucose lowering, prevention of hyperglycemia, delaying the progression of impaired glucose tolerance to Type 2 diabetes, delaying the progression of non-insulin requiring Type 2 diabetes to insulin requiring Type 2 diabetes, increasing the number and/or size of beta cells in a mammalian subject, or appetite regulation or induction of satiety. The mammal to be treated with a compound of formula I or formula II is preferably a human, but may also be an animal, both a domesticated animal, e.g. household pet, and non-domesticated animal such as wildlife.

The compounds of the invention are effective over a wide dosage range. For example, in the treatment of adult humans, dosages from about 0.05 to about 1000 mg, preferably from about 0.1 to about 500 mg, per day may be used. A most preferable dosage is about 0.5 mg to about 250 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.05 to about 1000 mg of active ingredient together with a pharmaceutically acceptable carrier per unit dosage.

Usually, dosage forms suitable for oral, nasal, pulmonal or transdermal administration comprise from about 0.05 mg to about 1000 mg, preferably from about 0.5 mg to about 250 mg of the compounds admixed with a pharmaceutically acceptable carrier or diluent. The invention also encompasses prodrugs of a compound of the invention which on administration undergo chemical conversion by metabolic processes before becoming active pharmacological substances. In general, such prodrugs will be functional derivatives of a compound at the invention which are readily convertible in vivo into a compound at the invention. Conventional procedures for the selection and preparation of suitable prodrug derivatives are described, for example, in "Design of Prodrugs", ed. H. Bundgaard, Elsevier, 1985.

The invention also encompasses active metabolites of a compound of the invention. The preparation of the compounds of formula I can be done in many ways. The starting materials are either known compounds or compounds which may be prepared in analogy with the preparation of similar known compounds. A particularly useful synthesis is outlined below.

Combination Treatments

The invention furthermore relates to the use of a compound according to the present invention for the preparation of a medicament for use in the treatment of diabetes in a regimen which additionally comprises treatment with another antidiabetic agent. In the present context the expression "antidiabetic agent" includes compounds for the treatment and/or prophylaxis of insulin resistance and diseases wherein insulin resistance is the pathophysiological mechanism.

In one embodiment of this invention, the antidiabetic agent is insulin or GLP-1 or any analogue or derivative thereof.

In another embodiment the antidiabetic agent is a hypoglycaemic agent, preferably an oral hypoglycaemic agent.

Oral hypoglycaemic agents are preferably selected from the group consisting of sulfonylureas, non-sulphonylurea insulin secretagogues, biguamides, thiazolidinediones, alpha glucosidase inhibitors, glucagon antagonists, GLP-1 agonists, potassium channel openers, insulin sensitizers, hepatic enzyme inhibitors, glucose uptake modulators, compounds modifying the lipid metabolism, compounds lowering food intake, and agents acting on the ATP-dependent potassium channel of the β-cells.

Among the sulfonylureas, tolbutamide, glibenclamide, glipizide and gliclazide are preferred.

Among the non-sulphonylurea insulin secretagogues, repaglinide and nateglinide are preferred.

Among the biguamides, metformin is preferred.

Among the thiazolidinediones, troglitazone, rosiglitazone and ciglitazone are preferred.

Among the glucosidase inhibitors, acarbose is preferred.

Among the agents acting on the ATP-dependent potassium channel of the β-cells the following are preferred: glibenclamide, glipizide, gliciazide, repaglinide.

Examples from the literature of known compounds which are included in formula II are listed in Table 1 along with their Beilstein and CAS registry numbers. The synthesis methods disclosed in these references for producing compounds of general formula II are incorporated herein by reference.

TABLE 1

| Structure | Beilstein registry number | CAS registry number |
|---|---|---|
| 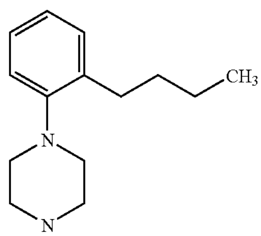 | 521102 | 100861-48-1 |
| 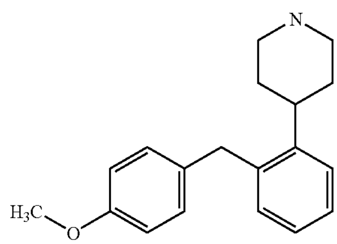 | 1543395 | 77597-74-1 |
| 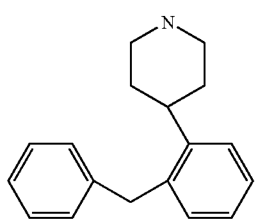 | 1685814 | 77597-48-9 |
| 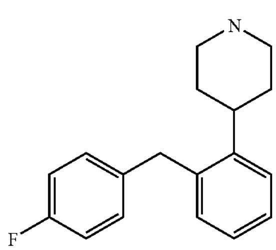 | 1687023 | 77597-75-2 |

TABLE 1-continued
| Structure | Beilstein registry number | CAS registry number |
|---|---|---|
| 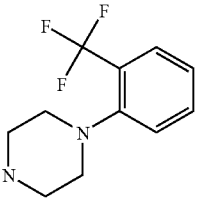 | 4189427 | 63854-31-9 |
| 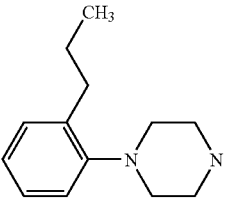 | 4865281 | 119695-81-7 |
| 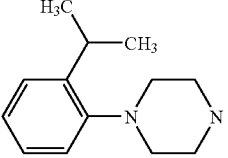 | 4865461 | 119695-82-8 |
| 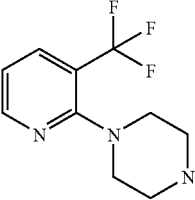 | 5667444 | 87394-50-1 |
| 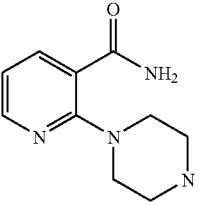 | 5745673 | 87394-64-7 |
| 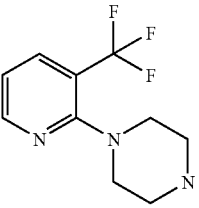 | 5749933 | 87394-63-6 |
| 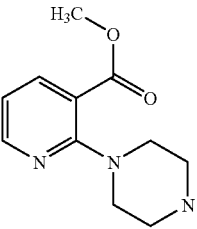 | 6510974 | 104813-92-5 |

TABLE 1-continued

| Structure | Beilstein registry number | CAS registry number |
|---|---|---|
| 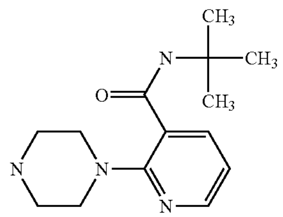 | 6811251 | |
| 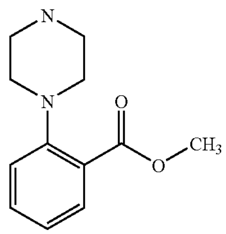 | 6924778 | |
| 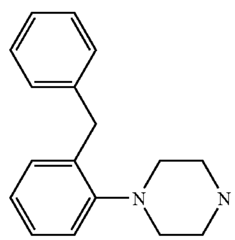 | 7815919 | |
| 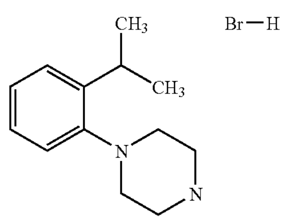 | 7835655 | |
| 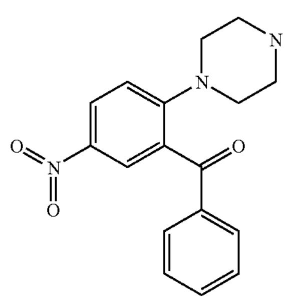 | 7884424 | |
| 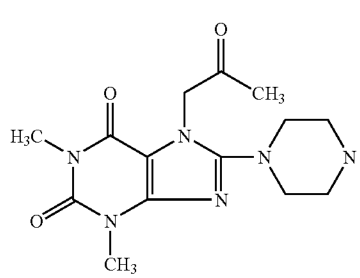 | 1174841 | 24961-80-6 |

TABLE 1-continued

| Structure | Beilstein registry number | CAS registry number |
|---|---|---|
| [structure] | 1235399 | 20367-10-6 |
| [structure] | 4698427 | 110963-63-8 |
| [structure] | 5784284 | |
| [structure] | 6066512 | 87233-69-0 |
| [structure] | 7644451 | |
| [structure] | 7651816 | |

TABLE 1-continued

| Structure | Beilstein registry number | CAS registry number |
|---|---|---|
| (5-methyl-1-benzyl-2-piperazin-1-yl-benzimidazole) | 7653876 | |
| (5-hydroxy-1-benzyl-2-piperazin-1-yl-benzimidazole) | 7655222 | |
| (5-chloro-1-benzyl-2-piperazin-1-yl-benzimidazole) | 7655225 | |
| (5,6-dimethyl-1-benzyl-2-piperazin-1-yl-benzimidazole) | 7656178 | |
| (6-methoxy-1-benzyl-2-piperazin-1-yl-benzimidazole) | 7657431 | |
| (7-methoxy-1-benzyl-2-piperazin-1-yl-benzimidazole) | 7658569 | |

TABLE 1-continued

| Structure | Beilstein registry number | CAS registry number |
|---|---|---|
| 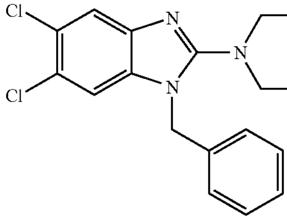 | 7659390 | |
| 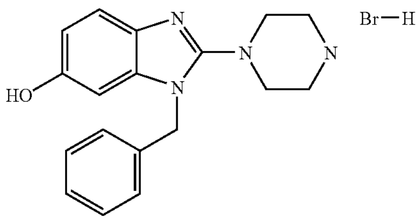 | 7675354 | |

Examples from the literature of the B-D ring systems of compounds of formula II shown here with only methyl or amino substituents for simplicity, includes the compounds shown in Table 2. The synthesis methods disclosed in the corresponding references for obtaining these and structurally similar compounds are incorporated herein by reference. These compounds will enable the skilled person to produce derived compounds within the scope of formula II by utilizing common general knowledge and/or the synthesis methods disclosed above.

TABLE 2

| Structure | Beilstein Number | CAS number |
|---|---|---|
| 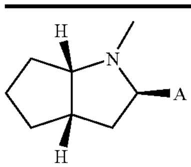 | 1238 | 74195-76-9 |
| 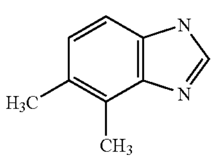 | 4194 | 69557-55-7 |
| 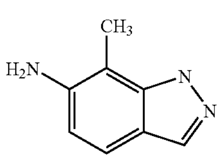 | 5023 | |
| 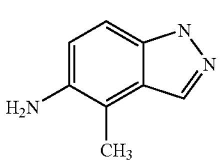 | 5155 | 101257-89-0 |

TABLE 2-continued

| Structure | Beilstein Number | CAS number |
|---|---|---|
| 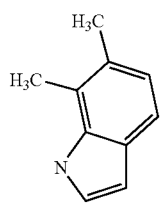 | 116537 | 55199-24-1 |
| 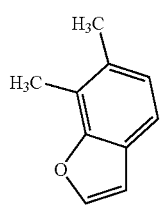 | 116538 | 35355-36-3 |
| 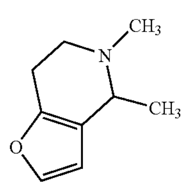 | 122537 | |
| 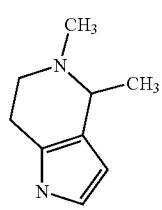 | 122538 | |

TABLE 2-continued
| Structure | Beilstein Number | CAS number |
|---|---|---|
| 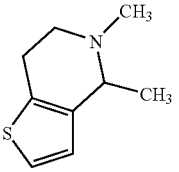 | 122542 | |
| 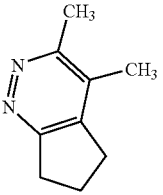 | 127514 | 109510-86-3 |
| 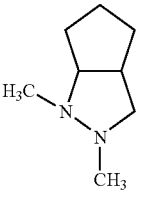 | 506507 | 24659-45-8 |
| 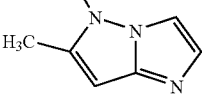 | 509993 | 70786-21-9 |
| 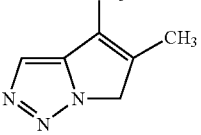 | 510908 | 64804-01-9 |
| 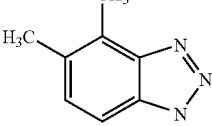 | 511008 | 35899-34-4 |
| 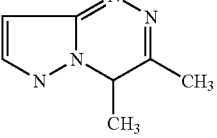 | 513137 | 6726-50-7 |
| 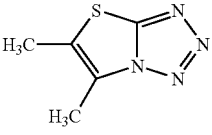 | 880387 | 19949-03-2 |
| 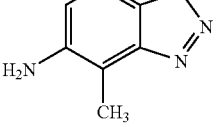 | 908493 | |
| 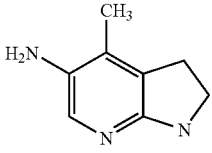 | 909190 | 59558-44-0 |
| 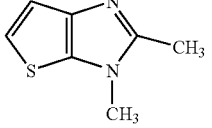 | 972126 | 71309-37-0 |
| 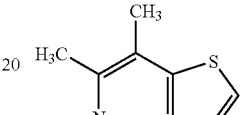 | 972323 | 56857-06-8 |
| 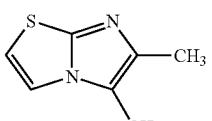 | 972468 | 23576-87-6 |
| 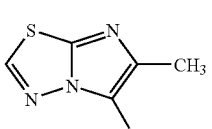 | 973539 | 57772-01-7 |
| 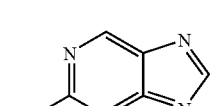 | 975944 | |
| 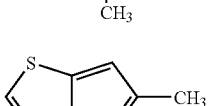 | 1072661 | 1194-70-3 |
| 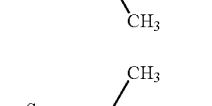 | 1072837 | 1123-57-5 |
| 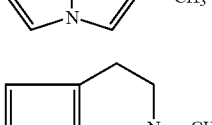 | 1101453 | 45859-46-9 |
| 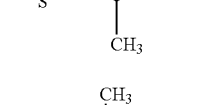 | 1105223 | 61262-26-8 |

TABLE 2-continued

| Structure | Beilstein Number | CAS number |
|---|---|---|
| (CH3, H3C, triazolopyridazine) | 1105319 | 61262-27-9 |
| (thienopyridine with H3C, CH3) | 1210589 | 56857-07-9 |
| (dimethyl benzothiophene) | 1281990 | 37610-98-3 |
| (dimethyl dihydropyrrolizine) | 1635988 | 38828-73-8 |
| (dimethyl indole) | 1636056 | 27866-47-3 |
| (dimethyl bicyclopentane) | 1919015 | 33430-55-6; 33430-56-7; 33430-87-4; 33507-44-7; 56579-34-1; 56579-40-9; 56579-41-0 |
| (dimethyl cyclopentene-fused) | 2038630 | 35408-32-3 |
| (trimethyl cyclopentadiene-fused) | 2235602 | 53356-67-5 |
| (dimethyl indene) | 2239113 | 23288-07-5 |

TABLE 2-continued

| Structure | Beilstein Number | CAS number |
|---|---|---|
| (tricyclic dimethyl with stereochemistry) | 2498411 | |
| (tricyclic dimethyl isomer) | 2498412 | |
| (dimethyl indane) | 2553303 | 1685-83-2 |
| (dimethyl pyrrolotetrazole) | 3541426 | 123810-45-7 |
| (dimethyl tetrahydroisoquinoline) | 4384604 | 83458-55-3 |
| (methyl pyrrolopiperazine) | 4668109 | 73627-19-7 |
| (dimethyl tetrahydrobenzothiophene) | 4966975 | 81795-09-7 |
| (dimethyl tetrahydrobenzothiophene isomer) | 4967113 | 81795-08-6 |
| (dimethyl benzofuran) | 4967423 | 97457-29-9 |

TABLE 2-continued

| Structure | Beilstein Number | CAS number |
|---|---|---|
| (structure) | 5239811 | 126441-87-0; 126575-73-3 |
| (structure) | 5239812 | 126441-87-0; 126575-73-3 |
| (structure) | 5248212 | 81795-10-0 |
| (structure) | 5253837 | |
| (structure) | 5499944 | 107970-21-8 |
| (structure) | 6134939 | |
| (structure) | 6193509 | |
| (structure) | 6474743 | |
| (structure) | 6474744 | |
| (structure) | 7421534 | |
| (structure) | 7914160 | |

Methods for Measuring the Activity of Compounds which Inhibit the Enzymatic Activity of CD26/DPP-IV

SUMMARY

Chemical compounds are tested for their ability to inhibit the enzyme activity of purified CD26/DPP-IV. Briefly, the activity of CD26/DPP-IV is measured in vitro by its ability to cleave the synthetic substrate Gly-Pro-p-nitroanilide (Gly-Pro-pNA). Cleavage of Gly-Pro-pNA by DPP-IV liberates the product p-nitroanilide (pNA), whose rate of appearance is directly proportional to the enzyme activity. Inhibition of the enzyme activity by specific enzyme inhibitors slows down the generation of pNA. Stronger interaction between an inhibitor and the enzyme results in a slower rate of generation of pNA. Thus, the degree of inhibition of the rate of accumulation of pNA is a direct measure of the strength of enzyme inhibition. The accumulation of pNA is measured spectrophotometrically. The inhibition constant, Ki, for each compound is determined by incubating fixed amounts of enzyme with several different-concentrations of inhibitor and substrate.

Materials

The following reagents and cells are commercially available:
Porcine CD26/DPP-IV (Sigma D-7052), Gly-Pro-pNA (Sigma G0513).
Assay buffer: 50 mM Tris pH 7.4, 150 mM NaCl, 0,1% Triton X-100.

Gly-Pro-pNA Cleavage-assay for CD26

The activity of purified CD26/DPP-IV is assayed in reactions containing:
70 µl assay buffer
10 µl inhibitor or buffer
10 µl substrate (Gly-Pro-pNA from a 0.1M stock solution in water) or buffer
10 µl enzyme or buffer Reactions containing identical amounts of enzyme, but varying concentrations of inhibitor and substrate, or buffer as control, are set up in parallel in individual wells of a 96-well ELISA plate. The plate is incubated at 25° C. and absorbance is read at 405 nm after 60 min incubation. The inhibitorrconstants are calculated by nonlinear regression hyperbolic fit and the result is expressed as inhibition constant (Ki) in nM.

Diabetes Model

The Zucker Diabetic Fatty (ZDF) rat model can be used to investigate the effects of the compounds of the invention on both the treatment and prevention of diabetes as rats of this sub-strain are initially pre-diabetic although develop severe type 2 diabetes characterised by increased HbA1 c levels over a period of 6 weeks. The same strain can be used to predict the clinical-efficacy of other anti-diabetic drug types. For example, the model predicts the potency and limited clinical efficacy of thiazolidinedione insulin sensitiser compounds.

EXAMPLES

A further detailed description of the invention is given with reference to the following examples.

Preparative HPLC (Method A1)

Column: Waters Radial compression column Prep Nova-Pak c18 25×100, plus a Waters Prep NovaPak HR c18 25×10 precolumn, in a Waters PrepLC 25×100 compression module housing. Buffer: linear gradient 5–95% in 15 min, MeCN, 0.1% TFA, flow rate of 15 ml/min. The pooled fractions are either evaporated to dryness in vacuo, or evaporated in vacuo until the MeCN is removed, and then frozen and freeze dried.

Preparative HPLC (Method A2)

Column: 1.9×15 cm Waters XTerra RP-18. Buffer: linear gradient 5–95% in 15 min, MeCN, 0.1% TFA, flow rate of 15 ml/min. The pooled fractions are either evaporated to dryness in vacuo, or evaporated in vacuo until the MeCN is removed, and then frozen and freeze dried.

Preparative HPLC (Method A3)

Column: Supelcosil ABZ+Plus, 25 cm×10 mm, 5 µm. Solvent A: 0.1% TFA/Water, solvent B: MeCN. Eluent composition: 5 min. 100% A, linear gradient 0–100% B in 7 min, 100% B in 2 min. Flow rate 5 ml/min. The column is allowed to equilibrate for 4 min in 100% A before the next run.

HPLC-MS (Method B)

Column: Waters Xterra MS C-18×3 mm id. Buffer: Linear gradient 10%-100% in 7.5 min, MeCN, 0.01% TFA, flow rate 1.0 ml/min. Detection 210 nm (analog output from diode array detector), MS-detection ionisation mode API-ES, scan 100–1000 amu step 0.1 amu.

HPLC-MS (Method C)

The following instrumentation was used:
Sciex API 100 Single quadropole mass spectrometer
Perkin Elmer Series 200 Quard pump
Perkin Elmer Series 200 autosampler
Applied Biosystems 785A UV detector
Sedex 55 evaporative light scattering detector
A Valco column switch with a Valco actuator controlled by timed events from the pump.

The Sciex Sample control software running on a Macintosh PowerPC 7200 computer was used for the instrument control and data acquisition.

The HPLC pump was connected to four eluent reservoirs containing:
A: Acetonitrile
B: Water
C: 0.5% TFA in water
D: 0.02 M ammonium acetate The requirements for samples are that they contain approximately 500 fig/ml of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis was performed at room temperature by injecting 20 µL of the sample solution on the column, which was eluted with a gradient of acetonitrile in either 0.05% TFA or 0.002 M ammonium acetate. Depending on the analysis method varying elution conditions were used.

The eluate from the column was passed through a flow splitting T-connector, which passed approximately 20 µL/min (1/50) through approx. 1 m. 75µ fused silica capillary to the API interface of API 100 spectrometer.

The remaining 1.48 ml/min (49/50) was passed through the UV detector and to the ELS detector.

During the LC-analysis the detection data were acquired concurrently from the mass spectrometer, the UV detector and the ELS detector.

The LC conditions, detector settings and mass spectrometer settings used for the different methods are given in the following tables.

| Column | Waters Symmetry $C_{18}$ 3 mm × 150 mm |
| --- | --- |
| Gradient | 5%–90% acetonitrile in 0.05% TFA linearly during 15 min at 1 ml/min |
| Detection | UV: 214 nm ELS: 40° C. |
| MS | Experiment: Start: 100 amu Stop: 800 amu Step: 0.2 amu |
|  | Dwell: 0.571 msec |
|  | Method: Scan 284 times = 9.5 min |

Analytical HPLC (Method D)

Column 2.4×20 cm RP18. Buffer pH=3.0 ($H_3PO_4$), Acetonitrile. Flow rate 1.0 ml/min. UV detection. Merck Hitachi system.

General Piperazine Synthesis Procedure I

The procedure is described in *Synthesis;* 3; 1984; 271–274; *Synthesis;* 12; 1981; 969–971. *Synthesis;* 10; 1982; 861–864. *Synthesis;* 4; 1991; 318–319

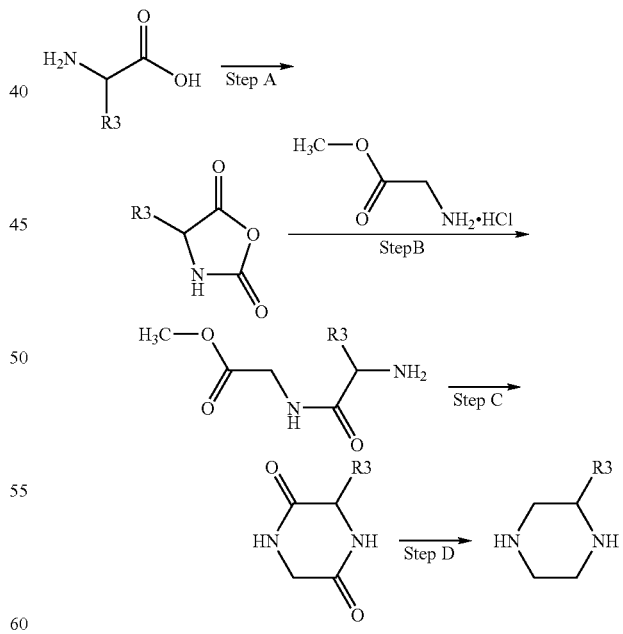

Step A: Preparation of Oxazolidine-2,5-dione Derivatives

The amino acid (25.6 mol) was slurried in THF (100 ml) phosgene (20% in toluene) (3.05 g; 30.8 mmol) was added. The reaction mixture was stirred at room temperature for 15 hours. The reaction mixture was evaporated in vacuo. The title compound precipitated as white crystals. The product was used without any further purification.

Step B: Preparation of (2-Amino-propionylamino) Acetic Acid Methyl Ester Derivatives The above oxazolidine-2,5-dione derivative (27.1 mmol) dissolved in THF (50 ml) was added a slurry of glycine methyl ester hydrochloride (3.75 g; 29.9 mmol) and TEA- (7.4 g; 73.3 mmol) in DCM (50 ml) at 0° C. The reaction mixture was allowed to warm up to room temperature and was stirred for 15 hours. The mixture was filtered (TEA, HCl) and the reminisce was evaporated in vacuo giving an oil. The product was used without any further purification.

Step C: Preparation of Piperazine-2,5-dione Derivatives

The above (2-Amino-propionylamino) acetic acid methyl ester derivative (28.6 mmol) was slurred in xylene (200 ml) and refluxed (140° C.) for 96 hours. A crude blackish crystalline material was filtered of. The crystals was recrystallised from methanol and charcoal giving the title compound as white crystals.

Step D: Preparation of Piperazine Derivatives

The above piperazine-2,5-dione derivative (1.1 mmol) was dissolved in THF (100 ml). LiAlH$_4$ was added in small portions under N$_2$. The reaction mixture was stirred for 15 hours at 70° C. Water was added dropwise until the mixture was white. K$_2$CO$_3$ was added until the mixture had a filterable consistence. The mixture was filtered evaporated in vacuo giving the title compound as an oil.

General Piperazine Synthesis Procedure II

Step E and F are described in *J. Org. Chem.* 50 (24); 1985; 4796–4799 while step D is as described above.

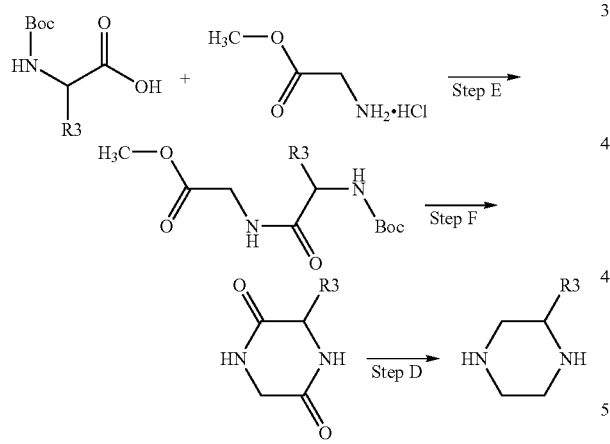

Step E: Preparation of t-Boc-dipeptide Esters

The t-Boc-amino acid (9.4 mmol) was dissolved in dry DCM (25 ml) and 1-hydroxybenzotriazol (9.6 mmol) and 1-ethyl-3-(3-dimethylaminopropyl)carbodiimide hydrochoride (9.9 mmol) were added at 0–5° C. Stirring was continued for ½ hour after which the amino acid methyl ester hydrochloride (10.3 mmol) and TEA (10.7 mmol) were added at 0–5° C. The reaction mixture was stirred at room temperature overnight. The mixture was poured into 0.5 M potassium hydrogensulphate (50 ml) and filtered. The organic phase was isolated and washed with 10% aqueous sodium hydrogencarbonate (2×20 ml) and brine (1×20 ml), dried over magnesium sulphate and evaporated in vauco. The product was used without further purification.

Step F: Preparation of 2,5-diketopiperazines

The t-Boc-dipeptide methyl ester (11.6 mmol) was dissolved in formic acid (60 ml) and stirred at room temperature for 2½ hours. The solvent was removed at 35° C. under high vacuum and the crude dipeptide ester formate was dissolved in a mixture of dry sec-butyl alcohol (24 ml) and dry toluene (12 ml). The solution was refluxed for 2 hours. After approx. one hour the diketopiperazine start to crystallize out of the hot reaction. The reaction mixture was cooled to 0–5 IC and the white crystals of diketopiperazine was isolated by filtration.

Abbreviations

| | |
|---|---|
| DCM | Dichloromethane |
| DIEA | Diisopropylethylamine |
| DMF | Dimethylformamide |
| DMSO | Dimethyl sulfoxide |
| HOAc | Acetic acid |
| MeCN | Acetonitrile |
| TFA | Trifluoroacetic acid |
| THF | Tetrahydrofurane |
| TMG | Tetramethylguanidine |

General Procedure (A)

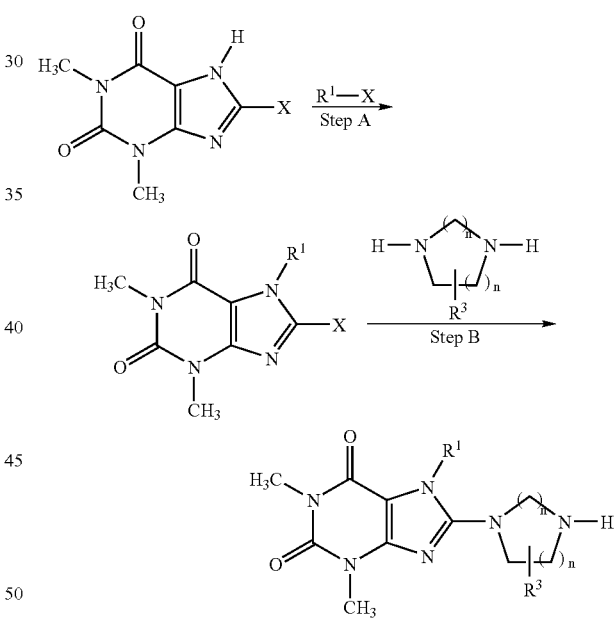

$R^1$, $R^3$, X and n are defined as in formula II.

Step A

8-Chloro-1,3-dimethyl-3,7-dihydro-purine-2,6-dione (Avocado, UK) (0.2 g; 0.93 mmol) and the arylmethylhalogenide (0.93 mmol) K$_2$CO3 (0.257 g; 18, 6 mmol) and DMF (5 ml) is mixed in a scintillations vessel (20 ml). The vessels are carefully sealed and the reaction mixtures are shaken for 121 hours at 100° C. After cooling, brine (5 ml) and ethyl acetate (5 ml) is added. The reaction mixtures are shaken for 10 hours. The ethyl acetate phase is decanted to a new scintillations vessel. The water/DMF-phase is then extracted with DCM (5 ml). The DCM and ethyl acetate phase are combined and evaporated in a speedvac. The residue is used without any purification in the next step.

Step B

8-Chloro-7-(arylmethyl)-1,3-dimethyl-3,7-dihydro-purine-2,6-dione derivative (50 mg, ~0.15 mmol) is dissolved in methoxyethanol (1 ml) in a 4 ml scintillation vessel. The piperazine derivative (0.235 mmol), and TEA (32 mg; 43 µL; 0.31 mmol) are added. The vessels are sealed carefully and shaken for 7 days at 100 Co. The reaction mixtures are evaporated in a speedvac. Each vessel is added methanol (1 ml), and 1 N HCl (0.5 ml), shaken for 10 hours and evaporated in a speedvac. The samples are purified by prep. HPLC (Method A1).

The purified compounds are analysed by LC-MS.

General Procedure (B)

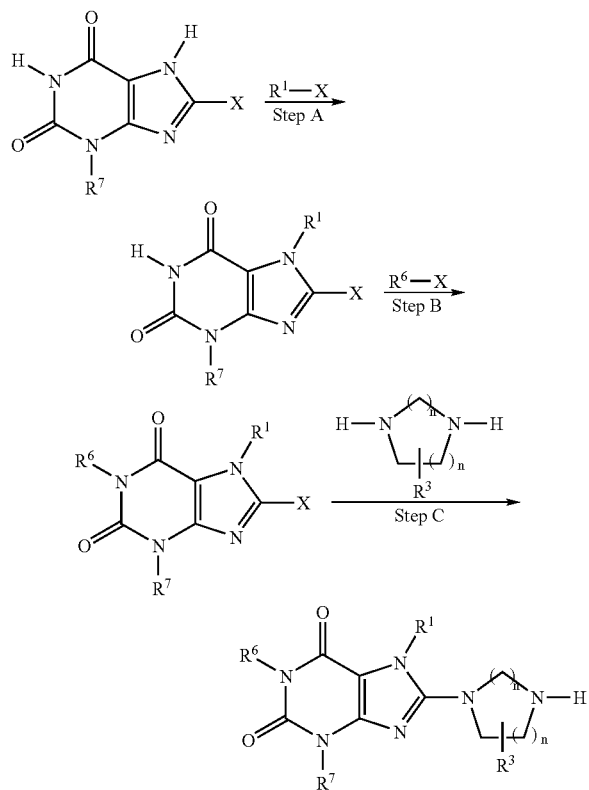

$R^1$, $R^3$, $R^6$, $R^7$, X and n are defined as in formula I.

Step A

The starting material 3-benzyl-8-bromo-3,7-dihydro-purine-2,6-dione or 3-methyl-8-bromo-3,7-dihydro-purine-2,6-dione (16 mmol) is dissolved in a mixture of DMF and DIEA (3% DI EA, 250 µL). Substituted benzyl bromide or other alkylating agents (16.8 umo!, 1.05 equiv) are dissolved in DMF (100 µL) and added. The mixture is heated to 65° C. for 2 h.

Step B

Alkylation reagent $R^6$—X (32 µmol) is dissolved in DMF (100 µl) and added to the above reaction mixture, followed by a solution of TMG in DMF (1.16 ml TMG diluted to 5.8 ml, 48 ul). The mixture is kept at 65° C. for 4 h.

Step C

Diamine (200 mmol) is dissolved in a mixture of DMF and DIEA (3% DIEA, 200 µL) and added to the above reaction mixture. The reaction is kept at 65° C. for 1–4d.

Samples are neutralized using HOAC (20 pi). The solvent is evaporated and the residue is dissolved in DMSO/H$_2$O (4:1, 500 µl) and purified by HPLC (Method A3)

General Procedure (C)

Step A:

The first reaction step is identical to Step A in general procedure (A)

Step B:

8-Chloro-7-(arylmethyl)-1,3-dimethyl-3,7-dihydro-purine-2,6-dione derivative (1 eq.), piperazine (3 eq.) and TEA (5 eq) is heated in an appropriate solvent in a closed vessel in a micro wave oven (CEM MARSX microwave instrument. Magnetron frequency: 2455 MHz. Power Output: 1200 Watt.) at 15° C. for 4 hours. The reaction mixture is cooled and evaporated in vacuo. The remaining oil is purified on a silica gel column with DCM/MeOH (3:1) as eluent, giving the title compound as an oil. The oil may be dissolved in DCM to afford the hydrochloride salt upon addition of hydrochloride in ether. Alternatively, the samples may be purified by prep. HPLC (Method A2). The purified compounds are analysed by LC-MS. All reactions are performed in closed vessels: XP 1500 Plus Vessel set; at a given temperature in an appropriate solvent. Normally solvents like MeOH; EtOH, iPrOH; H$_2$O; DMF and DMSO are used.

General procedure (D)

Step A: The first reaction step is identical to Step A in general procedure (A)

Step B:

8-Chloro-7-(arylmethyl)-1,3-dimethyl-3,7-dihydro-purine-2,6-dione derivative (1.64 mmol), amine (2.39 mmol) and potassium carbonate (2.4 mmol) was heated in DMF (30 ml) at 100° C. for 5 hours. The reaction mixture was cooled to room temperature and filtered. The filtrate was evaporated to dryness in vacuo and the residue was purified on a silica gel column (Eluent: Ethyl acetate/Methanol/Triethylamine (90:10:2)) giving the pure base. The hydrochloride salt may be prepared by dissolving the base in isopropanol and adding hydrogen chloride in diethyl ether to the solution.

General Procedure (E): Preparation of 6-substituted-[1,4]-diazepanes

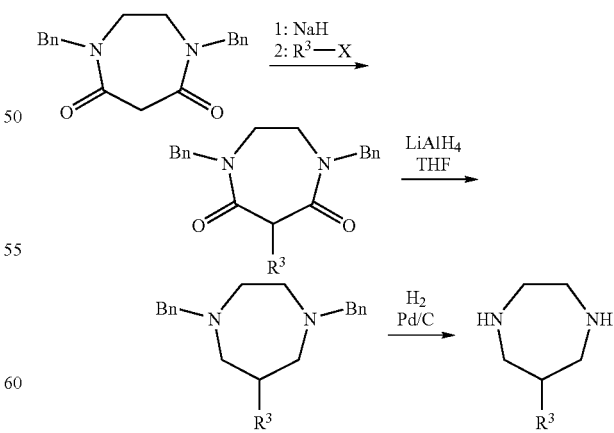

1,4-Dibenzyl-[1,4]diazepane-5,7-dione is converted to the Na-salt in THF with NaH as base, and reacted with the $R^3$—X alkylating reagent e.g. benzyl bromide, at room temperature. The product e.g. 1,4,6-Tribenzyl-[1,4]diazepane-5,7-dione is reduced to the 1,4,6-Tribenzyl-[1,4]diazepane by treatment with LiAlH4 in THF at elevated temperature. The N-benzyl groups are removed by catalytic hydrogenation in EtOH:AcOH (1:1), using Pd/C as catalyst.

Example 1

7-Benzyl-8-(6-hydroxymethyl-[1,4]diazepan-1-yl)-1,3-dimethyl-3,7-dihydropurine-2,6-dione. TFA

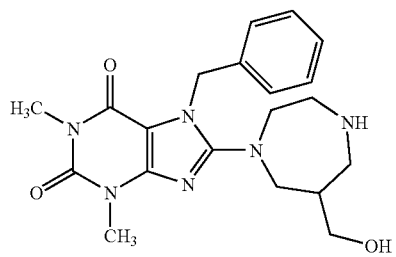

Step A: Preparation of 1,4-dibenzyl-[1,4]diazepane-6-carboxylic Acid. Na-salt (1A)

N,N'-dibenzylethylenediamine (4.9 ml, 20.8 mmol) was dissolved in toluene (200 ml), triethylamine (8.94 ml, 64.5 mmol), and methanol (20 ml) and 3-bromo-2-bromomethylpropionic acid (5.12 g, 20.8 mmol) was added. The reaction mixture was heated to reflux for 24 hours. The solvents were evaporated and the remaining was redissolved in water (150 ml) and ethyl acetate (150 ml). The aqueous layer was acidified with 6N hydrochloric acid until pH=2, and the layers were separated. The aqueous layer was washed with ethyl acetate and then 10% aqueous sodium hydroxide was added until pH=12. The aqueous layer was washed with 4×150 ml of ethyl acetate, and then evaporated to dryness. The remaining was suspended in ethyl acetate (200 ml) and dry methanol (20 ml) and salts was filtered off. The mother liquor was evaporated and purified by chromatography on silica, using 10% methanol in dichloromethane as the eluent. Fractions containing the product were evaporated, to afford 5.09 g of 1A as an yellow foam in 70% yield.

$^1$H-NMR (CDCl$_3$): δ 7.31 (10H, m); 3.78 (4H, m); 3.18 (4H, m); 2.81 (3H, m); 2.58 (2H, m).

HPLC-MS (Method B): m/z 325 (M+1); R$_t$=1.55 min.

Step B: Preparation of (1,4-dibenzyl-[1,4]diazepan-6-yl)methanol (1B)

The sodium salt of 1,4-dibenzyl-[1,4]diazepane-6-carboxylic acid (1 A) (2.36 g, 6.81 mmol) was dissolved in dry tetrahydrofuran (50 ml) under a nitrogen atmosphere and lithium aluminium hydride (0.50 g, 13.6 mmol) was added. The reaction mixture was stirred at room temperature for 2 hours and then quenched with water until effervescence ceases. Ethyl acetate (200 ml) and solid potassium carbonate was added until a white suspension appeared, and the mixture was allowed to stir for half an hour. The suspension was filtered through celite, which was washed with 3×50 ml of ethyl acetate. Water (200 ml) was added and the aqueous layer was extracted with 3×200 ml of ethyl acetate. The combined organic layers were washed with brine and dried over sodium sulfate. The solvent was evaporated to afford 2.06 g of 1 B as an yellow oil in 97% yield.

$^1$H-NMR (CDCl$_3$): δ 7.28 (10H, m); 3.61 (4H, s); 3.55 (2H, d); 2.99 (2H, dd); 2.73 (2H, dd); 2.57 (4H, m); 1.93 (1H, m).

HPLC-MS (Method B): m/z=311 (M+1); R$_t$=1.24 min.

Step C: Preparation of ([1,4]diazepan-6-yl)methanol (1C)

(1,4-Dibenzyl-[1,4]diazepan-6-yl)methanol (1 B) (1.02 g, 3.28 mmol) was dissolved in ethanol (50 ml) and acetic acid (8 ml) and palladium, 10 wt. % on activated carbon (0.2 g) was added. The mixture was hydrogenated on a Parr apparatus at 45 psi. for 6 days, and filtered twice. The solvents were evaporated and the crude product was dissolved in water (2 ml) and saturated potassium carbonate was added until pH=13. The aqueous layer was washed with 4×10 ml of ethyl acetate, and water was evaporated. The crude product was purified by preparative HPLC (method Al; R$_t$=2.27 min.) to afford 5.3 g of 1 C including potassium carbonate salt.

HPLC-MS (Method B): m/z=131 (M+1); R$_t$=0.33 min.

Step D: Preparation of 7-benzyl-8-(6-hydroxymethyl-[1,4]diazepan-1-yl)-1,3-dimethyl-3,7-dihydropurine-2,6-dione. TFA (1)

([1,4]Diazepan-6-yl)methanol (1C) including potassium carbonate salts (ca 1 mmol) was suspended in dry DMF (200 ml) and 7-benzyl-8-chloro-1,3-dimethyl-3,7-dihydro-purine-2,6-dione (199.9 mg, 0.656 mmol) and potassium carbonate (453 mg, 3.28 mmol) were added. The reaction mixture was stirred at room temperature for 24 hours, heated to 60° C. for 3 hours, heated to 95° C. for 5 hours and heated to 120° C. for 2 hours. The suspension was allowed to cool to room temperature and white salts were filtered off. The filtrate was evaporated and purified by chromatography on silica, using 5% methanol in dichloromethane as the eluent. Fractions containing the product were evaporated and purified by preparative HPLC (method A2; R$_t$=2.52 min.) to afford 8 mg of the title compound as an yellow oil in 1% yield.

$^1$H-NMR (MeOH-d$_4$): δ 7.30 (3H, m); 7.14 (2H, d); 5.53 (2H, s); 3.80–3.05 (16H, m); 2.09 (1H, m). HPLC-MS (Method B): m/z=399 (M+1); R.=1.75 min.

Example 2

7-Benzyl-8-(6-hydroxy-[1,4]diazepan-1-yl)-1,3-dimethyl-3,7-dihydropurine-2,6-dione. TFA

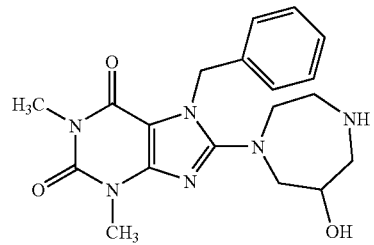

Step A: Preparation of 1,4-dibenzyl-[1,4]diazepan-6-ol (2A)
N,N-dibenzylethylenediamine (4.9 ml, 20.8 mmol) was dissolved in toluene (200 ml), triethylamine (8.94 ml, 64.5 mmol), and 1,3-dibromo-2-propanol (4.53 g, 20.8 mmol) was added. The reaction mixture was heated to reflux for 4 days. The solvents were evaporated and the remaining was redissolved in water (150 ml) and ethyl acetate (150 ml). The aqueous layer was acidified with 6N hydrochloric acid until pH=2, and the layers were separated. The aqueous layer was washed with 3×100 ml of ethyl acetate and the combined organic material was dried with sodium sulphate, filtered and the solvent was evaporated. The crude product was purified by chromatography onsilica, using 5% methanol in dichloromethane as the eluent. Fractions containing the product were evaporated, to afford 3.59 g of 2A as an yellow oil in 59% yield.

¹H-NMR (MeOH-d₄): δ 7.30 (10H, m); 3.81 (1H, m); 3.67 (4H, s); 2.90 (2H, dd); 2.74–2.60 (6H, m). HPLC-MS (Method B): m/z=297 (M+1); R11.49 min.

Step B: Preparation of [1,4]diazepan-6-ol. HOAc (2B)

1,4-Dibenzyl-[1,4]diazepan-6-ol (2A) (873 mg, 2.95 mmol) was hydrogenated for 21 days as described in example 1, step C. The reaction mixture was filtered twice, and the solvents were evaporated to afford 420 mg of 2B, as yellow crystals in 60% yield.

¹H-NMR (MeOH-d₄): δ 4.07 (1H, m); 3.61 (1H, m); 3.27–2.98 (8H, m); 1.92 (6H, s). HPLC-MS (Method B): m/z=117 (M+1); R=0.36 min.

Step C: Preparation of 7-Benzyl-8-(6-hydroxy-[1,4]diazepan-1-yl)-1,3-dimethyl-3,7-dihydropurine-2,6-dione. TFA (2)

[1,4]Diazepan-6-ol acetate (2B) (116 mg, 0.49 mmol) and 7-benzyl-8-chloro-1,3-dimethyl-3,7-dihydropurine-2,6-dione (100 mg, 0.33 mmol) were dissolved in 2-propanol (20 ml) and triethylamine (0.68 ml, 4.9 mmol) and the mixture was subjected to micro waves (150° C., 6 bar, 300 W, 8 hours). The solvents were evaporated and the remaining was redissolved in dichloromethane (20 ml) and water (20 ml). The aqueous layer was acidified with potassium hydrogen sulfate until pH=2. The aqueous layer was separated and aqueous sodium hydroxide was added until pH=12. The aqueous layer was extracted with 3×50 ml of dichloromethane, and the combined organic material were added excess trifluoroacetic acid, and evaporated, to afford 123 mg of the title compound as a brown oil in 75% yield.

¹H-NMR (MeOH-d₄): δ 7.31 (3H, m); 7.14 (2H, m); 5.59 (2H, s); 4.23 (1H, m); 3.27–4.02 (14H, m). HPLC-MS (Method B): m/z=385 (M+1); R_f=1.52 min.

Example 3

7-Benzyl-8-(3-hydroxymethyl-[1,4]diazepan-1-yl)-1,3-dimethyl-3,7-dihydropurine-2,6-dione. TFA

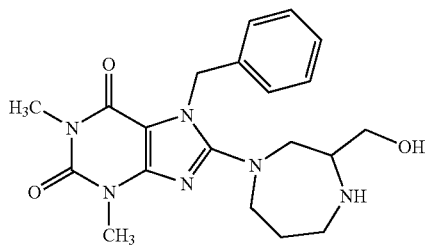

Step A: Preparation of 1,4-dibenzyl-[1,4]diazepane-2-carboxylic acid methyl ester (3A)

N,N'-Dibenzylpropane-1,3-diamine (Sandstroem, J. et al, Tetrahedron; EN; 34; 1978; 371-378) (2.0 g, 7.86 mmol), methyl 2,3-dibromopropionate (1.28 ml, 7.86 mmol), and potassium carbonate (2.17 g, 15.72 mmol) were dissolved in dry dimethylformamide (125 ml) and methanol (20 ml) and the mixture was heated to reflux for 6 days. The reaction mixture was allowed to cool to room temperature and water (200 ml) and ethyl acetate (200 ml) were added. The aqueous layer was extracted with 2×200 ml of ethyl acetate, and the combined organic layers were dried with sodium sulfate, filtered and the solvent was evaporated. The crude product was purified by chromatography on silica, using a mixture of ethyl acetate and heptane 1:6 as the eluent. Fractions containing the product were evaporated, to afford 180 mg of 3A as an clear oil in 7% yield.

¹H-NMR (CDCl₃): δ 7.29 (10H, m); 3.71 (3H, s); 3.62 (4H, s); 3.33–2.51 (7H, m); 1.74 (2H, m). HPLC-MS (Method B): m/z=339 (M+1); R_f=2.76 min.

Step B: Preparation of (1,4-dibenzyl-[1,4]diazepan-2-yl)-methanol (3B)

1,4-Dibenzyl-[1,4]diazepane-2-carboxylic acid methyl ester (3A) (180 mg, 0.53 mmol) was reduced and purified by the method described in example 1, step B, to afford 169 mg of 3B as an yellow oil in 100% yield.

¹H-NMR (CDCl₃): δ 7.31 (10H, m); 3.87 (2H, dd); 3.62 (2H, s); 3.43 (2H, d); 3.03–2.43 (7H, m); 1.74 (2H, m). HPLC-MS (Method B): m/z=31.1 (M+1); Rt=1.54 min.

Step C: Preparation of ([1,4]diazepan-2-yl)methanol. HOAc (3C) (1,4-Dibenzyl-[1,4]diazepan-2-yl)methanol was hydrogenated for 20 days as described in example 1, step C. The reaction mixture was filtered twice, and the solvents were evaporated. The crude product was crystallized from dry dichloromethane and diethyl ether to afford 62 mg of 3C, as white crystals in 46% yield.

¹H-NMR (MeOH-d4): δ 3.65–2.80 (9H, m); 1.93 (9H, s); 1.27 (2H, m). HPLC-MS (Method B): m/z=131 (M+1); Rt=0.29 min.

Step D: Preparation of 7-benzyl-8-(3-hydroxymethyl-[1,4]diazepan-1-yl)-1,3-dimethyl-3,7-dihydropurine-2,6-dione. TFA (3)

([1,4]Diazepan-2-yl)methanol acetate (3C) (62 mg, 0.25 mmol) and 7-benzyl-8-chloro-1,3-dimethyl-3,7-dihydropurine-2,6-dione (50.3 mg, 0.17 mmol) was subjected to micro waves (150° C., 11 bar, 300 W, 12 hours) as described in example 2, step C. The solvents were evaporated and the crude product was purified by preparative HPLC (method A2; R₁=6.90 min.) to afford 8 mg of the title compound as an yellow oil in 12% yield.

HPLC-MS (Method B): m/z=399 (M+1); R_f=1.78 min.

Example 4

General Procedure (A)

7-Benzyl-1,3-dimethyl-8-piperazin-1-yl-3,7-dihydropurine-2,6-dione. TFA

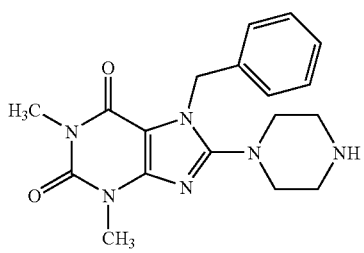

Step A: Preparation of 7-benzyl-8-chloro-1,3-dimethyl-3,7-dihydro-purine-2,6-dione (4A): 8-Chloro-1,3-dimethyl-3,7-dihydro-purine-2,6-dione (2.0 g, 9.3 mmol) was dissolved in DMF (50 ml) K$_2$CO$_3$ (2.57 g, 18.6 mmol) and benzyl bromide (1.75 g, 10.3 mmol) were added and the reaction mixture was stirred for 15 hours at room temperature. The reaction mixture was evaporated in vacuo the residue was dissolved in DCM:H$_2$O (1:1) (100 ml) the water phase was extracted with DCM (50 ml) the combined organic phase was dried with MgSO$_4$ filtered and evaporation gave 4A as a white crystalline compound. Yield: 2.92 g. Mp: 145.7–147.1° C.

$^1$H-NMR (CDCl$_3$): δ 7.2–7.4 (m, 5H); 5,15 (s, 2H); 3.55 (s, 3H); 3.4 (s, 3H).

$^{13}$C-NMR (CDCl$_3$): δ 154.8; 151.6; 147.7; 139.1; 135.3; 129.3; 128.9; 128.4; 108.1; 49.6; 30.2; 28.5. HPLC-MS (Method B): M+1=305; Rt=1,9 min.

HPLC (Method D; MeCN: buffer 1:1) R$_t$=7,19 min; purity>99%.

Step B: Preparation of 4-(7-Benzyl-1,3-dimethyl-2,6-dioxo-2,3,4,5-tetrahydro-1H-purine-8-yl)-piperazine-1-carboxylic acid tert-butylate (4B):

7-Benzyl-8-chloro-1,3-dimethyl-3,7-dihydro-purine-2,6-dione (4A) (1.0 g, 3.3 mmol) was dissolved in ethanol (30 ml) piperazine-1-carboxylic acid tert-butylate (0.73 g, 3.9 mmol) and TEA (0.66 g, 0.1 ml, 6.6 mmol) were added and the reaction mixture was heated for 72 hours at 120° C. in a sealed vessel. The reaction mixture was evaporated and the remaining oil was purified on a silica gel column using (DCM, MeOH) (39:1) as eluent giving 0.93 g of 4B as a yellow oil. Yield: 62%.

HPLC (Method D; MeCN: buffer 1:1) R$_t$=13.15 min; purity>96%.

R$_t$=13.15 min. >96% purity (Method D: MeCN: buffer (1:1) pH=3H$_3$PO$_4$)

$^1$H-NMR (CDCl$_3$): δ 7.2–7.3 (m, 5H); 5.4 (s, 2H); 3.5 (s, 3H); 3.45 (m, 4H); 3.35 (s, 3H); 3.1 (m, 4H); 1.5 (s, 9H).

$^{13}$C-NMR (CDCl$_3$): δ 155.0; 156.4; 151.9; 154.8; 147.8; 136.9; 129.1; 128.8; 128.2; 127.1; 105.3; 80.4; 50.6; 48.9; 43.3 (broad); 30.0; 28.7; 28.1., Step C: Preparation of 4-(7-Benzyl-1,3-dimethyl-8-piperazin-1-yl-3,7-dihydropurine-2,6-dione, TFA (4):

4-(7-Benzyl-1,3-dimethyl-2,6-dioxo-2,3,4,5-tetrahydro-1H-purine-8-yl)-piperazine-1-carboxylic acid tert-butylate (4B) (188 mg, 0.41 mmol) was dissolved in TFA (10 ml). The reaction mixture was stirred at room temperature for 2 hours. The mixture was evaporated in vacuo. The remaining oil was crystallised from acetone/ether. The title compound was isolated as the white TFA salt 170 mg. Yield: 89%. Mp: 217–19° C. decomposes.

HPLC (Method D; MeCN: buffer 1:1) R$_t$=2.98 min; purity >99%.

$^1$H-NMR (CDCl$_3$): δ 7.15–7.4 (m, 51H); 5.4 (s, 2H); 3.45 (s, 3H); 3.4 (broad d, 2H); 3.15 (broad d, 2H); 3.05 (s, 3H). HPLC-MS (Method B): m/z=355 (M+1); R$_t$=1.699 min; TIC area=100%

Example 5

General Procedure (A)

1,3-Dimethyl-7-(4-methylbenzyl)-8-piperazin-1-yl-3,7-dihydropurine-2,6-dione. HCl

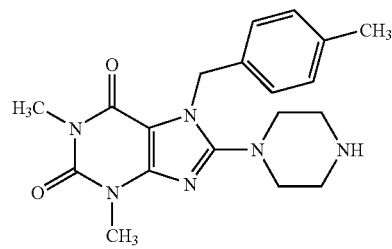

HPLC-MS (Method C) m/z=369 (M+1); R$_t$=1.319 min.

Example 6

General Procedure (A)

3-(1,3-Dimethyl-2,6-dioxo-8-piperazin-1-yl-1,2,3,6-tetrahydropurin-7-ylmethyl) benzonitrile. TFA

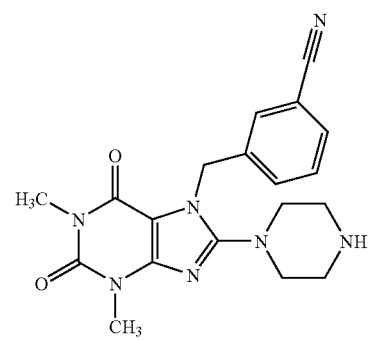

HPLC-MS (Method C) m/z=380 (M+1); R$_t$=1.22 min.

Example 7

General Procedure (A)

2-(1,3-Dimethyl-2,6-dioxo-8-piperazin-1-yl-1,2,3,6-tetrahydropurin-7-ylmethyl) benzonitrile. TFA

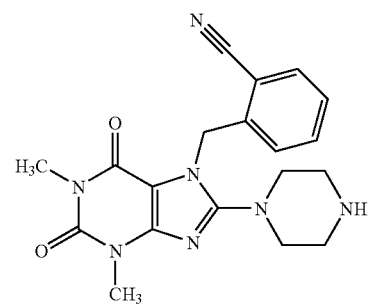

HPLC-MS (Method C) m/z=380 (M+1); R$_t$=1.18 min.

Example 8

General Procedure (A)

1,3-Dimethyl-7-(1-phenylethyl)-8-piperazin-1-yl-3,7-dihydropurine-2,6-dione. TFA

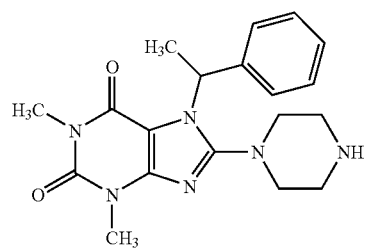

HPLC-MS (Method C) m/z=369 (M+1); $R_t$=2.47 min

Example 9

General procedure (A)

7-(2-Iodobenzyl)-1,3-dimethyl-8-piperazin-1-yl-3,7-dihydropurine-2,6-dione. TFA

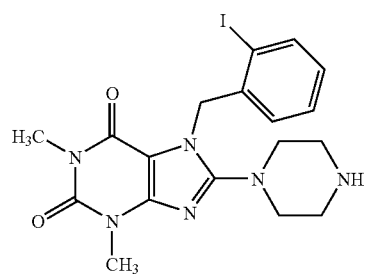

HPLC-MS (Method C) m/z=481 (M+1); $R_t$=1.43 min.

Example 10

General Procedure (A)

1,3-Dimethyl-8-piperazin-1-yl-7-(2-trifluoromethylbenzyl)-3,7-dihydropurine-2,6-dione. TFA

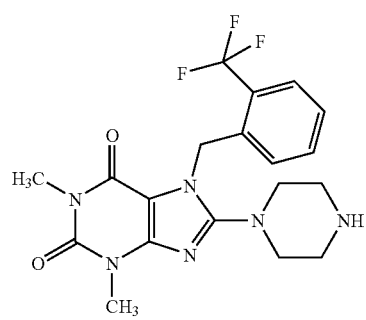

HPLC-MS (Method C) m/z=423 (M+1); $R_t$=1.44 min.

Example 11

General Procedure (A)

1,3-Dimethyl-7-naphthalen-1-ylmethyl-8-piperazin-1-yl-3,7-dihydropurine-2,6-dione. TFA

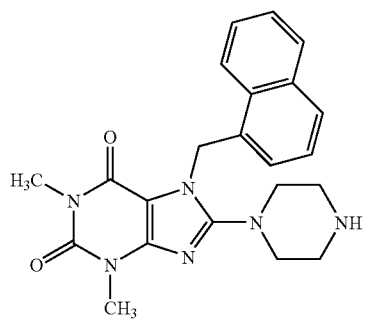

HPLC-MS (Method C) m/z=405 (M+1); $R_t$=1.55 min.

Example 12

General Procedure (A)

1,3-Dimethyl-7-naphthalen-2-ylmethyl-8-piperazin-1-yl-3,7-dihydropurine-2,6-dione. TFA

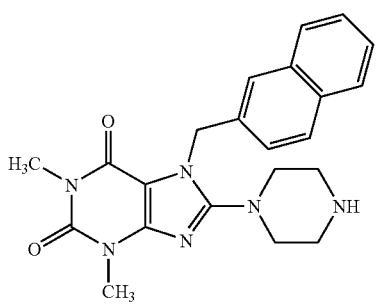

HPLC-MS (Method C) m/z=405 (M+1); $R_t$=1.51 min.

Example 13

General Procedure (A)

7-(3-Bromobenzyl)-1,3-dimethyl-8-piperazin-1-yl-3,7-dihydropurine-2,6-dione. TFA

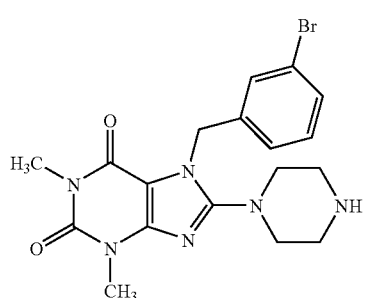

HPLC-MS (Method C) m/z=434 (M+1); $R_t$=1.33 min.

Example 14

General Procedure (A)

7-Benzyl-8-(3-isopropylpiperazin-1-yl)-1,3-dimethyl-3,7-dihydropurine-2,6-dione. HCl

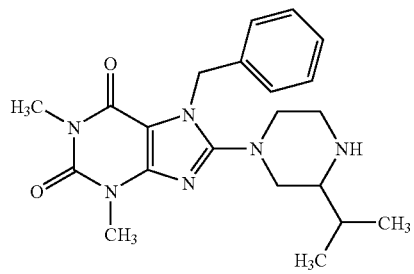

The piperazine moiety was prepared according to the general procedure for preparation of piperazine derivatives.

$^1$H-NMR (CDCl$_3$): δ 7.1–7.4 (m; 5H); 5.4 (s; 2H); 3.55 (s; 3H); 3.35 (s; 3H); 3.3 (s br; 1H); 2.9–3.05 (m; 3H); 2.65 (t; 1H); 2.45 (dt, 1H); 2.1 (s br; 1H); 1.5 (p; 1H); 0.9 (d; 3H); 0.75 (d; 3H). $^{13}$C-NMR (CDCl$_3$): δ 157.17; 154.98; 152.12; 148.16; 137.12; 129.15; 128.07; 126.94; 105.33; 60.88; 54.64; 51.04; 49.06; 45.90; 31.42; 30.12; 28.17; 19.21; 19.03.

Example 15

General Procedure (C)

7-Benzyl-8-[1,4]diazepan-1-yl-1,3-dimethyl-3,7-dihydro-purine-2,6-dione. TFA

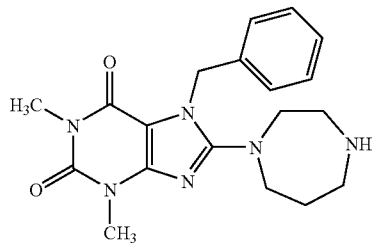

HPLC-MS (Method B): m/z=369; R$_t$=1.75 min. TIC area=100%

Example 16

General Procedure (C)

1,3-Dimethyl-7-(2-oxo-2-pyrrolidin-1-yl-ethyl)-8-piperazin-1-yl-3,7-dihydro-purine-2,6-dione. HCl

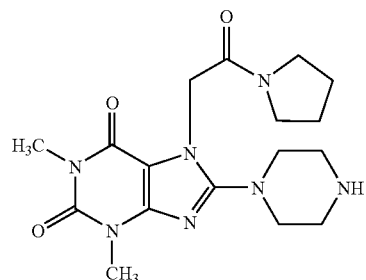

HPLC-MS (Method B): m/z=376; R$_t$=2.86 min.+0.47 min; Area: 47+53%

Example 17

General Procedure (C)

2-(8-[1,4]Diazepan-1-yl-1,3-dimethyl-2,6-dioxo-1,2,3,6-tetrahydro-purin-7-ylmethyl)-benzonitrile. HCl

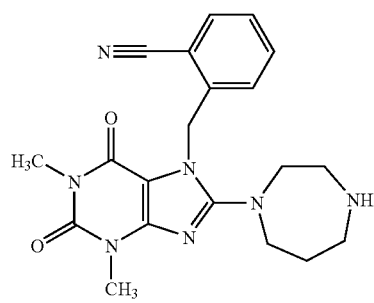

Step A 2-(8-Chloro-1,3-dimethyl-2,6-dioxo-1,2,3,6-tetrahydro-purin-7-ylmethyl) benzonitrile (0.5 g, 1.5 mmol) and homopiperazine (0.45 g, 4.5 mmol) and TEA (0.77 ml; 7.5 mmol) was heated in 2-propanol in a closed vessel in a micro wave oven at 150° C. for 4 hours. The reaction mixture was evaporated in vacuo. The remaining oil was purified on a silica gel column with DCM/MeOH (3:1) as eluent, giving the title compound as an oil. The oil was dissolved in DCM (3 ml) and hydrochloride in ether was added. Yield 632 mg white crystals. Mp: 160.8–162.3° C.

$^1$H-NMR (MeOH-d$_4$): δ 7.75 (dd; 1H); 7.65 (dt; 1H); 7.4 (t; 1H); 7.1 (d; 1H); 5.65 (s; 2H); 3.55–3.65 (s; 2H); 3.5 (s; 3H); 3.2 (s; 3H); 3.1 (t; 2H); 2.9 (t; 2H); 1.9 (t, t; 2H).

Example 18

General Procedure (C)

8-[1,4]Diazepan-1-yl-7-(2-iodo-benzyl)-1,3-dimethyl-3,7-dihydro-purine-2,6-dione. HCl

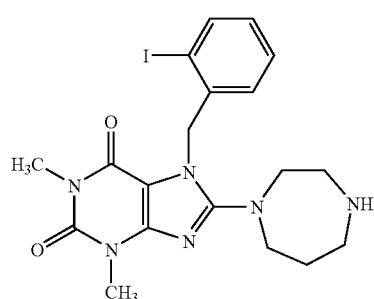

$^1$H-NMR (CDCl$_3$): δ 7.85 (d; 1H); 7.25 (t; 1H); 6.95 (t; 1H); 5.45 (s; 2H); 3.55 (s; 3H); 3.35-3.5 (m; 2H); 3.35 (s; 3H); 2.7–3.1 (m; 6H); 1.75 (m; 2H).

Example 19

General Procedure (A)

7-(2-Difluoromethoxy-benzyl)-1,3-dimethyl-8-piperazin-1-yl-3,7-dihydro-purine-2,6-dione. TFA

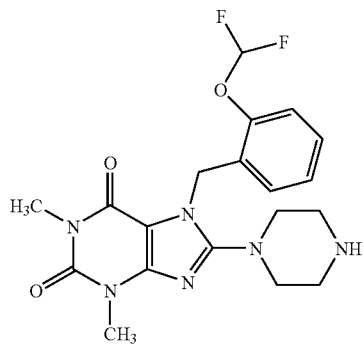

HPLC-MS (Method B) m/z=421; $R_t$=3.72 min. area: 100%

Example 20

General Procedure (A)

7-(2,3-Dimethoxy-benzyl)-1,3-dimethyl-8-piperazin-1-yl-3,7-dihydro-purine-2,6-dione. TFA

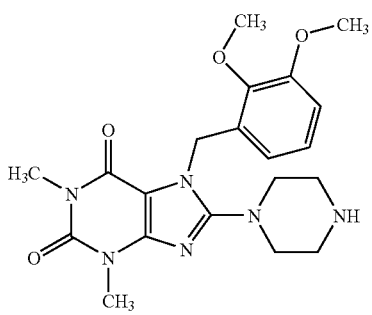

HPLC-MS (Method B): m/z=415; $R_t$=3.65 min. area: 100%.

Example 21

General Procedure (A)

1,3-Dimethyl-8-piperazin-1-yl-7-(2-trifluoromethoxy-benzyl)-3,7-dihydro-purine-2,6-dione.

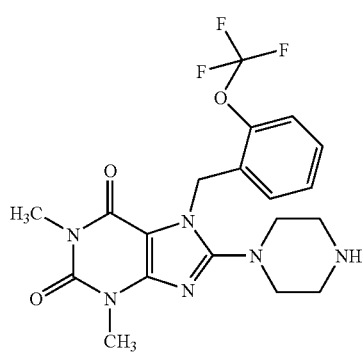

HPLC-MS (Method B): m/z=439; $R_t$=2.75 min. area 99%

Example 22

General Procedure (A)

1,3-Dimethyl-8-piperazin-1-yl-7-(2-trifluoromethylsulfanyl-benzyl)-3,7-dihydro-purine-2,6-dione. TFA

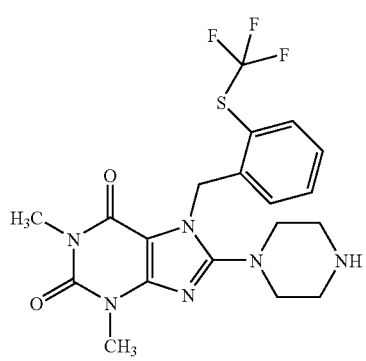

HPLC-MS (Method B): m/z=455; $R_t$=4.17 min. area 99%

Example 23

General Procedure (A)

4-(1,3-Dimethyl-2,6-dioxo-8-piperazin-1-yl-1,2,3,6-tetrahydro-purin-7-yl)-butyronitrile. TFA

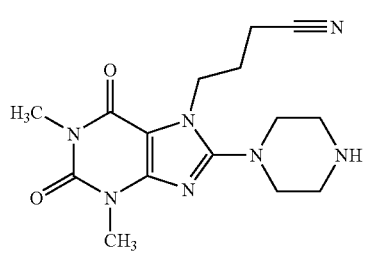

HPLC-MS (Method B): m/z=332; $R_t$=2.45 min. area 99,7%

Example 24

General Procedure (A)

(R)-7-Benzyl-8-(3-isopropylpiperazin-1-yl)-1,3-dimethyl-3,7-dihydropurine-2,6-dione. TFA

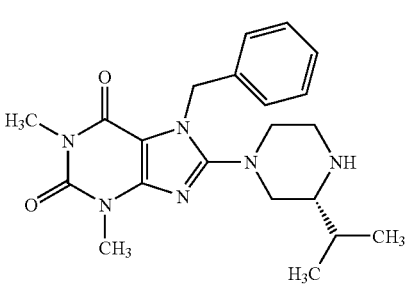

The piperazine moiety was prepared according to the general procedure for preparation of piperazine derivatives.

¹H-NMR (CDCl₃): δ 7.2–7.35 (m; 3H) 7.15 (dd; 2H); 5.4 (s; 2H); 3.6 (s; 3H); 3.35 (s; 3H); 3.3 (m; 5H); 3.1 (m; 2H); 1.8 (p; 1H); 0.9 (d; 3H); 0.75 (d; 3H). HPLC-MS (Method B): m/z=397 (M+1); R$_t$=2.06 min.

Example 25

General Procedure (A)

(S)-7-Benzyl-8-(3-isopropylpiperazin-1-yl)-1,3-dimethyl-3,7-dihydropurine-2,6-dione. TFA

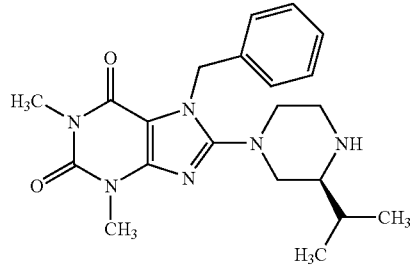

¹H-NMR (CDCl₃): δ 11.4 (broad s; 2.5H); 7.25–7.4 (m; 3H); 7.15 (dd; 2H); 5.4 (s; 2H); 3.6 (s; 3H); 3.25–3.5 (m; 7H); 3.0–3.2 (m; 2H); 1.8 (p; 1H); 0.85 (d; 3H); 0.7 (d; 3H). HPLC-MS (Method B): m/z=397 (M+1); R$_t$=2.09 min.

Example 26

General Procedure (A)

7-Benzyl-8-(6,9-diazaspiro[4.5]dec-9-yl)-1,3-dimethyl-3,7-dihydropurine-2,6-dione. TFA

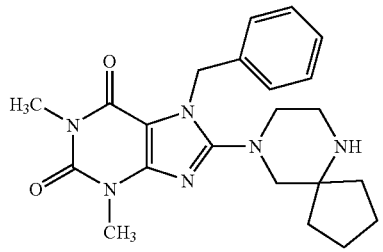

The piperazine moiety was prepared according to the general procedure for preparation of piperazine derivatives.
¹H-NMR (CDCl₃): δ 10.0 (broads; 2H); 8.9 (broad s, 2H); 7.25–7.4 (m, 3H); 7.1 (d, 2H); 5.4 (s; 2H); 3.55 (s; 3H); 3.35–3.4 (m; 5H); 3.1–3.3 (m; 4H); 1.6–1.85 (m; 6H); 1.3 (m; 2H). HPLC-MS (Method B): m/z=409 (M+1); R$_t$=2.11 min.

Example 27

General Procedure (A)

7-Benzyl-8-(piperazin-3-spiro-3'-bicyclo[2,2,1]heptane-1-yl)-1,3-dimethyl-3,7-dihydropurine-2,6-dione. TFA

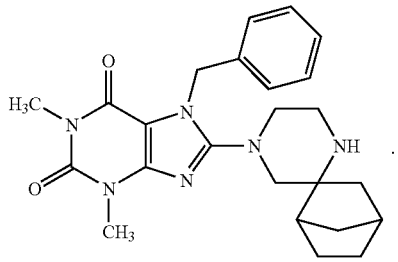

The piperazine moiety was prepared according to the general procedure for preparation of piperazine derivatives.
¹H-NMR (CDCl₃): δ 11.1 (broad s; 1H); 8.9 (broad s; 1H); 7.25–7.4 (m; 3H); 7.1 (dd; 2H); 5.45 (s; 2H); 3.5 (s; 3H); 3.15–3.4 (m; 9H); 2.2–2.3 (d; 2H); 1.1–1.6 (m; 7H); 0.9 (d; 1H). HPLC-MS (Method B): m/z=435 (M+1); R$_t$=2.34 min.

Example 28

General Procedure (A)

8-[1,4]Diazepan-1-yl-7-(2-methoxy-benzyl)-1,3-dimethyl-3,7-dihydro-purine-2,6-dione. TFA

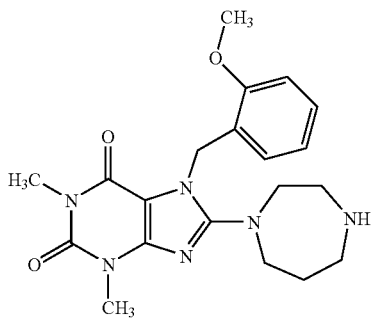

HPLC-MS (Method B): m/z=399; R$_t$=1.93 min. UV area=98.63%

Example 29

General Procedure (A)

8-[1,4]Diazepan-1-yl-1,3-dimethyl-7-naphthalen-1-ylmethyl-3,7-dihydro-purine-2,6-dione. TFA

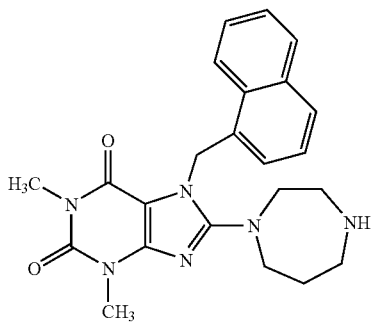

HPLC-MS (Method B): m/z=419; R$_t$=2.26 min. UVarea=99.7%.

Example 30

General Procedure (A)

8-[1,4]Diazepan-1-yl-7-(2-fluoro-benzyl)-1,3-dimethyl-3,7-dihydro-purine-2,6-dione. TFA

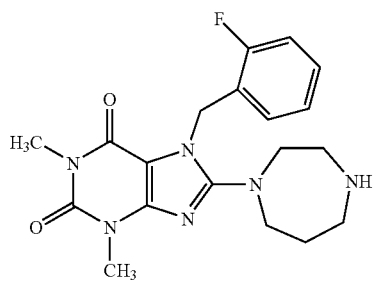

HPLC-MS (Method B): m/z=387; $R_t$=1.86 min. UVarea=94.4%.

Example 31

General Procedure (A)

8-[1,4]Diazepan-1-yl-1,3-dimethyl-7-(2-methyl-benzyl)-3,7-dihydro-purine-2,6-dione. TFA

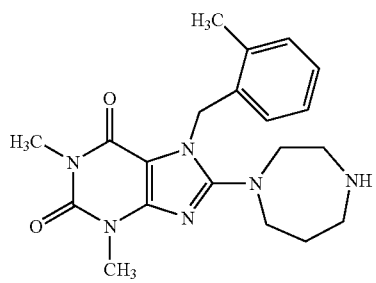

HPLC-MS (Method B): m/z=383 (M+1); Rt=1.99 min. UVarea=97.68%.

Example 32

General Procedure (A)

7-(2-Chloro-benzyl)-8-[1,4]diazepan-1-yl-1,3-dimethyl-3,7-dihydro-purine-2,6-dione. TFA

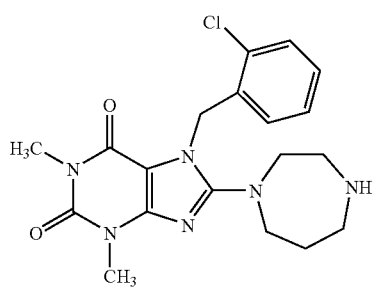

HPLC-MS (Method B): m/z=403; 405; 406; (M+1); $R_t$=1.97 min. UVarea=98.93.

Example 33

General Procedure (A)

7-(2-Bromo-benzyl)-8-[1,4]diazepan-1-yl-1,3-dimethyl-3,7-dihydro-purine-2,6-dione. TFA

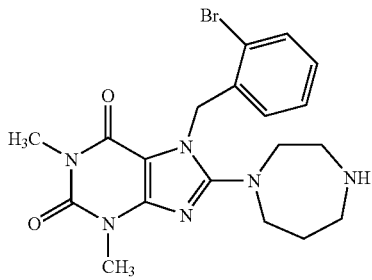

HPLC-MS (Method B): m/z=447; 450; (M+1); $R_t$=2.09 min. UVarea=98.51.

Example 34

General Procedure (A)

8-[1,4]Diazepan-1-yl-1,3-dimethyl-7-(2-trifluoromethyl-benzyl)-3,7-dihydro-purine-2,6-dione. TFA

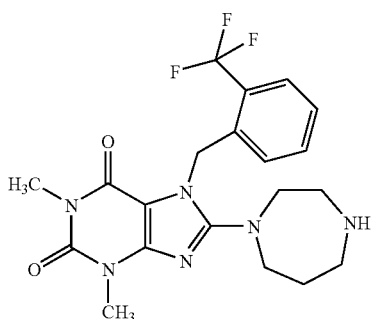

HPLC-MS (Method B): m/z=437 (M+1); $R_t$=2.20 min. UVarea=99.50%.

Example 35

General Procedure (A)

8-[1,4]Diazepan-1-yl-1,3-dimethyl-7-(2-nitro-benzyl)-3,7-dihydro-purine-2,6-dione. HCl

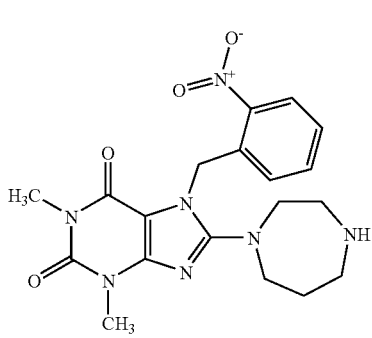

HPLC-MS (Method B): m/z=437 (M+23); $R_t$=2.23 min. UV area=100%.

Example 36

General Procedure (B)

3-Benzyl-8-piperazin-1-yl-7-(2-trifluoromethyl-benzyl)-3,7-dihydro-purine-2,6-dione. TFA

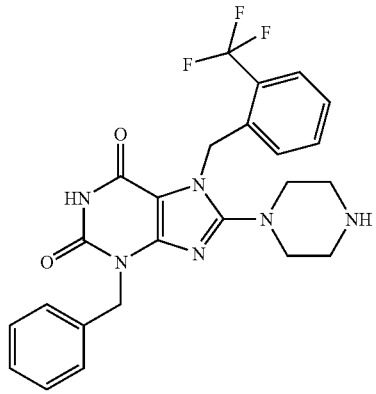

$^1$H-NMR (DMSO-d$_6$): δ 11,12 (s, 1H); 8,83 (s, 1H); 7,86–7,71 (d, 2H); 7,71–7,45 (m, 2H) 7,45–7,23 (m, 5H); 7,08–6,98 (d, 1H); 5,48 (s, 1H); 5,10 (s, 1H); 3,34-3,01 (m, 4H)

Example 37

General Procedure (B)

3,7-Dibenzyl-1-(2-hydroxy-ethyl)-8-piperazin-1-yl-3,7-dihydro-purine-2,6-dione. TFA

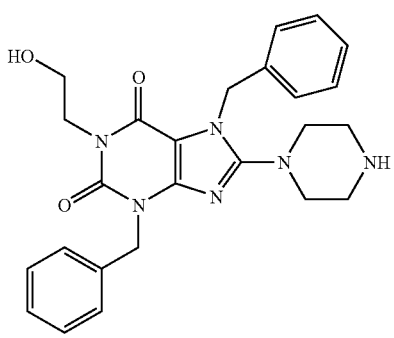

$^1$H-NMR (DMSO-d$_6$): δ 8.86 (s br, 2H); 7.40–7.18 (m, 10H); 5.41 (s, 2H); 5.13 (s, 2H); 3.93 (t, 2H); 3.45 (t, 2H); 3.31 (s br, 4H); 3.19 (s br, 4H).

Example 38

General Procedure (B)

3-Benzyl-7-phenethyl-8-piperazin-1-yl-3,7-dihydro-purine-2,6-dione. TFA

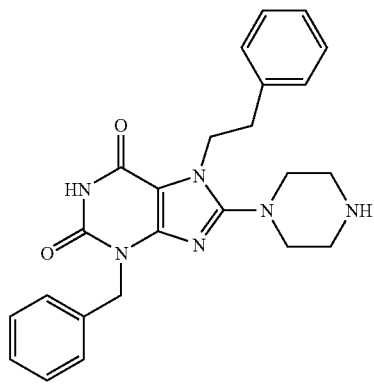

$^1$H-NMR (DMSO-d$_6$): δ 11.11 (s, 1H); 8.79 (s br, 2H); 7.40–7.05 (m, 10H); 5.02 (s, 2H); 4.30 (t, 2H); 3.09 (s br, 8H); 3.03 (t, 2H).

Example 39

General Procedure (B)

3,7-Dibenzyl-8-[1,4]diazepan-1-yl-3,7-dihydro-purine-2,6-dione. TFA

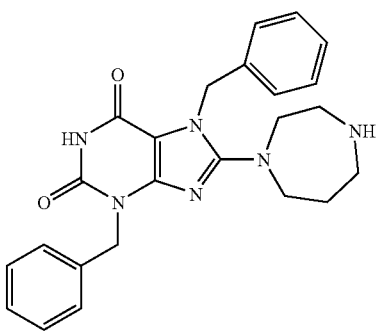

$^1$H-NMR (DMSO-d$_6$): δ 7.67–6.92 (m, 10H); 5.42 (s.2H); 5.04 (s, 2H); 3.89–3.35 (m, 5H); 2.96–2.35 (m, 5H); 1.68 (s, 2H). HPLC-MS m/z=431

Example 40

General Procedure (B)

7-Benzyl-8-[1,4]diazepan-1-yl-3-methyl-3,7-dihydro-purine-2,6-dione. TFA

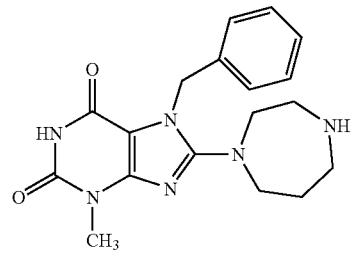

$^1$H-NMR (DMSO-d$_6$): δ 10.89 (s, 1H); 9.19 (s, 2H); 7.46–7.00 (m, 5H) 5.42 (s, 2H) 3.67 (s br, 2H); 3.53–3.40 (m, 2H); 3.32 (s, 3H); 3.23 (s br, 2H); 3.14 (s, 2H); 2.00 (m, 2H)HPLC-MS m/z=355

Example 41

General Procedure (B)

3,7-Dibenzyl-8-[1,4]diazepan-1-yl-1-propyl-3,7-dihydro-purine-2,6-dione. TFA

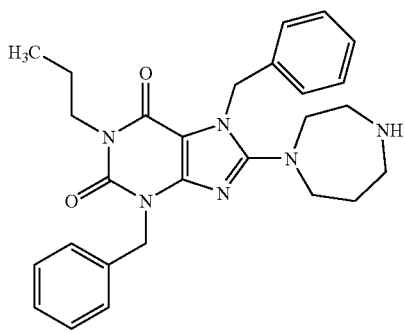

$^1$H-NMR (DMSO-d$_6$): δ 8.67 (s br, 2H); 7.45–7.06 (m, 10H); 5.46 (s, 2H) 5.12 (s, 2H) 3.79 (t, 2H); 3.67 (m, 2H); 3.50 (m, 2H); 3.27 (s br, 2H) 3.16 (s br, 2H); 1.98 (m, 2H); 1.52 (m, 2H); 0.81 (t, 3H).

Example 42

General Procedure (B)

3,7-Dibenzyl-8-[1,4]diazepan-1-yl-1-(2-hydroxy-ethyl)-3,7-dihydro-purine-2,6-dione. TFA

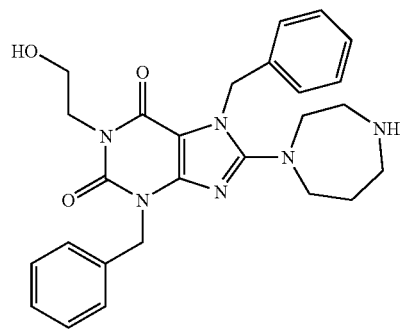

$^1$H-NMR (DMSO-d$_6$): δ 8.79 (s, 2H); 7.41–7.22 (m, 8H); 7.20–7.07 (m, 2H); 5.47 (s, 2H); 5.12 (s, 2H); 4.00–3.86 (t, 2H); 3.73–3.61 (m, 2H); 3.54–3.40 (m, 4H) 3.27 (s, 2H); 3,15 (s, 2H) 1.98 (s, 2H)

Example 43

General Procedure (B)

2-(3,7-Dibenzyl-8-[1,4]diazepan-1-yl-2,6-dioxo-2,3,6,7-tetrahydro-purin-1-yl)—N,N-diethyl-acetamide

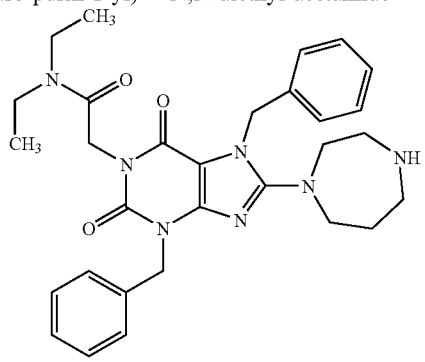

$^1$H-NMR (DMSO-d$_6$): δ 8.67 (s br, 2H); 7.41–7.20 (m, 8H); 7.16–7.03 (m, 2H); 5.47 (s, 2H); 5.13 (s, 2H); 4.64 (s, 2H); 3.69 (s br, 2H); 3.51 (t.2H) 3.44–3.10 (m, 7H); 2.67 (s, 1H); 1.98 (s br, 2H); 1.16 (t, 3H) 0.99 (t, 3H)

Example 44

General Procedure (B)

1,3,7-Tribenzyl-8-piperazin-1-yl-3,7-dihydro-purine-2,6-dione. TFA

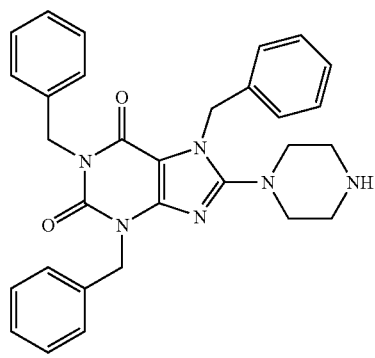

$^1$H-NMR (DMSO-d$_6$): δ 8.83 (s br, 2H); 7.48–7.16 (m,15H); 5.40 (s, 2H); 5.14 (s, 2H); 5.02 (s, 2H); 3.20 (s br, 4H).

Example 45

General Procedure (B)

1,3,7-Tribenzyl-8-[1,4]diazepan-1-yl-3,7-dihydro-purine-2,6-dione. TFA

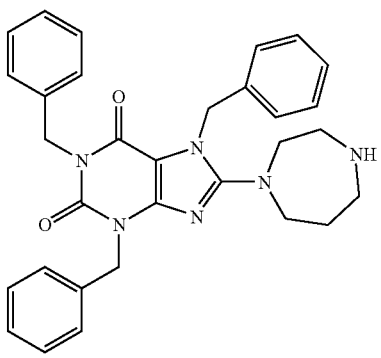

$^1$H-NMR (DMSO-d$_6$): δ 8.76 (s br, 2H); 7.58–7.04 (m, 15H); 5.48 (s, 2H) 5.13 (s, 2H); 5.03 (s, 2H); 3.70 (s br, 2H); 3.52 (t, 2H); 3.29 (s br, 2H); 3.17 (s br,2H); 1.99 (s br, 2H)

Example 46

General Procedure (A)

(S)-7-Benzyl-8-(3-benzyloxymethylpiperazin-1-yl)-1,3-dimethyl-3,7-dihydropurine-2,6-dione

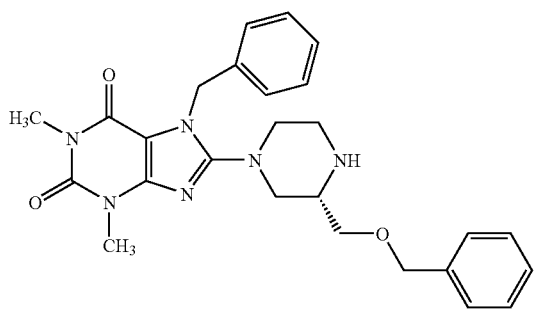

The piperazine moiety was prepared according to the general procedure for preparation of piperazine derivatives.

$^1$H-NMR (CDCl$_3$): δ 7.1–7.45 (m; 5H); 5.35 (s br; 2H); 4.5 (s; 2H); 3.5 (s; 3H); 3.35 (s; 3H); 3.2–3.0 (m; 3H); 2.7–3.1 (m; 5H); 2.25 (s br; 1H). $^{13}$C-NMR (CDCl$_3$): δ 156.92; 155.07; 152.11; 148.12; 138.22; 137.08; 129.16; 128.85; 128.22; 128.19; 128.15; 127.21; 105.35; 73.89; 72.07; 54.65; 53.89; 53.30; 51.41; 49.11; 45.14; 30.14; 28.22.

Example 47

General Procedure (B)

3,7-Dibenzyl-8-piperazin-1-yl-1-propyl-3,7-dihydro-purine-2,6-dione. TFA

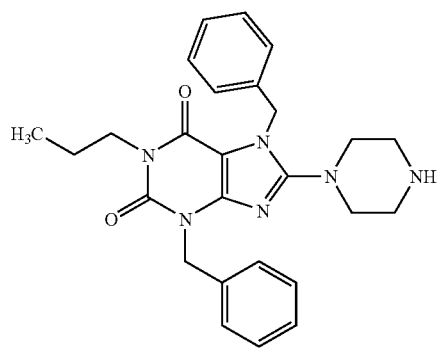

$^1$H-NMR (DMSO-d$_6$): 58.95 (s br, 2H); 7.40–7.20 m, 10H); 5.40 (s, 2H); 5.13 (s, 2H); 3.79 (t, 2H); 3.32 (m, 4H); 3.20 (m, 4H); 1.50 (sextet, 2H); 0.81 (t, 0.3H). HPLC-MS (Method C): m/z=459 (M+1); Rt=4.62 min

Example 48

General Procedure (B)

3,7-Dibenzyl-8-[1,4]diazepan-1-yl-1-propyl-3,7-dihydro-purine-2,6-dione. TFA

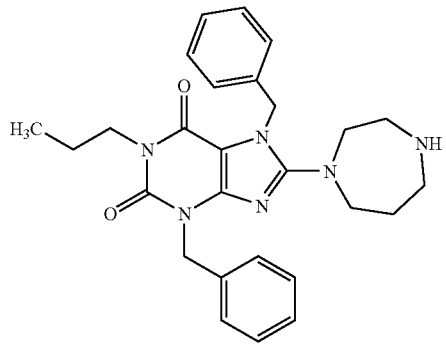

HPLC-MS. (Method C): m/z=473 (M+1); R$_t$=4.72 min

Example 49

General Procedure (B)

3,7-Dibenzyl-8-piperazin-1-yl-3,7-dihydro-purine-2,6-dione. TFA

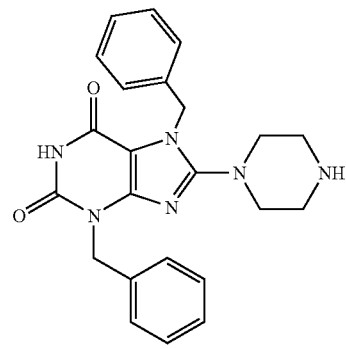

$^1$H-NMR (DMSO-d$_6$): δ 11.05 (s, 1H); 8.72 (s, br 2H); 7.40–7.20 (m, 10H); 5.37 (s, 2H); 5.07 (s, 2H). HPLC-MS (Method C): m/z=417 (M+1); R$_t$=3.69 min

Example 50

General Procedure (B)

3,7-Dibenzyl-8-[1,4]diazepan-1-yl-3,7-dihydro-purine-2,6-dione. TFA

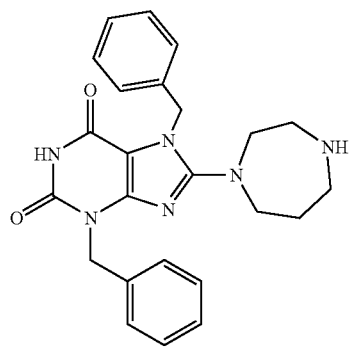

DMSO d6 d=10.90 (s, 1H); 8.65 (s br, 2H); 7.40–7.20 (m, 8H); 7.14 (d, 2H); 5.43 (s, 2H); 5.06 (s, 2H); 3.65 (m, 2H); 3.48 (m, 2H); 3.26 (m, 2H); 3.16 (s br, 2H); 1.97 (m, 2H) HPLC-MS (Method C): m/z=431 (M+1); $R_t$=3.83 min

Example 51

General Procedure (B)

2-(3-Benzyl-2,6-dioxo-8-piperazin-1-yl-1-propyl-1,2,3,6-tetrahydro-purin-7-ylmethyl)-benzonitrile

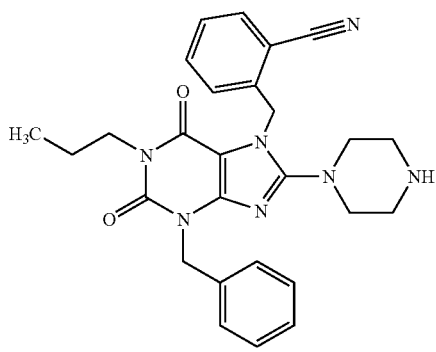

$^1$H-NMR (DMSO-$d_6$): δ 8.73 (s br, 2H); 7.88 (d, 1H); 7.64 (t, 1H); 7.49 (t, 1H); 7.42–7.25 (m, 5H); 7.15 (d, 1H); 5.56 (s, 2H); 3.73 (t, 2H); 1.46 (q, 2H); 0.77 (t, 3H). HPLC-MS (Method C): m/z=484 (M+1); $R_t$=4.56 min

Example 52

General Procedure (B)

2-(3-Benzyl-8-[1,4]diazepan-1-yl-2,6-dioxo-1-propyl-1,2,3,6-tetrahydro-purin-7-ylmethyl)-benzonitrile.

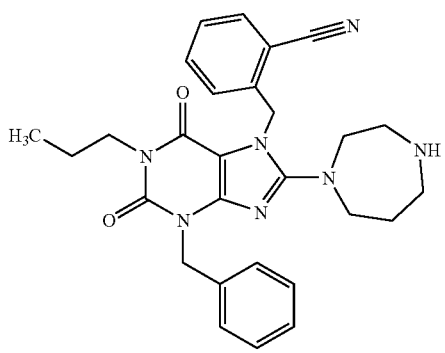

$^1$H-NMR (DMSO-$d_6$): δ 8.66 (s br, 2H); 7.89 (d, 1H); 7.65 (t, 1H); 7.52 (t, 1H); 7.42–7.10 (m, 5H); 7.12 (d, 1H); 5.59 (s, 2H); 5.14 (s, 2H); 3.78–3.65 (m, 4H); 3.48 (t, 2H); 3.31 (s br, 2H); 3.19 (s br, 2H); 2.00 (m 2H); 1.45 (q, 2H); 0.77 (t, 3H).

Example 53

General Procedure (B)

2-(3-Benzyl-2,6-dioxo-8-piperazin-1-yl-1,2,3,6-tetrahydro-purin-7-ylmethyl)-benzonitrile

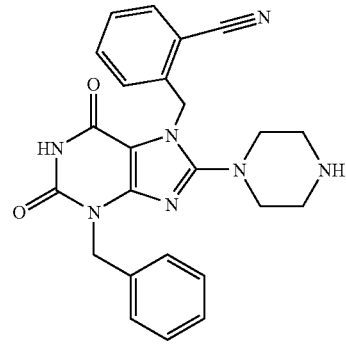

$^1$H-NMR (DMSO-$d_6$): δ 11.02 (s, 1H); 8.73 (s br 2H); 7.88 (d, 1H); 7.66 (t, 1H); 7.50 (t, H); 7.40–7.25 (m, 5H); 7.16 (d, 1H); 5.53 (s, 2H); 5.08 (s, 2H); 3.38 (s br, 4H); 3.20 (s br, 4H)

Example 54

General Procedure (B)

2-(3-Benzyl-8-[1,4]diazepan-1-yl-2,6-dioxo-1,2,3,6-tetrahydro-purin-7-ylmethyl)-benzonitrile

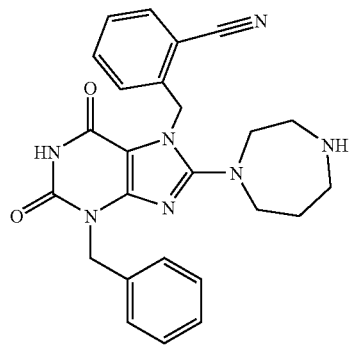

$^1$H-NMR (DMSO-$d_6$): δ 10.90 (s, 1H); 8.67 (s br, 1H); 7.89 (d, 1H); 7.67 (t, 1H); 7.51 (t, 1H); 7.44–7.25 (m, 5H); 7.12 (d, 1H); 5.56 (s, 2H); 5.07 (s, 2H); 3.68 (m, 2H); 3.46 (m, 2H); 3.36 (s br, 2H); 3.19 (s br, 2H); 1.89 (m, 2H).

Example 55

General Procedure (B)

3-Benzyl-7-(2-iodo-benzyl)-8-piperazin-1-yl-1-propyl-3,7-dihydro-purine-2,6-dione. TFA

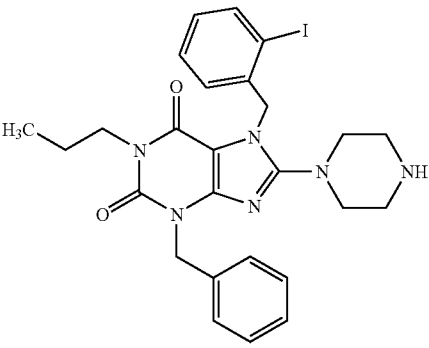

¹H-NMR (DMSO-d₆): δ 8.71 (s br, 2H); 7.93 (d 1H); 7.42–7.25 (m, 6H); 7.09 (d, 1H); 6.8 (d, 1H); 5.28 (s, 2H); 5.17 (s, 2H); 3.75 (t, 2H); 3.16 (s br 4H); 1.48 (q, 2H); 0.79 (t, 3H).

Example 56

General Procedure (B)

3-Benzyl-8-,[1,4]diazepan-1-yl-7-(2-iodo-benzyl)-1-propyl-3,7-dihydro-purine-2,6-dione. TFA

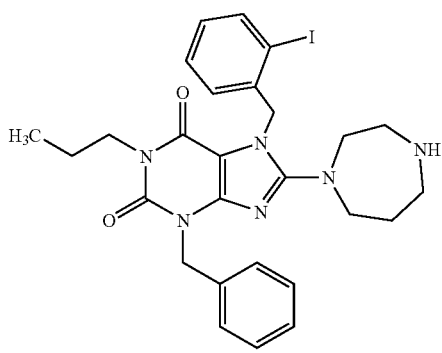

¹H-NMR (DMSO-d₆): δ 8.64 (s br, 2H); 7.93 (d, 1H); 7.44–7.25 (m, 6H); 7.09 (t, 1H); 6.76 (d, 1H); 5.29 (s, 2H); 5.16 (s, 2H); 3.75 (t, 2H); 3.67 (m, 2H); 3.41 (m, 2H); 3.16 (m, 2H); 1.95 (m, 2H); 1.49 (q, 2H); 0.80 (t, 3H). HPLC-MS (Method C): m/z=599 (M+1); R_t 4.96 min Example 57

General Procedure (B)

3-Benzyl-7-(2-iodo-benzyl)-8-piperazin-1-yl-3,7-dihydro-purine-2,6-dione. TFA

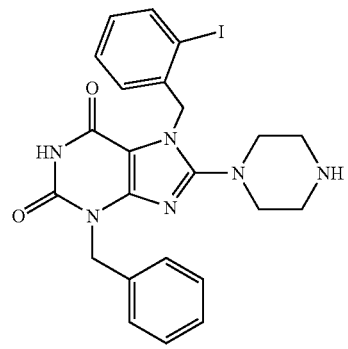

¹H-NMR (DMSO-d₆): δ 11.03 (s, 1H); 8.71 (s br, 1H); 7.92 (d, 1H); 7.42–7.28 (m, 6H); 7.08 (d, 1H); 6.81 (d, 1H); 5.26 (s, 2H); 5.10 (s, 2H); 3.15 (s br 4H).

Example 58

General Procedure (B)

3-Benzyl-8-[1,4]diazepan-1-yl-7-(2-iodo-benzyl)-3,7-dihydro-purine-2,6-dione. TFA

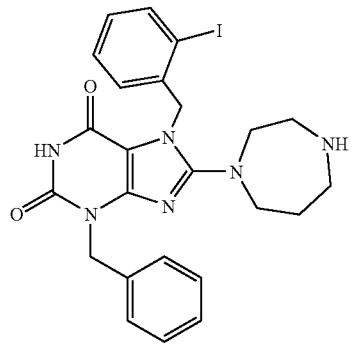

¹H-NMR (DMSO-d₆): δ 10.91 (s, 1H); 8.64 (s br, 2H); 7.93 (d, 1H); 7.44–2.25 (m, 6H); 7.09 (d, 1H); 6.75 (d, 1H); 5.27 (s, 2H); 5.09 (s, 2H); 3.65 (m, 2H); 3.39 (m, 1H); 3.30–3.22 (m, 3H); 3.15 (s br 2H); 1.94 (m, 2H).

Example 59

7-Benzyl-3-methyl-8-piperazin-1-yl-1-propyl-3,7-dihydro-purine-2,6-dione. TFA

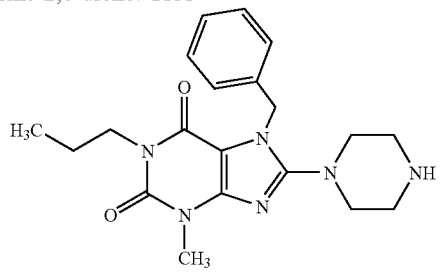

¹H-NMR (DMSO-d₆): δ 8.77 (s br 2H); 7.37–7.25 (m, 3H); 7.21 (d, 2H); 5.40 (s, 2H); 3.80 (t, 2H); 3.21 (s br 4H); 1.53 (q, 2H); 0.83.(t, 3H).

Example 60

General Procedure (B)

7-Benzyl-8-[1,4]diazepan-1-yl-3-methyl-1-propyl-3,7-dihydro-purine-2,6-dione. TFA

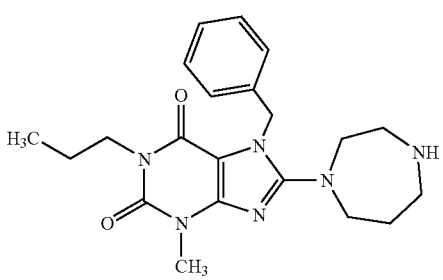

¹H-NMR (DMSO-d₆): δ 8.66 (s br, 2H); 7.40–7.25 (m, 3H); 7.12 (d, 2H); 5.46 (s, 2H); 3.80 (t, 2H); 3.66 (m, 2H); 3.50 (m, 2H); 3.28 (m, 2H); 3.17 (s br, 2H); 1.99 (m, 2H); 1.53 (q, 2H); 0.83 (t, 3H).

Example 61

General Procedure (B)

7-Benzyl-3-methyl-8-piperazin-1-yl-3,7-dihydro-purine-2,6-dione. TFA

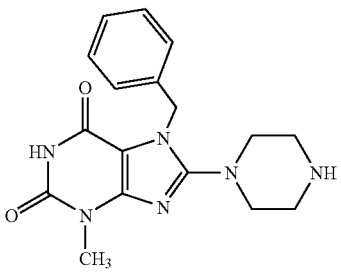

¹H-NMR (DMSO-d₆): δ 10.97 (s, 1H); 8.66 (s br) 7.40–7.25 (m, 3H); 7.21 (d, 2H); 5.37 (s, 2H).

Example 62

General Procedure (B)

7-Benzyl-8-[1,4]diazepan-1-yl-3-methyl-3,7-dihydro-purine-2,6-dione. TFA

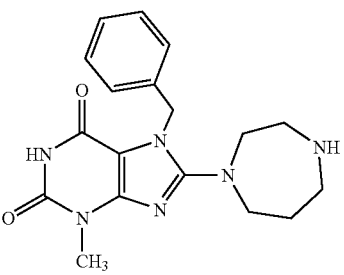

¹H-NMR (DMSO-d₆): δ 10.84 (s, 1H); 8.61 (s br 2H); 7.40–7.25 (m, 3H); 7.13 (d, 2H); 5.43 (s, 2H); 3.65 (m, 2H); 3.47 (m, 2H); 3.17 (m, 2H); 1.98 (m, 2H).

Example 63

General Procedure (B)

2-(3-Methyl-2,6-dioxo-8-piperazin-1-yl-1-propyl-1,2,3,6-tetrahydro-purin-7-ylmethyl)-benzonitrile

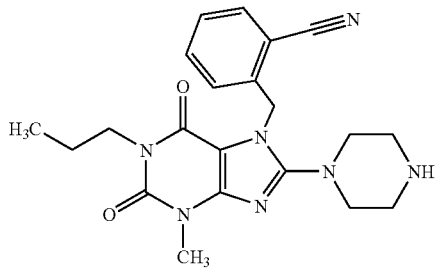

¹H-NMR (DMSO-d₆): δ 8.78 (s br 2H); 7.88 (d, 1H); 7.63 (t, 1H); 7.49 (t, 1H); 7.08 (d, 1H); 5.55 (s, 2H); 3.73 (t, 2H); 3.22 (s br, 4H); 1.47 (q, 2H); 0.78 (t, 3H).

Example 64

General Procedure (B)

2-(8-[1,4]Diazepan-1-yl-3-methyl-2,6-dioxo-1-propyl-1,2,3,6-tetrahydro-purin-7-ylmethyl)-benzonitrile

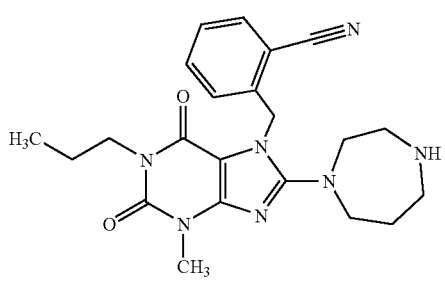

¹H-NMR (DMSO-d₆): δ 8.66 (s br, 2H); 7.89 (d, 1H); 7.65 (t, 1H); 7.50 (t, 1H); 7.06 (d, 1H); 5.58 (s, 2H); 3.73 (t, 2H); 3.69 (m, 2H); 3.47 (m, 2H); 3.42 (s, 3H); 3.21 (m, 2H); 2.00 (m, 2H); 1.48 (sextet, 2H); 0.78 (t, 3H).

Example 65

General Procedure (B)

2-(8-[1,4]Diazepan-1-yl-3-methyl-2,6-dioxo-1,2,3,6-tetrahydro-purin-7-ylmethyl)-benzonitrile

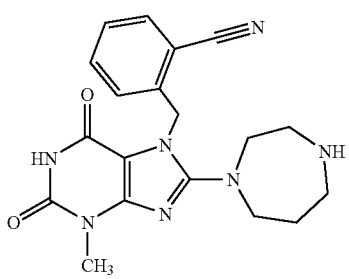

¹H-NMR (DMSO-d₆): δ 10.84 (s, 1H); 8.94 (s br, 1H); 8.69 (s br, 1H); 7.89 (d, 1H); 7.66 (t, 1H); 7.50 (t, 1H); 7.06 (d, 1H); 5.56 (s, 2H); 3.68 (m, 2H); 3.46 (m, 2H); 3.42 (s, 3H).

Example 66

General Procedure (B)

7-(2-Iodo-benzyl)-3-methyl-8-piperazin-1-yl-1-propyl-3,7-dihydro-purine-2,6-dione. TFA

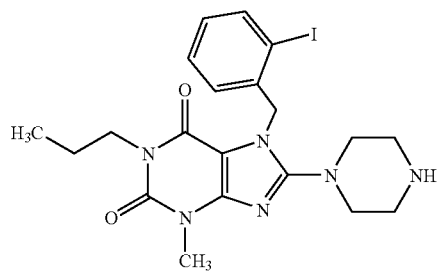

$^1$H-NMR (DMSO-d$_6$): δ 8.73 (s br, 2H); 7.92 (d, 1H); 7.33 (t, 1H); 7.07 (t, 1H); 6.70 (d, 1H); 5.28 (s, 2H); 3.75 (t, 2H); 3.44 (s, 3H); 3.17 (s br, 4H); 1.49 (sextet, 2H); 0.80 (t, 3H).

Example 67

General Procedure (B)

8-[1,4]Diazepan-1-yl-7-(2-iodo-benzyl)-3-methyl-1-propyl-3,7-dihydro-purine-2,6-dione. TFA:

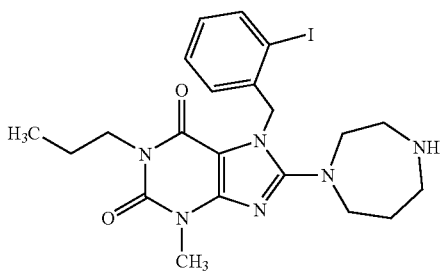

$^1$H-NMR (DMSO-d$_6$): δ 8.66 (s br, 2H); 7.93 (d, 1H); 7.35 (t, 1H); 7.08 (t, 1H); 6.69 (d, 1H); 5.30 (s, 2H); 3.75 (t, 2H); 3.43 (s, 3H); 3.28 (m, 2H); 3.17 (m, 2H); 1.95 (m, 2H); 1.50 (sextet, 2H); 0.81 (t, 3H).,

Example 68

General Procedure (B)

7-(2-Iodo-benzyl)-3-methyl-8-piperazin-1-yl-3,7-dihydro-purine-2,6-dione. TFA

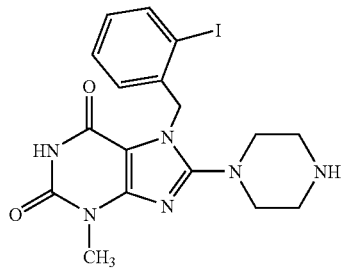

$^1$H-NMR (DMSO-d$_6$): δ 10.96 (s, 1H); 8.72 (s br); 7.72 (d, 1H); 7.34 (t, 1H); 7.07 (t, 1H); 6.73 (d, 1H); 5.26 (s, 2H); 3.15 (m, 4H).

Example 69

General Procedure (B)

8-[1,4]Diazepan-1-yl-7-(2-iodo-benzyl)-3-methyl-3,7-dihydro-purine-2,6-dione. TFA

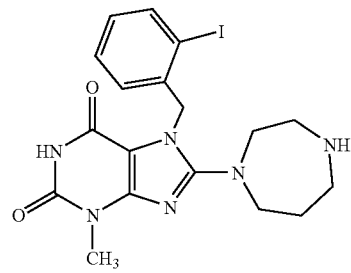

$^1$H-NMR (DMSO-d$_6$): δ 10.84 (s, 1H); 8:62 (s br, 2H); 7.93 (d, 1H); 7.36 (t, 1H); 7.08 (t, 1H); 6.69 (d, 1H); 5.28 (s, 2H); 3.65 (dm, 2H); 3.39 (m, 2H); 3.36 (s, 3H); 3.16 (m, 2H); 1.94 (m, 2H).

Example 70

General Procedure (B)

3-Benzyl-8-[1,4]diazepan-1-yl-1-(3-hydroxy-propyl)-7-(2-iodo-benzyl)-3,7-dihydro-purine-2,6-dione. TFA

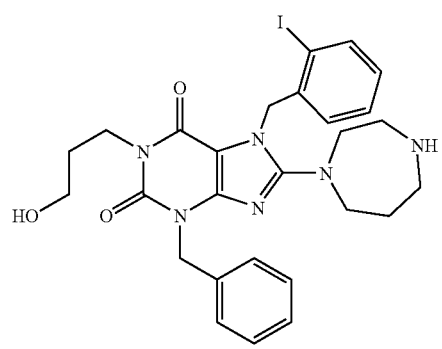

$^1$H-NMR (DMSO-d$_6$): δ (Selected peaks) 8.62 (s br, 2H); 7.88 (d, 1H); 7.40–7.20 (m, 7H); 7.04 (t, 1H); 6.71 (d, 1H); 5.23 (s, 2H); 5.10 (s, 2H),

Example 71

General Procedure (B)

3-Benzyl-8-[1,4]diazepan-1-yl-1-(2-ethoxy-ethyl)-7-(2-iodo-benzyl)-3,7-dihydro-purine-2,6-dione. TFA

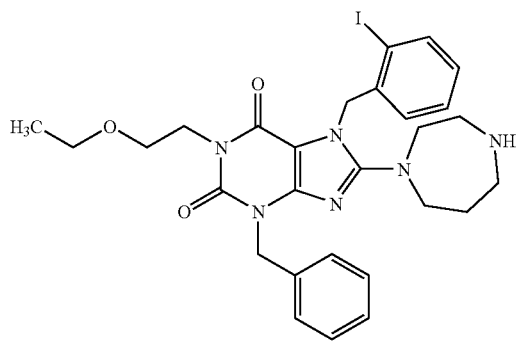

$^1$H-NMR (DMSO-d$_6$): δ (Selected peaks) 8.62 (s br, 2H); 7.88 (d, 1H); 7.40–7.20 (m, 7H); 7.04 (t, 1H); 6.71 (d, 1H); 5.24 (s, 2H); 5.101 (s, 2H); 0.93 (t, 3H).

Example 72

General Procedure (B)

7-Benzyl-8-[1,4]diazepan-1-yl-3-methyl-1-(3-phenyl-allyl)-3,7-dihydro-purine-2,6-dione. TFA

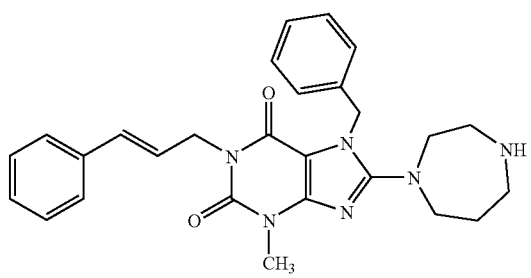

$^1$H-NMR (DMSO-d$_6$): 58.66 (s br, 2H); 7.50–7.20 (m) 7.14 (d, 2H); 6.46 (d, 1H); 6.27 (dt, 1H); 5.47 (s, 2H); 4.61 (d, 2H); 3.67 (m, 2H); 3.50 (m, 2H); 3.43 (s, 3H); 3.17 (m, 2H); 2.00 (m, 2H).

Example 73

General Procedure (B)

7-Benzyl-8-[1,4]diazepan-1-yl-3-methyl-1-(3-phenylallyl)-3,7-dihydropurine-2,6-dione. TFA

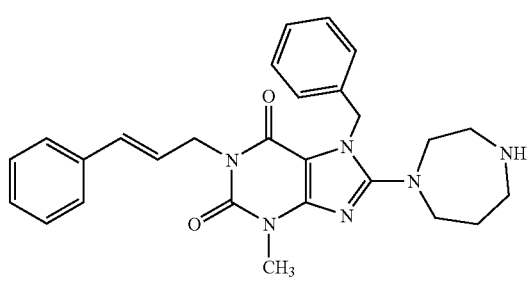

$^1$H-NMR (DMSO-d$_6$): δ 8.66 (s br, 2H); 7.50–7.20 (m) 7.14 (d, 2H); 6.46 (d, 1H); 6.27 (dt, 1H); 5.47 (s, 2H); 4.61 (d, 2H); 3.67 (m, 2H); 3.50 (m, 2H); 3.43 (s, 3H); 3.17 (m, 2H); 2.00 (m, 2H).

Example 74

General Procedure (B)

7-Benzyl-8-[1,4]diazepan-1-yl-3-methyl-1-(2-oxo-2-phenyl-ethyl)-3,7-dihydro-purine-2,6-dione. TFA

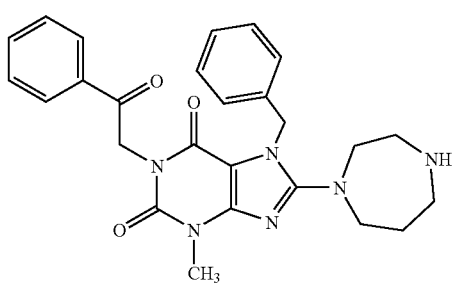

$^1$H-NMR (DMSO-d$_6$): δ 8.62 (s br, 2H); 8.05 (d, 2H); 7.71 (t, 1H); 7.58 (t, 2H); 7.40–7.25 (m, 3H); 7.13 (d, 3H) 5.46 (s, 2H); 5.35 (s, 2H); 3.71 (m, 2H); 3.53 (m, 2H); 3.44 (s, 3H); 3–20 (m, 2H); 2.01 (m, 2H).

Example 75

General Procedure (B)

2-(7-Benzyl-8-[1,4]diazepan-1-yl-3-methyl-2,6-dioxo-2,3,6,7-tetrahydro-purin-1-ylmethyl)-benzonitrile

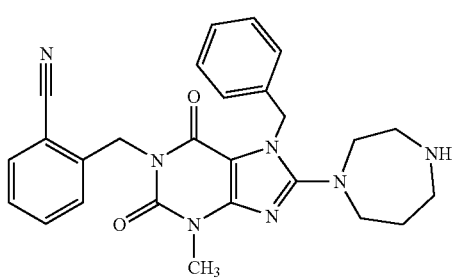

$^1$H-NMR (DMSO-d$_6$): δ 8.66 (s br, 2H); 7.81 (d, 1H); 7.61 (t, 1H); 7.44 (t, 1H); 7.40–7.25 (m, 3H); 7.18 (d, 1H); 7.14 (d, 2H); 5.46 (s, 2H); 5.21 (s, 2H); 3.69 (m, 2H); 3.52 (m, 2H); 3.42 (s, 3H); 3.20 (m, 2H); 2.00 (m, 2H).

Example 76

General Procedure (B)

(7-Benzyl-8-[1,4]diazepan-1-yl-3-methyl-2,6-dioxo-2,3,6,7-tetrahydro-purin-1-yl)-acetonitrile

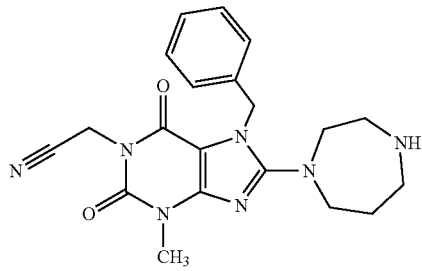

$^1$H-NMR (DMSO-$d_6$): δ 8.66 (s br, 2H); 7.40–7.25 (m, 3H); 5.46 (s, 2H); 4.84 (s, 2H); 3.69 (m, 2H); 3.52 (m, 2H); 3.44. (s, 3H); 3.17 (m, 2H); 1.99 (m, 2H).

Example 77

General Procedure (B)

3-Methyl-7-(2-methyl-thiazol-4-ylmethyl)-8-piperazin-1-yl-3,7-dihydro-purine-2,6-dione.

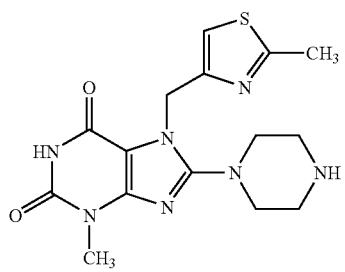

$^1$H-NMR (DMSO-$d_6$): δ 10.99 (s, 1H); 8.88 (s br, 2H)i 7.31 (s, 1H); 5.36 (s, 2H); 3.42 (m, 4H); 3.32 (s, 3H); 3.22 (s br, 4H); 2.60 (s, 3H)

Example 78

General Procedure (B)

8-[1,4]Diazepan-1-yl-3-methyl-7-(2-methyl-thiazol-4-yl-methyl)-3,7-dihydro-purine-2,6-dione. TFA

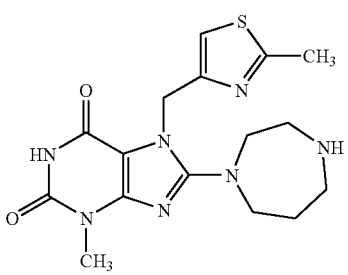

$^1$H-NMR (DMSO-$d_6$): δ 10.87 (s, 1H); 8.88 (s br, 2H); 7.21 (s, 1H); 5.41 (s, 2H); 3.73 (m, 2H); 3.57 (t, 2H); 3.31 (s br, 4H); 3.23 (s br, 2H); 2.61 (s.3H); 2,51 (m,1H); 2.04 (m, 2H); HPLC-MS m/z=376

Example 79

General Procedure (B)

3-Methyl-7-(2-oxo-2-phenyl-ethyl)-8-piperazin-1-yl-3,7-dihydro-purine-2,6-dione. TFA

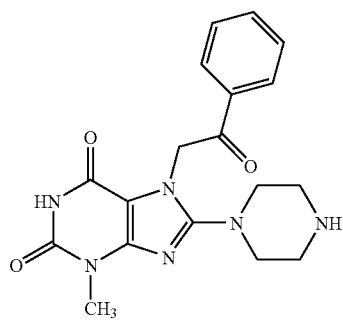

$^1$H-NMR (DMSO-$d_6$): δ 11.00 (s, 1H); 9.89 (s br, 2H); 8.07 (d, 2H); 7.74 (t, 1H); 7.64 (t, 2H); 5.75 (s, 2H); 3.36 (s, 3H); 3.29 (m, 4H); 3.24 (m, 4H). HPLC-MS m/z=369

Example 80

General Procedure (B)

8-[1,4]Diazepan-1-yl-3-methyl-7-(2-oxo-2-phenyl-ethyl)-3,7-dihydro-purine-2,6-dione. TFA

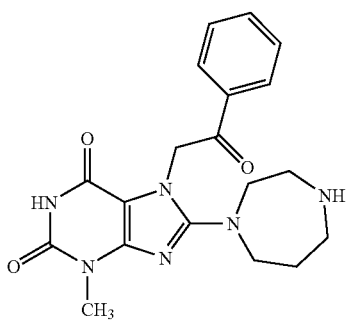

$^1$H-NMR (DMSO-$d_6$): δ 10.88 (s, 1H); 8.87 (s br, 2H); 8.09–7.60 (m, 5H); 5.80 (s, 2H); 3.67 (t, 2H); 3.46 (t, 2H); 3.34 (s, 3H); 3.21 (t, 2H); 2.01 (m, 2H). HPLC-MS m/z=383

Example 81

General Procedure (B)

8-[1,4]Diazepan-1-yl-3-methyl-7-phenethyl-3,7-dihydro-purine-2,6-dione. TFA

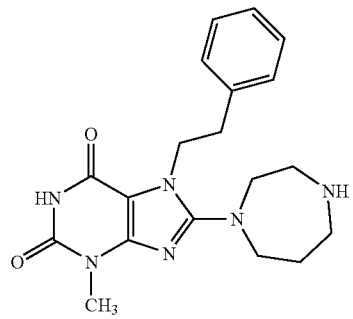

$^1$H-NMR (DMSO-d$_6$): S10.89 (s, 1H); 8.87 (s br, 2H); 7.29–7.12 (m, 5H); 4.29 (t, 2H); 3.54 (m, 2H); 3.42 (t, 2H); 3.28 (s, 3H); 3,21 (s br, 2H); 3.00 (t, 2H) 2.03 (m, 2H). HPLC-MS m/z=369,

Example 82

General Procedure (B)

8-[1,4]Diazepan-1-yl-1-(3-hydroxy-propyl)-7-(2-iodo-benzyl)-3-methyl-3,7-dihydro-purine-2,6-dione. TFA

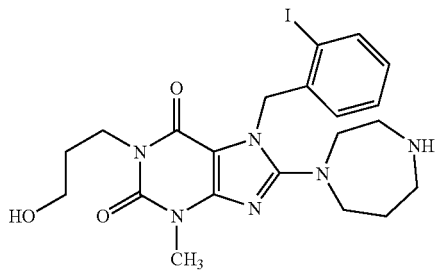

$^1$H-NMR (DMSO-d$_6$): δ 8.72 (s br, 2H); 7.93 (d, 1H); 7.35 (t, 1H); 7.08 (t, 1H); 6.70 (d, 1H); 5.29 (s, 2H); 3.84 (t, 2H); 3.66 (m, 2H); 3.43 (s, 3H); 3.42–3.33 (m, 4H).3.27 (m, 2H); 3.15 (m, 2H); 1.94 (m, 2H); 1.62 (q, 2H); HPLC-MS (Method C): m/z 539 (M+1); R$_t$=3.69 min

Example 83

General Procedure (B)

1-(3-Hydroxy-propyl)-7-(2-iodo-benzyl)-3-methyl-8-piperazin-1-yl-3,7-dihydro-purine-2,6-dione. TFA

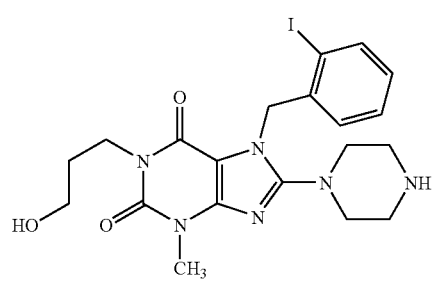

$^1$H-NMR (DMSO-d$_6$): δ 8.80 (s br2H); 7.92 (d, 1H); 7.33 (t, 1H); 7.07 (t, 1H); 6.71 (d, 1H); 5.27 (s, 2H); 3.83 (t, 2H); 3.44 (s, 3H); 3.37 (t, 2H); 3.29 (m, 2H); 3.16 (m, 2H); 1.62 (q, 2H); HPLC-MS (Method C): m/z=525 (M+1); R$_t$=3.53 min

Example 84

General Procedure (B)

8-[1,4]Diazepan-1-yl-1-(2-ethoxy-ethyl)-7-(2-iodo-benzyl)-3-methyl-3,7-dihydro-purine-2,6-dione. TFA

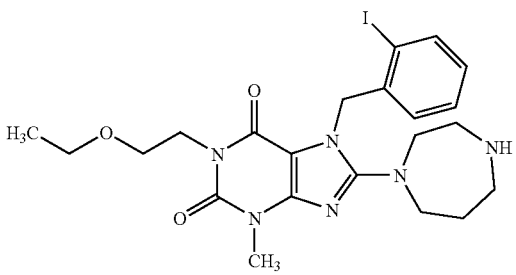

$^1$H-NMR (DMSO-d$_6$): δ 8.64 (s br 2H); 7.93 (d, 1H); 7.35 (t, 1H); 7.08 (t, 1H); 6.69 (d, 1H); 5.28 (s, 2H); 3.96 (t, 2H); 3.66 (m, 2H); 3.16 (m, 2H); 3.43 (s, 3H); 1.01_(t, 3H). HPLC-MS (Method C): m/z=553 (M+1); R$_t$=4.09 min

Example 85

General Procedure (B)

1-(2-Ethoxy-ethyl)-7-(2-iodo-benzyl)-3-methyl-8-piperazin-1-yl-3,7-dihydro-purine-2,6-dione. TFA

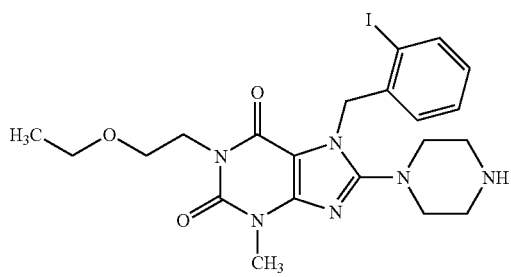

$^1$H-NMR (DMSO-d$_6$): δ 8.80 (s br, 2H); 7.92 (d, 1H); 7.32 (t, 1H); 7.07 (t, 1 H); 6.70 (d, 1H); 5.27 (s, 2H); 3.96 (t, 1H); 3.48–3.40 (m, 5H); 3.38 (q, 2H); 3.30 (m, 4H); 3.16 (m, 4H); 1.00 (t, 3H). HPLC-MS (Method C): m/z=539 (M+1); R$_t$=4.03 min

Example 86

General Procedure (B)

8-[1,4]Diazepan-1-yl-7-(2-iodo-benzyl)-3-methyl-1-(2-phenoxy-ethyl)-3,7-dihydro-purine-2,6-dione. TFA.

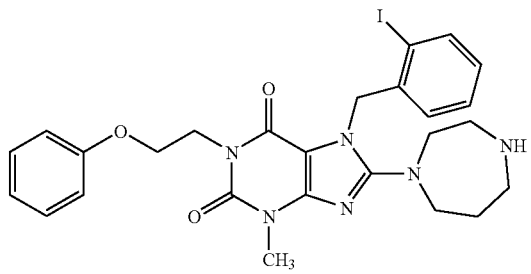

HPLC-MS (Method C): m/z=601 (M+1); $R_t$=4.73 min

Example 87

General Procedure (B)

8-[1,4]Diazepan-1-yl-7-(2-iodo-benzyl)-1-[2-(2-methoxy-ethoxy)-ethyl]-3-methyl-3,7-dihydro-purine-2,6-dione. TFA

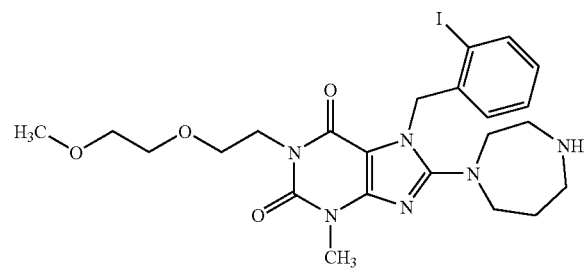

$^1$H-NMR (DMSO-$d_6$): δ 8.70 (s br, 2H); 7.93 (d, 1H); 7.35 (t, 1H); 7.08 (t, 1H); 6.70 (d, 1H); 5.29 (s, 2H); 3.96 (t, 2H); 3.66 (m, 2H); (3.52–3.44 (m, 4H); 3.43 (s, 3H); 3.42–3.37 (m, 2H); 3.36–3.31 (m, 2H); 3.26 (m, 2H); 3.20 (m, 5H); 1.94 (m, 2H). HPLC-MS (Method C): m/z=583 (M+1); R=3.96 min

Example 88

General Procedure (B)

7-(2-Iodo-benzyl)-1-[2-(2-methoxy-ethoxy)-ethyl]-3-methyl-8-piperazin-1-yl-3,7-dihydro-purine-2,6-dione. TFA

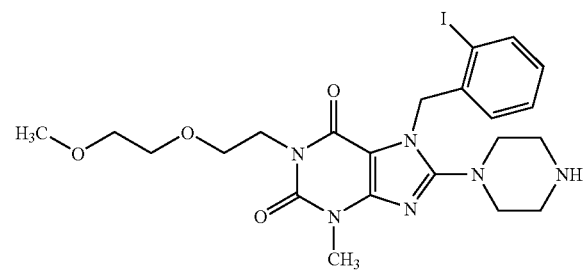

$^1$H-NMR (DMSO-$d_6$): δ 8.78 (s br, 2H); 7.93 (d, 1H); 7.33 (t, 1H); 7.07 (t, 1H); 6.70 (t, 1H); 5.27 (s, 2H); 3.96 (t, 2H); 3.52–3.42 (m, 4); 3.44 (s, 3H); 3.38–3.27 (m, 6H); 3.20–3.12 (m, 4H) 3.18 (s, 3H). HPLC-MS (Method C): m/z=569 (M+1); $R_t$=3.86 min

Example 89

General procedure (B)

8-[1,4]Diazepan-1-yl-1-(3,5-dimethoxy-benzyl)-7-(2-iodo-benzyl)-3-methyl-3,7-dihydro-purine-2,6-dione. TFA

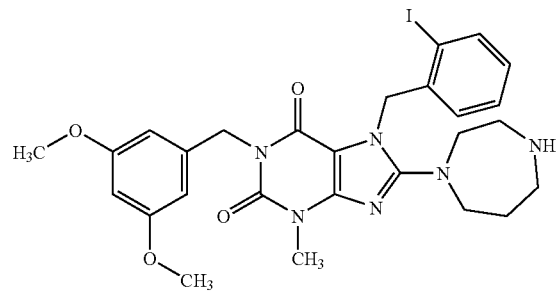

$^1$H-NMR (DMSO-$d_6$): δ 8.70 (s br, 2H); 7.91 (d, 1H); 7.34 (t, 1H); 7.07 (t, 1H); 6.74 (d, 1H); 6.34 (m, 1H); 6.32 (m, 2H); 5.30 (s, 2H); 4.91 (s, 2H); 3.69 (m, 2H); 3.66 (s, 6H); 3.44 (s, 3H); 3.42 (m, 2H); 3.28 (m, 2H); 3.17 (m, 2H); 1.95 (m, 2H). HPLC-MS (Method C): m/z=631 (M+1); R=4.72 min

Example 90

General Procedure (B)

8-[1,4]Diazepan-1-yl-7-(2-iodo-benzyl)-1-(3-methoxy-benzyl)-3-methyl-3,7-dihydro-purine-2,6-dione. TFA

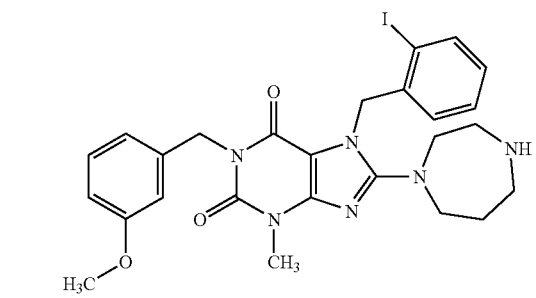

$^1$H-NMR (DMSO-$d_6$): δ 8.70 (s br, 2H); 7.93 (d, 1H); 7.35 (t, 1H); 7.18 (t, 1H); 7.08 (t, 1H); 6.80–6.70 (m, 4H); 5.30 (s, 2H); 4.95 (s, 2H); 3.68 (s, 3H); 3.44 (s, 3H); 3.42 (m, 2H); 3.28 (m, 2H); 3.16 (m, 2H); 1.95 (m, 2H). HPLC-MS (Method C): m/z=601 (M+1); $R_t$=4.62 min

Example 91

General Procedure (B)

7-Biphenyl-2-ylmethyl-8-[1,4]diazepan-1-yl-3-methyl-3,7-dihydro-purine-2,6-dione. TFA

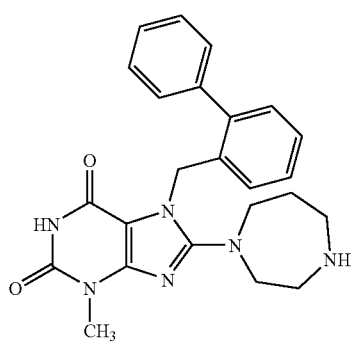

¹H-NMR (DMSO-d₆): δ 10.81 (s, 1H); 8.74 (s br, 2H); 7,5–7.22 (m, 9H); 5.35 (s, 2H); 5.53 (t, 2H); 3.29 (s, 3H); 3.26 (m, 2H); 3.15 (s br, 2H); 3.06 (s br, 2H); 1.82 (m, 2H)HPLC-MS m/z=431

Example 92

General Procedure (B)

7-(2-Bromo-benzyl)-8-[1,4]diazepan-1-yl-3-methyl-3,7-dihydro-purine-2,6-dione. TFA

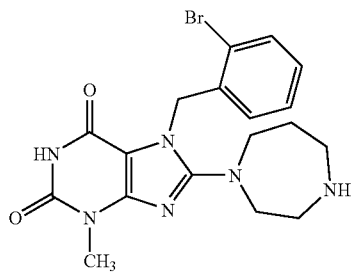

¹H-NMR (DMSO-d₆): δ 10.89 (s, 1H); 8.8 (s br, 2H); 7.74–6.74 (m, 4H); 5.37 (s, 2H); 3.66 (m, 2H); 3.40 (t, 2H); 3.35 (s, 3H); 3.26 (s br, 2H); 3.16 (s br, 2H); HPLC-MS m/z 435.

Example 93

General Procedure (B)

7-(2-Chloro-benzyl)-8-[1,4]diazepan-1-yl-3-methyl-3,7-dihydro-purine-2,6-dione. TFA

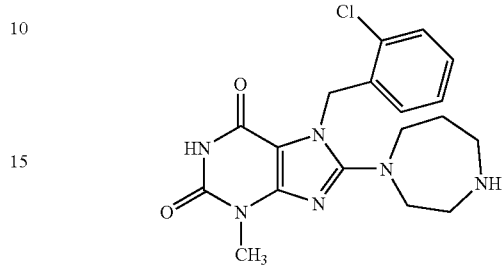

¹H-NMR (DMSO-d₆): δ 10.88 (s, 1H); 8.83 (s br, 2H); 7.55–7.47 (m, 1H) 7.42–7.25 (m, 2H) 6.87–6.78 (m 1H); 5.43 (s, 2H); 3.66 (t, 2H); 3.41 (t, 2H); 3.35 (s, 3H); 3.27 (s br, 2H); 3.16 (s br, 2H); 1.95 (m, 2H). HPLC-MS m/z=389

Example 94

General Procedure (C)

7-Benzyl-8-(3,5-dimethyl-piperazin-1-yl)-1,3-dimethyl-3,7-dihydro-purine-2,6-dione. 2HCl

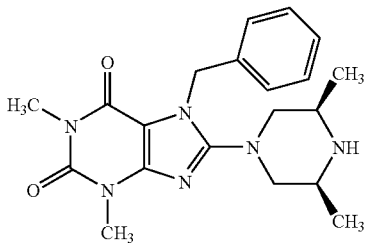

HPLC-MS (Method B): m/z=383 (m+1); R_t=1.91 min.

Example 95

General Procedure (A)

7-(4-Methoxybenzyl)-1,3-dimethyl-8-piperazin-1-yl-3,7-dihydropurine-2,6-dione. TFA

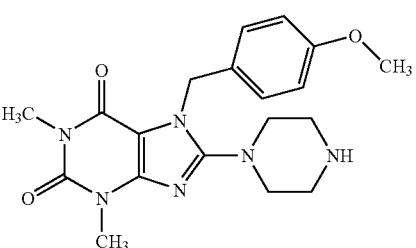

HPLC-MS (Method C) m/z=384 (M+1); R_t=1.24 min.

Example 96

General Procedure (A)

(1,3-Dimethyl-2,6-dioxo-8-piperazin-1-yl-1,2,3,6-tetrahydropurin-7-yl)-phenylacetic acid methyl ester. TFA

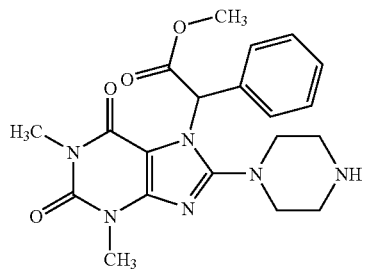

HPLC-MS (Method C): m/z=413 (M+1); $R_t$=1.31 min.

Example 97

General Procedure (A)

7-(5-Chloro-2-nitrobenzyl)-1,3-dimethyl-8-piperazin-1-yl-3,7-dihydropurine-2,6-dione. TFA

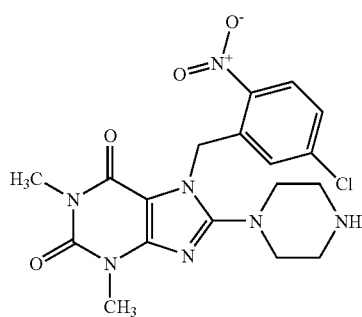

HPLC-MS (Method C): m/z=434 (M+1); $R_t$=2.53 min. Purity 100% (ELS)

Example 98

General Procedure (A)

4-(1,3-Dimethyl-2,6-dioxo-8-piperazin-1-yl-1,2,3,6-tetrahydropurin-7-ylmethyl) benzonitrile. TFA

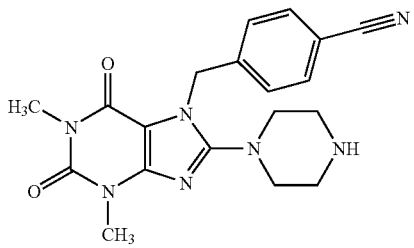

HPLC-MS (Method C) m/z=380 (M+1); $R_t$=1.21 min.

Example 99

General Procedure (A)

7-(4-Methanesulfonylbenzyl)-1,3-dimethyl-8-piperazin-1-yl-3,7-dihydropurine-2,6-dione. TFA

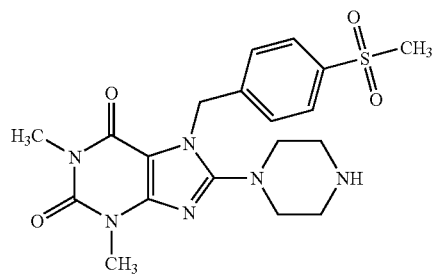

HPLC-MS (Method C) m/z=433 (M+1); $R_t$=1.05 min.

Example 100

General Procedure (A)

7-(2-Fluoro-6-nitrobenzyl)-1,3-dimethyl-8-piperazin-1-yl-3,7-dihydropurine-2,6-dione. TFA

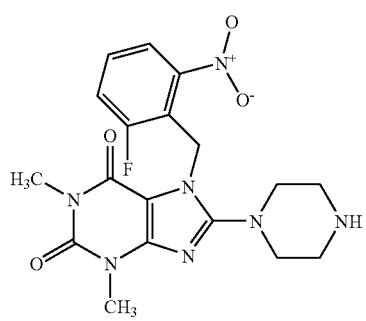

HPLC-MS (Method C) m/z=418(M+1); 1.22 min.

Example 101

General Procedure (A)

7-(4-Benzyloxybenzyl)-1,3-dimethyl-8-piperazin-1-yl-3,7-dihydropurine-2,6-dione. TFA

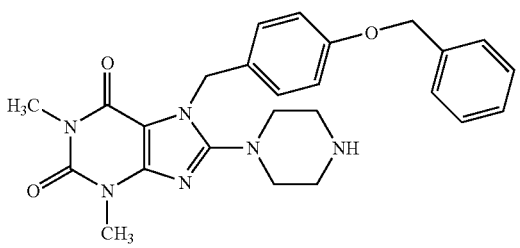

HPLC-MS (Method C) m/z=461 (M+1); $R_t$=1.82 min.

Example 102

General Procedure (A)

7-(2,4-Dichlorobenzyl)-1,3-dimethyl-8-piperazin-1-yl-3,7-dihydropurine-2,6-dione. TFA

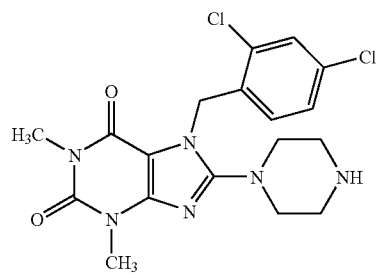

HPLC-MS (Method C) m/z=425 (M+2); $R_t$=1.57 min. (Chlorine isotope signal)

Example 103

General Procedure (A)

1,3-Dimethyl-8-piperazin-1-yl-7-(4-trifluoromethylbenzyl)-3,7-dihydropurine-2,6-dione. TFA

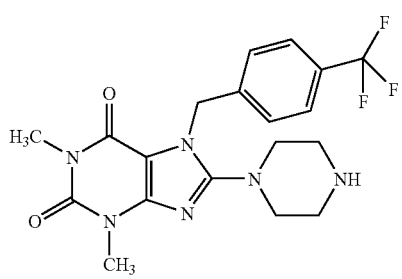

HPLC-MS (Method C) m/z=423 (M+1); $R_t$=1.58 min.

Example 104

General Procedure (A)

7-Biphenyl-4-ylmethyl-1,3-dimethyl-8-piperazin-1-yl-3,7-dihydropurine-2,6-dione. TFA

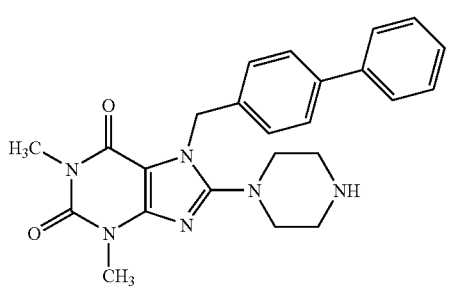

HPLC-MS (Method C) m/z=431 (M+1); $R_t$=1.76 min

Example 105

General Procedure (A)

3-(1,3-Dimethyl-2,6-dioxo-8-piperazin-1-yl-1,2,3,6-tetrahydropurin-7-ylmethyl) benzoic acid methyl ester. TFA

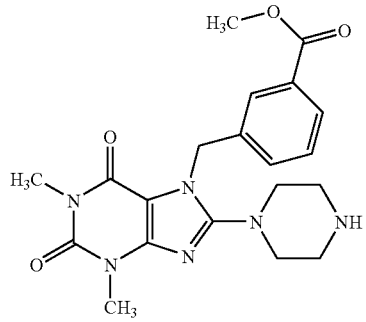

HPLC-MS (Method C) m/z=413 (M+1); $R_t$=1.33 min.

Example 106

General Procedure (A)

4-(1,3-Dimethyl-2,6-dioxo-8-piperazin-11-yl-1,2,3,6-tetrahydropurin-7-ylmethyl) benzoic acid methyl ester. TFA

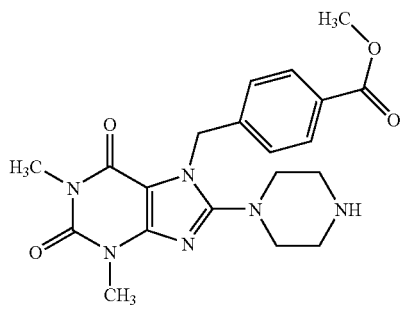

HPLC-MS (Method C) m/z=413 (M+1); $R_t$=1.31 min.

Example 107

General Procedure (A)

7-Biphenyl-2-ylmethyl-1,3-dimethyl-8-piperazin-1-yl-3,7-dihydropurine-2,6-dione. TFA

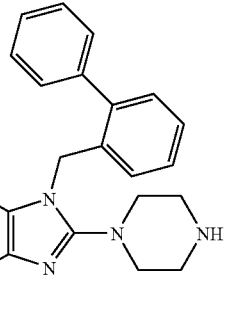

HPLC-MS (Method C) m/z=431 (M+1); $R_t$=1.55 min.

Example 108

General Procedure (A)

7-(4-tert-Butylbenzyl)-1,3-dimethyl-8-piperazin-1-yl-3,7-dihydropurine-2,6-dione. TFA

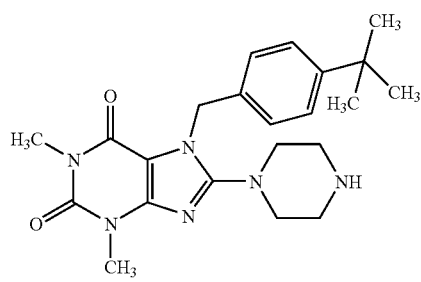

HPLC-MS (Method C) m/z=411 (M+1); $R_t$=1.78 min.

Example 109

General Procedure (A)

1,3-Dimethyl-8-piperazin-1-yl-7-(4-trifluoromethoxybenzyl)-3,7-dihydropurine-2,6-dione. TFA

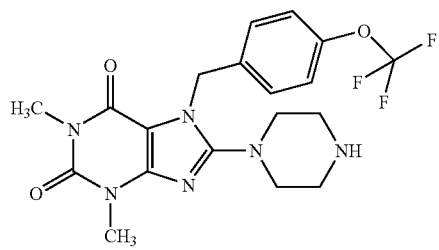

HPLC-MS (Method C) m/z=439 (M+1); $R_t$=1.65 min.

Example 110

General Procedure (A)

7-(3,4-Dichlorobenzyl)-1,3-dimethyl-8-piperazin-1-yl-3,7-dihydropurine-2,6-dione. TFA

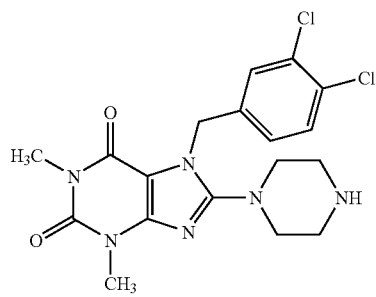

HPLC-MS (Method C) m/z=424 (M+1); $R_t$=2.87 min. Purity 98% (ELS)

Example 111

General Procedure (A)

1,3-Dimethyl-8-piperazin-1-yl-7-(4-[1,2,3]thiadiazol-4-ylbenzyl)-3,7-dihydropurine-2,6-dione. TFA

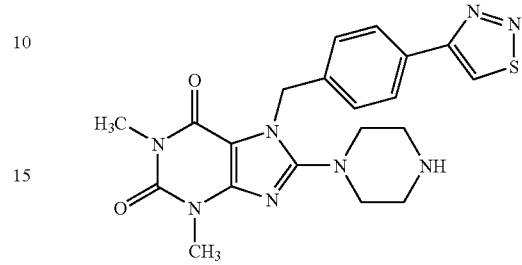

HPLC-MS (Method C) m/z=439 (M+1); $R_t$=2.47 min. Purity 80% (ELS)

Example 112

General Procedure (A)

4-(1,3-Dimethyl-2,6-dioxo-8-piperazin-1-yl-1,2,3,6-tetrahydropurin-7-ylmethyl)-3-methoxybenzoic acid methyl ester. TFA

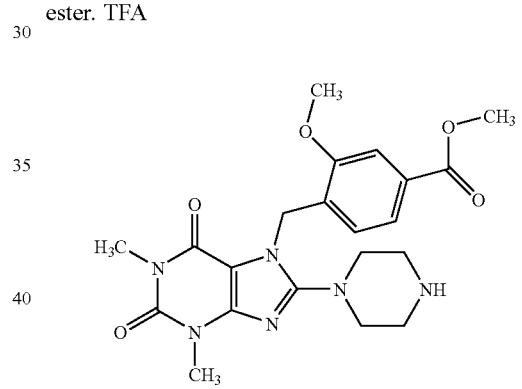

HPLC-MS (Method C) m/z=443 (M+1); $R_t$=2.50 min. Purity >99% (ELS).

Example 113

General Procedure (A)

7-Cyclohexylmethyl-1,3-dimethyl-8-piperazin-1-yl-3,7-dihydro-purine-2,6-dione. TFA

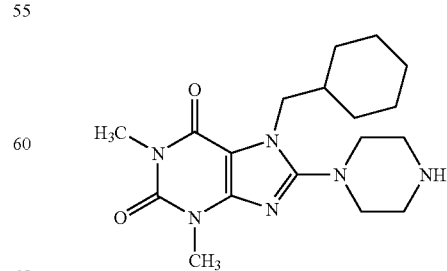

HPLC-MS (Method B): m/z=361 (M+1); $R_t$=2.15 min.

Exampl 114

General Procedure (C)

7-Benzyl-8-(2,5-diaza-bicyclo[2.2.1]hept-2-yl)-1,3-dimethyl-3,7-dihydro-purine-2,6-dione. TFA

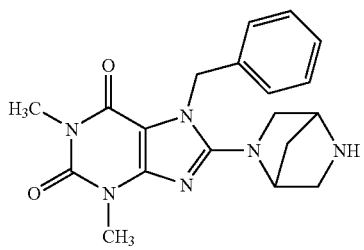

HPLC-MS (Method B): m/z=367; $R_t$=1.76 min. TIC area 100%

Example 115

General Procedure (A)

8-(6-Benzyl-[1,4]diazepan-1-yl)-7-(2-iodo-benzyl)-1,3-dimethyl-3,7-dihydro-purine-2,6-dione. TFA

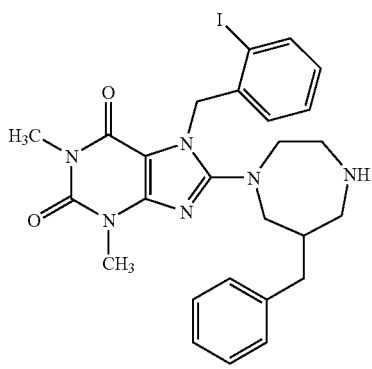

HPLC-MS (Method B): m/z=585 (M+1); $R_t$=2.87 min; purity ~50%

Example 116

General Procedure (A)

(S)-7-Benzyl-8-(3-hydroxymethylpiperazin-1-yl)-1,3-dimethyl-3,7-dihydropurine-2,6-dione

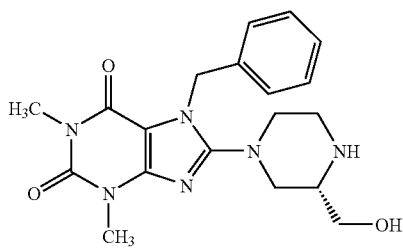

The piperazine moiety was prepared according to the general procedure for preparation of piperazine derivatives.

MeOH-d4; d=7.1–7.4 (m; 5H); 5.4 (d; 2H); 3.5 (s; 3H); 3.45 (m; 2H); 3.25 (s; 3H); 2.9–3.2 (m; 3H); 2.0 (m; 1H); 1.2 (s br; 3H). HPLC-MS (Method B): m/z=385 (M+1); $R_t$=1.65 min.

Example 117

General Procedure (C)

8-[1,4]Diazepan-1-yl-1,3-dimethyl-7-(2-oxo-2-pyrrolidin-1-yl-ethyl)-3,7-dihydro-purine-2,6-dione

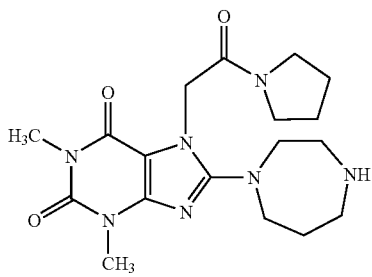

HPLC-MS (Method B): m/z=390; $R_t$=2.93 min+0.43 min; 43+56%

Example 118

General Procedure (C)

7-(2-Iodo-benzyl)-1,3-dimethyl-8-(6-pyridin-2-ylmethyl-[1,4]diazepan-1-yl)-3,7-dihydro-purine-2,6-dione. TFA

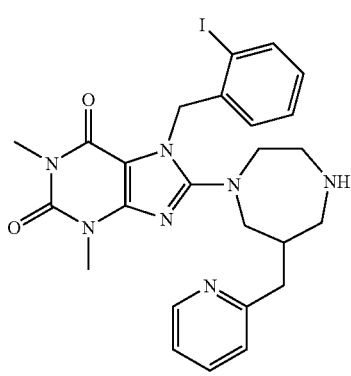

$^1$H NMR (CDCl3): δ 8.9 (s br, 2H); 8.65 (d, 1H); 8.2 (t, 1H); 7.85 (d, 1H); 7.15 (t, 1H); 7.5 (d, 1H); 7.3 (t, 1H); 7.0 (t, 1H); 6.75 (d, 1H); 5.45 (s, 2H); 3.05–3.8 (m, 3H); 3.5 (s, 3H); 3.3 (s, 4H); 2.8–3.25 (m, 7H). HPLC-MS (Method B): m/z=586 (M+1); $R_t$=2.25 min; Purity (UV)=97%.

Example 119

General Procedure (A)

7-(2-Bromo-benzyl)-1,3-dimethyl-8-(6-pyridin-2-ylmethyl-[1,4]diazepan-1-yl)-3,7-dihydro-purine-2,6-dione

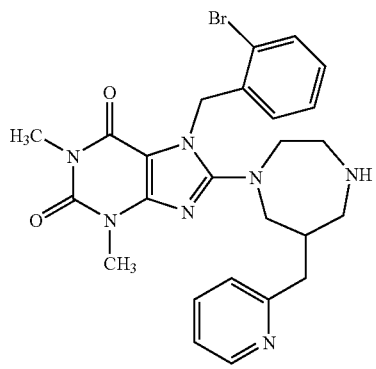

HPLC-MS (Method B): m/z=538 & 541 (M+1; M+2); $R_t$=1.94 min

Example 120

General Procedure (D)

(S) 7-Benzyl-8-(3-benzyl-piperazin-1-yl)-1,3-dimethyl-3,7-dihydro-purine-2,6-dione

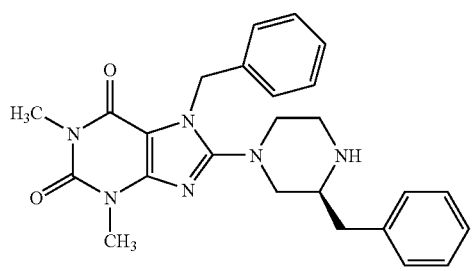

$^1$H-NMR (CDCl$_3$): δ 7.24(m, 10H); 5.32(m, 2H); 3.52(s, 3H); 3.11 (m, 11H); 2.68(m, 2H).
HPLC-MS (Method B): m/z=445 (M+1), 354, 263; $R_t$=4.13

Example 121

General Procedure (D)

7-Benzyl-1,3-dimethyl-8-(3-phenethyl-piperazin-1-yl)-3,7-dihydro-purine-2,6-dione

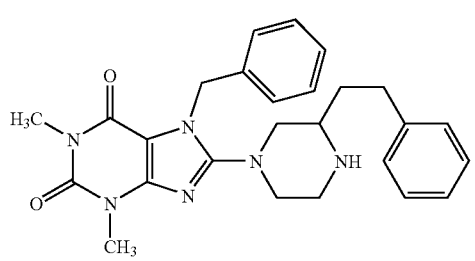

$^1$H-NMR (DMSO-d$_6$): δ 7.25(m, 10H); 5.41 (s, 2H); 3.30(m, 15SH); 1.88(m, 2H). HPLC-MS. (Method B): m/z=481 (M+Na), 459/460(M+1); $R_t$=2.52 min.

Example 122

General Procedure (D)

(R)-7-Benzyl-8-(3-benzylpiperazin-1-yl)-1,3-dimethyl-3,7-dihydropurine-2,6-dione

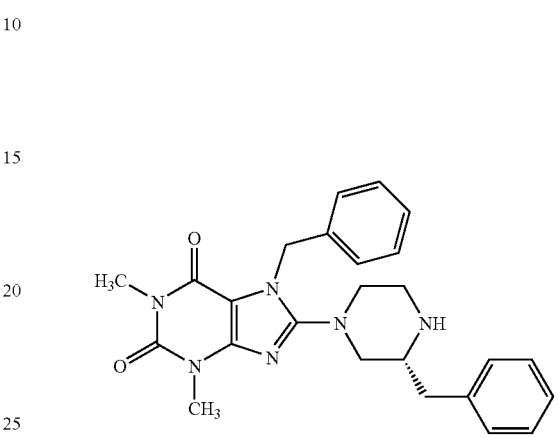

$^1$H-NMR (CDCl$_3$): δ 7.24(m, 10H); 5.34(m, 2H); 3.55(s, 3H); 3.34(m, 5H); 2.78(m, 7H); 1.70(s, 1H). HPLC-MS (Method B): m/z=445/446(M+1), 468(M+Na); $R_t$=2,56 min.

Example 123

General Procedure (D)

7-Benzyl-8-(3-(2-hydroxy-benzyl)-piperazin-1-yl)-1,3-dimethyl-3,7-dihydro-purine-2,6-dione

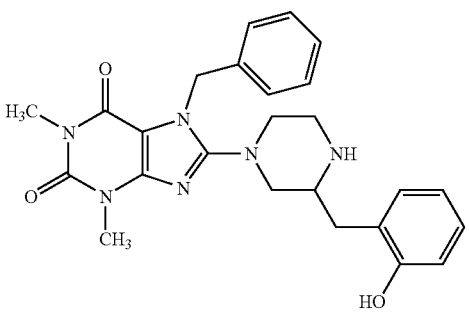

$^1$H-NMR (MeOH-d$_4$): δ 7.28(m, 3H); 7.11(m, 4H); 6.81 (m, 2H); 5.43(m, 2H); 3.70(m, 1H); 3.31(m, 14H); 2.88(s, 2H). HPLC-MS (Method B): m/z=461/462(m+1); 483(M+Na); $R_t$=2,409

Example 124

General Procedure (D)

7-Benzyl-8-(3-(2-methoxy-benzyl)-piperazin-1-yl) 1,3-dimethyl-3,7-dihydro-purine-2,6-dione

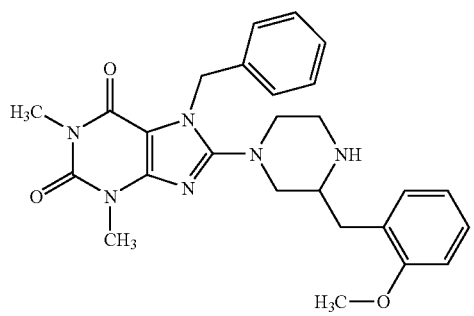

¹H-NMR (CDCl₃): δ 7.22(m, 7H); 6.87(m, 2H); 5.32(m, 2H); 3.83(s, 3H); 3.54(s, 3H); 3.33(m, 5H); 2.79(m, 7H); 1.87(s, 1H)HPLC-MS (Method B): m/z 475,476,477 (M+1); $R_t$=2.57

Example 125

General Procedure (D)

(R) 7-Benzyl-8-(3-(4-methoxy-benzyl)-piperazin-1-yl) 1,3-dimethyl-3,7-dihydro-purine-2,6-dione

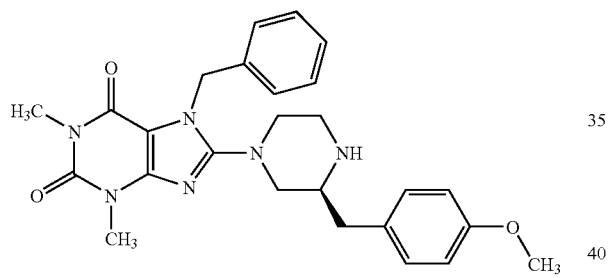

¹H-NMR (CDCl₃): δ 7.25(m, 5H); 7.08(m, 2H); 6.84(m, 2H); 5.34(m, 2H); 3.80(s, 3H); 3.55(s, 3H); 3.38(s, 3H); 3.29(m, 2H); 2.88(m, 5H); 2.52(m, 2H); 1.64(s, 1H)HPLC-MS (Method B): m/z=497(M+1), 475/476/477(M+1); $R_t$=2,368 min

Example 126

General Procedure (D)

(R)-7-Benzyl-8-(3-(4-hydroxy-benzyl)-piperazin-1-yl)-1,3-dimethyl-3,7-dihydro-purine-2,6-dione

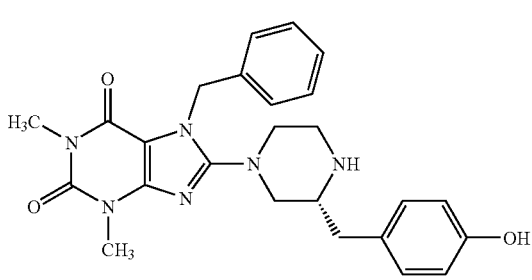

¹H-NMR (DMSO-d₆): δ 9.38(s, 1H); 8.86(s, 2H); 7.29(m, 3H); 7.13(m, 2H); 6.98(m, 2H); 6.72(m, 2H); 5.36(m, 2H); 3.09(m, 15H)HPLC-MS (Method B): m/z=943(2M+Na), 461/462(M+1); $R_t$=2.017

Example 127

General Procedure (D)

(R)-7-Benzyl-1,3-dimethyl-8-(3-(4-nitro-benzyl)-piperazin-1-yl)-3,7-dihydro-purine-2,6-dione

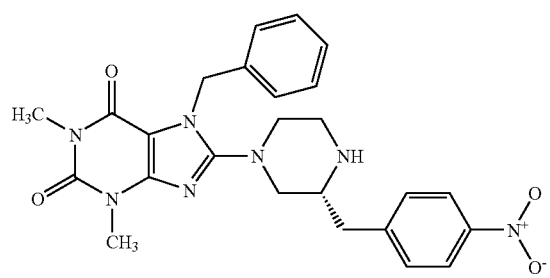

¹H-NMR (CDCl₃): δ 8.17(m, 2H); 7.30(m, 7H); 5.34(s, 2H); 3.55(s, 3H); 3.00(m, 12H) HPLC-MS (Method B): m/z=490/491 (M+1); $R_t$=2.522

Example 128

General Procedure (D)

(R)-7-Benzyl-8-(3-(4-fluoro-benzyl)-piperazin-1-yl)-1,3-dimethyl-3,7-dihydro-purine-2,6-dione

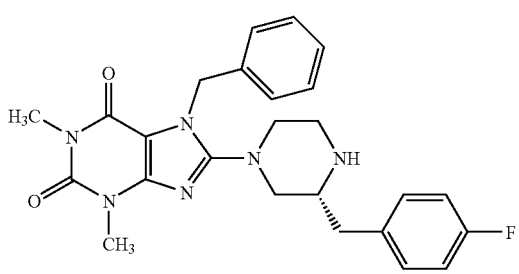

¹H-NMR (CDCl₃): δ 7.32(m, 2H); 7.08(m, 7H); 5.34(m, 2H); 3.55(m, 3H); 2.93(m, 12H) HPLC-MS (Method B): m/z=947(2M+Na), 485(M+Na), 463/464(M+1) $R_t$=2,35 min

Example 129

General Procedure (D)

(R)-4-(4-(7-Benzyl-1,3-dimethyl-2,6-dioxo-2,3,6,7-tetrahydro-1H-purin-8-yl)-piperazin-2-ylmethyl)-benzonitrile

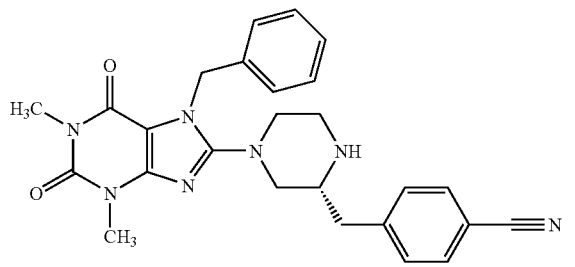

$^1$H-NMR (CDCl$_3$): δ 7.61(m, 2H); 7.26(m, 7H); 5.34(s, 2H); 3.53(s, 3H); 3.28(m, 5H); 2.83(m, 7H)
HPLC-MS (Method B): m/z=492(M+Na), 470/471 (M+1); R$_t$=2.334

Example 130

General Procedure (D)

(R)-6-(8-(3-Benzyl-piperazin-1-yl)-1,3-dimethyl-2,6-dioxo-1,2,3,6-tetrahydro-purin-7-ylmethyl)-nicotinonitrile

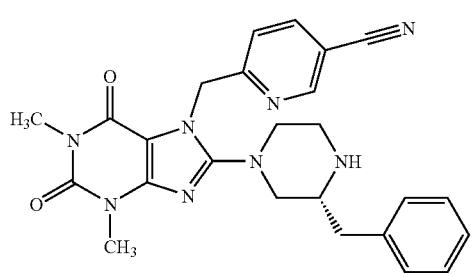

$^1$H-NMR (CDCl$_3$): S8.67(m, 1H); 7.88(m, 1H); 7.22(m, 6H); 5.40(s, 2H); 3.55(m, 3H); 3.33(m, 5H); 2.85(m, 7H)HPLC-MS (Method B): m/z=963(2M+Na), 471/472 (M+1); R.=1.791 min.

Example 131

General Procedure (D)

(R)-7-Benzyl-1,3-dimethyl-8-(3-thiazol-4-ylmethyl-piperazin-1-yl)-3,7-dihydro-purine-2,6-dione

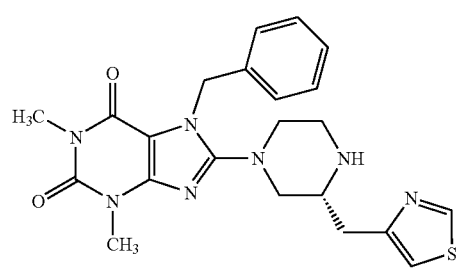

$^1$H-NMR (CDCl$_3$): δ 8.77(m, 1H); 7.26(m, 5H); 7.02(m, 1H); 5.35(m, 2H); 3.54(s, 3H); 2.74(m, 12H)HPLC-MS (Method B): m/z=452/453(M+1) R$_t$=2.220 min.

Example 132

General Procedure (D)

(R)-2-[1,3-Dimethyl-2,6-dioxo-8-(3-thiophen-2-ylmethyl-piperazin-1-yl)-1,2,3,6-tetrahydro-purin-7-ylmethyl]-benzonitrile

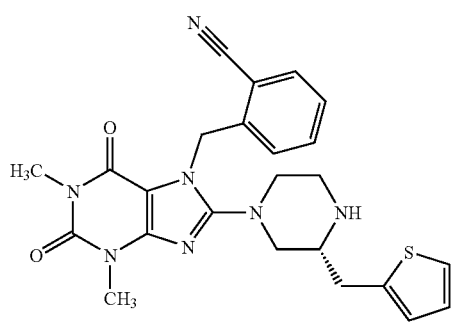

$^1$H-NMR (CDCl$_3$): S7.70(s, 1H); 7.55(s, 1H); 7.40(s, 1H); 7.13(s, 2H); 6.88(s, 3H); 5.56(s, 2H); 3.58(s, 3H); 2.96(m, 12H)HPLC-MS (Method B): Ret.tid=2.40 min. m/z=489(M+Na), 476/477(M+1)

By use of the general methods described above, the following compounds can furthermore be made:

---

Example 133
7-Benzyl-8-[1,4-diazepan-1-yl-3-methyl-1-(tetrahydro-furna-2-ylmethyl)-3,7-dihydro-purine-2,6-dione

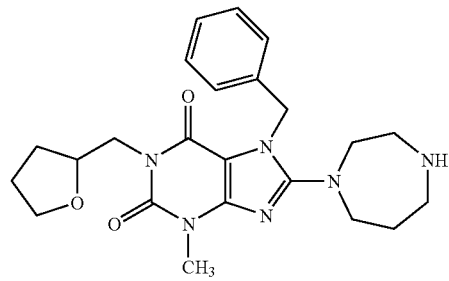

Example 134
7-Benzyl-1-(2-cyclohexyl-ethyl-8-[1,4]diazepan-1-yl-3-methyl-3,7-dihydro-purine-2,6-dione

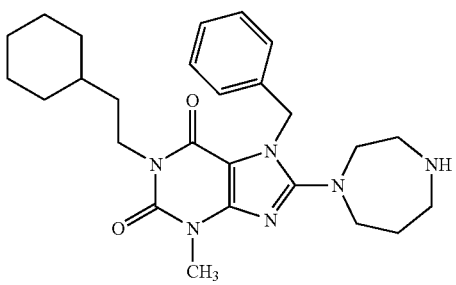

-continued

Example 135
7-Benzyl-8-[1,4]diazepan-1-yl-3-methyl-1-(5-methyl-hexyl)-3,7-dihydro-purine-2,6-dione

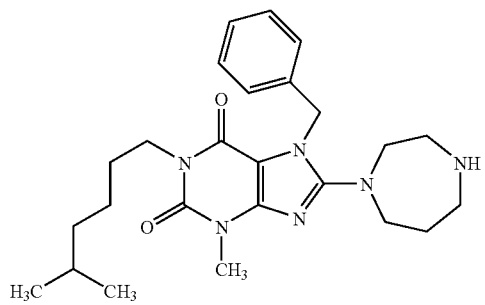

Example 136
7-Benzyl-8-[1,4]diazepan-1-yl-3-methyl-1-(3-methyl-butyl)-3,7-dihydro-purine-2,6-dione

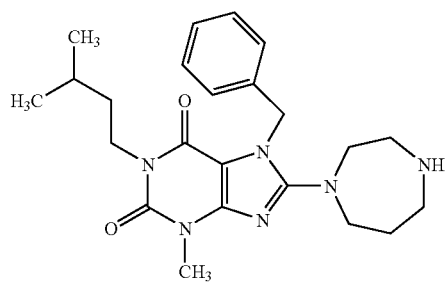

Example 137
7-Benzyl-8-[1,4]diazepan-1-yl-1-(2-ethoxy-ethyl)-3-methyl-3,7-dihydro-purine-2,6-dione

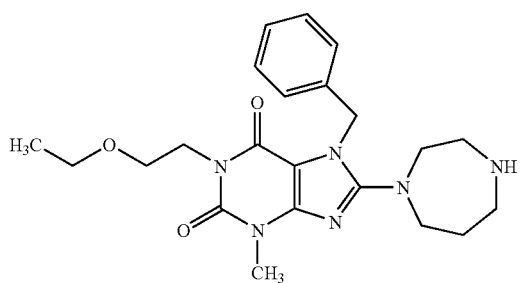

Example 138
8-[1,4]Diazepan-1-yl-7-(2-iodo-benzyl)-3-methyl-1-(tetrahydro-furan-2-ylmethyl)-3,7-dihydro-purine-2,6-dione

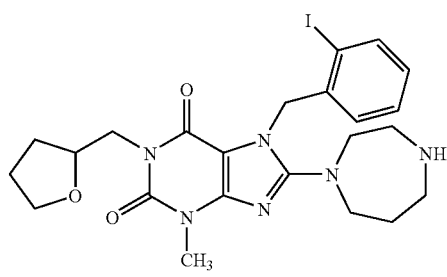

-continued

Example 139
7-(2-Iodo-benzyl)-3-methyl-8-piperazin-1-yl-1-(tetrahydro-furan-2-ylmethyl)-3,7-dihydro-purine-2,6-dione

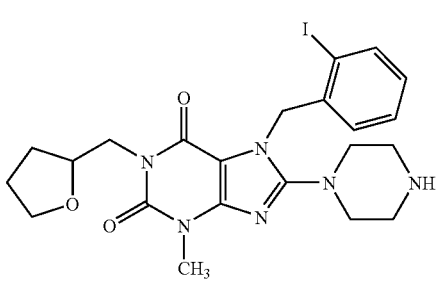

Example 140
8-[1,4]Diazepan-1-yl-7-(2-iodo-benzyl)-3-methyl-1-(tetrahydro-pyran-2-ylmethyl)-3,7-dihydro-purine-2,6-dione

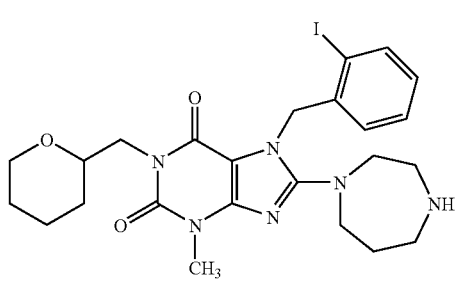

Example 141
7-(2-Iodo-benzyl)-3-methyl-8-piperazin-1-yl-1-(tetrahydro-pyran-2-ylmethyl)-3,7-dihydro-purine-2,6-dione

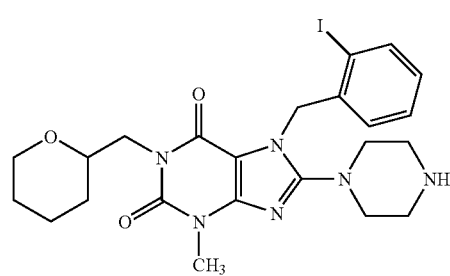

Example 142
7-(2-Iodo-benzyl)-3-methyl-1-(2-phenoxy-ethyl)-8-piperazin-1-yl-3,7-dihydro-purine-2,6-dione

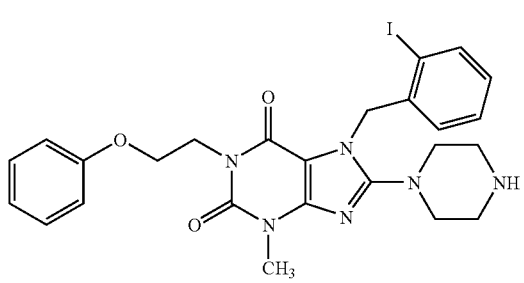

Example 143

8-[1,4]Diazepan-1-yl-7-(2-iodo-benzyl)-1-(2-methoxy-ethyl)-3-methyl-3,7-dihydro-purine-2,6-dione

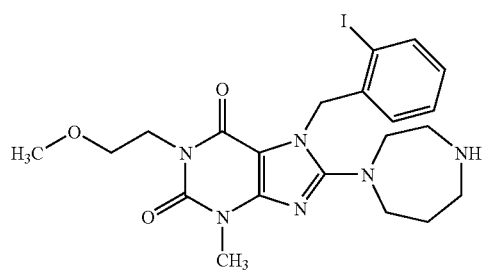

Example 144

7-(2-Iodo-benzyl)-1-(2-methoxy-ethyl)-3-methyl-8-piperazin-1-yl-3,7-dihydro-purine-2,6-dione

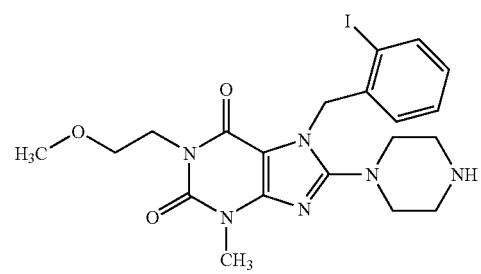

Example 145

1-(2-Benzyloxy-ethyl)-8-[1,4]diazepan-1-yl-7-(2-iodo-benzyl)-3-methyl-3,7-dihydro-purine-2,6-dione

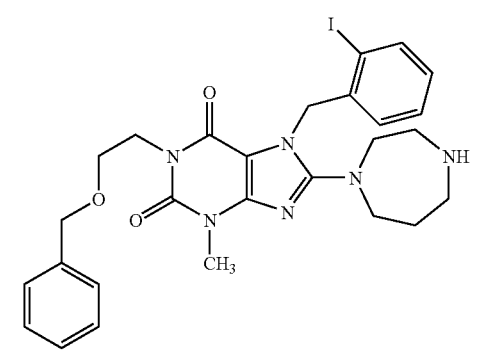

Example 146

1-(2-Benzyloxy-ethyl)-7-(2-iodo-benzyl)-3-methyl-8-piperazin-1-yl-3,7-dihydro-purine-2,6-dione

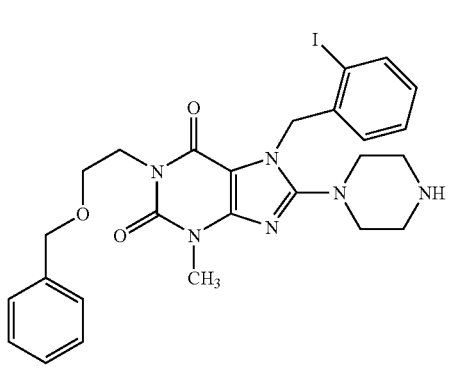

Example 147

1-(3,5-Dimethoxy-benzyl)-7-(2-iodo-benzyl)-3-methyl-8-piperazin-1-yl-3,7-dihydro-purine-2,6-dione

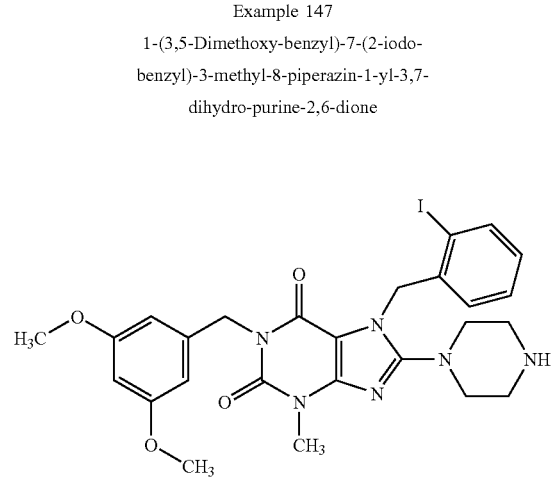

Example 148

7-(2-Iodo-benzyl)-1-(3-methoxy-benzyl)-3-methyl-8-piperazin-1-yl-3,7-dihydro-purine 2,6-dione

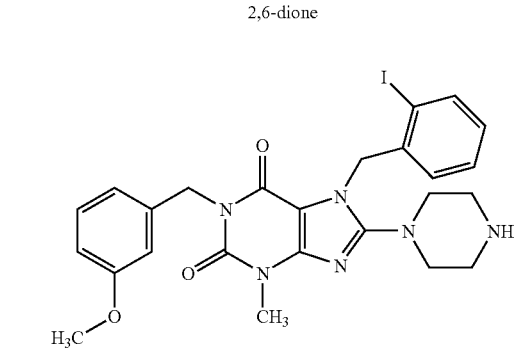

-continued

Example 149
8-[1,4]Diazepan-1-yl-7-(2-iodo-benzyl)-3-methyl-1-(3-trifluoromethoxy-benzyl)-3,7-dihydro-purine-2,6-dione

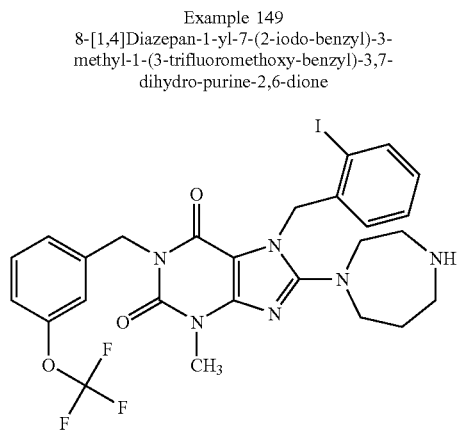

Example 150
7-(2-Iodo-benzyl)-3-methyl-8-piperazin-1-yl-1-(3-trifluoromethoxy-benzyl)-3,7-dihydro-purine-2,6-dione

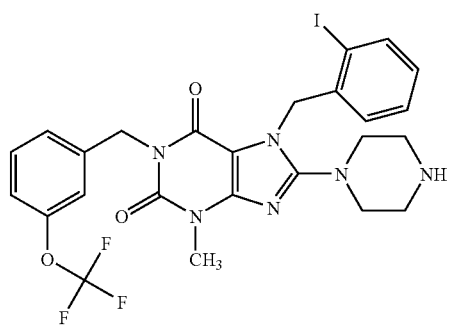

Example 151
8-[1,4]Diazepan-1-yl-1-(2-hydroxy-propyl)-7-(2-iodo-benzyl)-3-methyl-3,7-dihydro-purine-2,6-dione

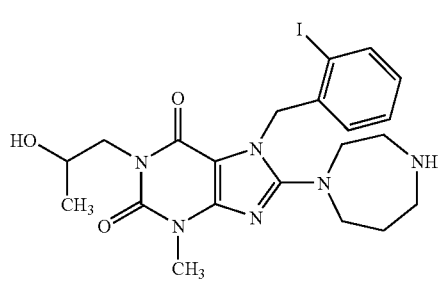

Example 152
8-[1,4]Diazepan-1-yl-1-(2,2-diethoxy-ethyl)-7-(2-iodo-benzyl)-3-methyl-3,7-dihydro-purine-2,6-dione

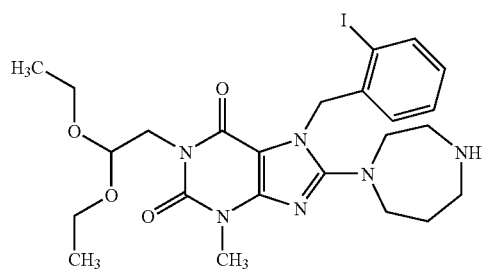

-continued

Example 153
8-[1,4]Diazepan-1-yl-1-(2,2-dimethoxy-ethyl)-7-(2-iodo-benzyl)-3-methyl-3,7-dihydro-purine-2,6-dione

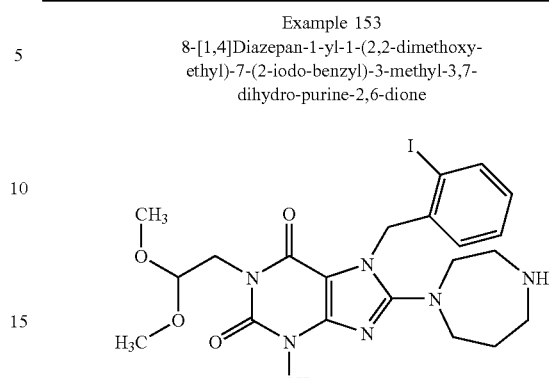

Example 154
8-[1,4]Diazepan-1-yl-1-(2-[1,3]dioxolan-2-yl-ethyl)-7-(2-iodo-benzyl)-3-methyl-3,7-dihydro-purine-2,6-dione

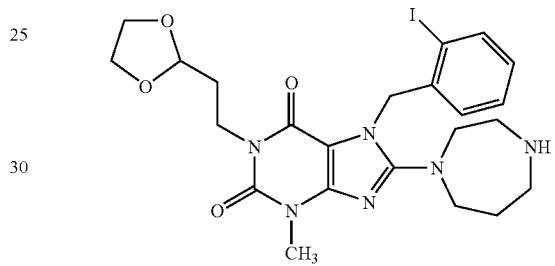

Example 155
1-(2-[1,3]Dioxolan-2-yl-ethyl)-7-(2-iodo-benzyl)-3-methyl-8-piperazin-1-yl-3,7-dihydro-purine-2,6-dione

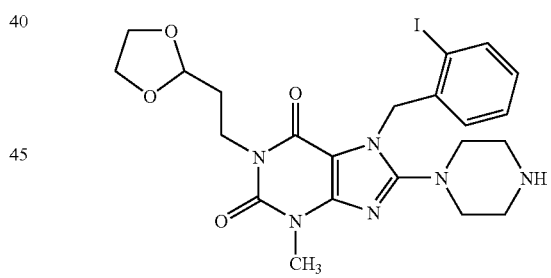

Example 156
1-[1,3]Dioxolan-2-ylmethyl-7-(2-iodo-benzyl)-3-methyl-8-piperazin-1-yl-3,7-dihydro-purine-2,6-dione

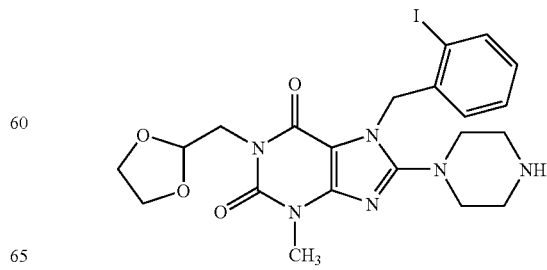

-continued

Example 157
8-[1,4]Diazepan-1-yl-1-(2-[1,3]dioxan-2-yl-
ethyl)-7-(2-iodo-benzyl)-3-methyl-3,7-
dihydro-purine-2,6-dione

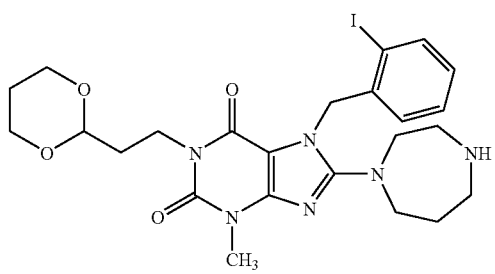

Example 158
1-(2-[1,3]Dioxan-2-yl-ethyl)-7-(2-iodo-
benzyl)-3-methyl-8-piperazin-1-yl-3,7-
dihydro-purine-2,6-dione

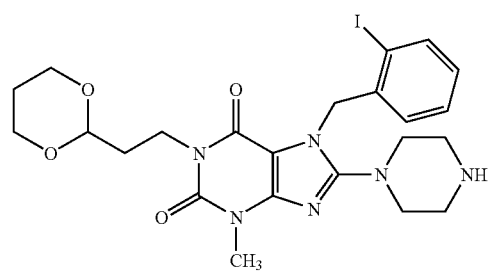

Example 159
8-[1,4]Diazepan-1-yl-1-(2,3-dihydroxy-
propyl)-7-(2-iodo-benzyl)-3-methyl-3,7-
dihydro-purine-2,6-dione

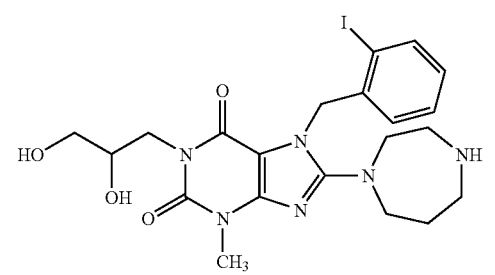

Example 160
1-(2,3-Dihydroxy-propyl)-7-(2-iodo-benzyl)-
3-methyl-8-piperazin-1-yl-3,7-dihydro-
purine-2,6-dione

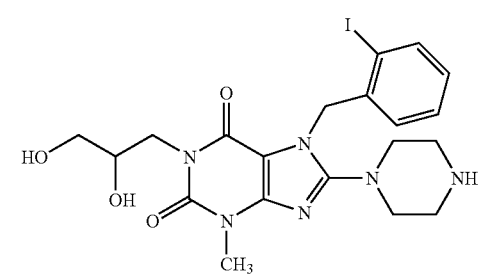

-continued

Example 161
8-[1,4]Diazepan-1-yl-1-(3-hydroxy-2-
methyl-propyl)-7-(2-iodo-benzyl)-3-methyl-
3,7-dihydro-purine-2,6-dione

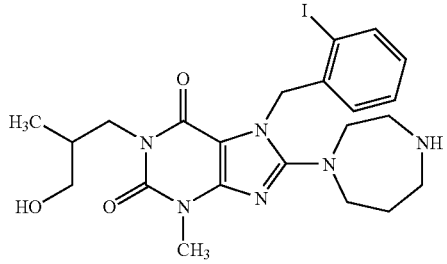

Example 162
1-(3-Hydroxy-2-methyl-propyl)-7-(2-iodo-
benzyl)-3-methyl-8-piperazin-1-yl-3,7-
dihydro-purine-2,6-dione

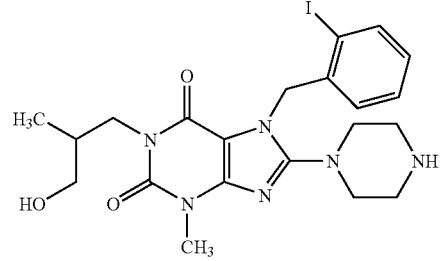

Example 163
8-[1,4]Diazepan-1-yl-7-(2-iodo-benzyl)-3-
methyl-1-[3-(tetrahydro-pyran-2-yloxy)-
propyl]-3,7-dihydro-purine-2,6-dione

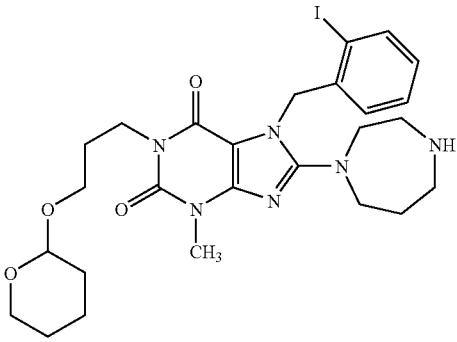

Example 164
8-[1,4]Diazepan-1-yl-1-(2-fluoro-ethyl)-7-(2-
iodo-benzyl)-3-methyl-3,7-dihydro-purine-
2,6-dione

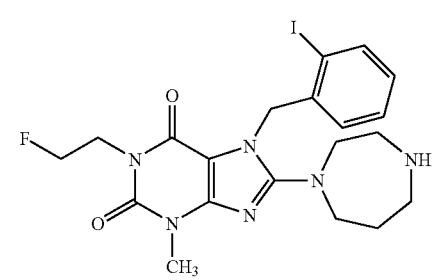

-continued

Example 165
7-Benzyl-8-[1,4]diazepan-1-yl-1-(3-hydroxy-propyl)-3-methyl-3,7-dihydro-purine-2,6-dione

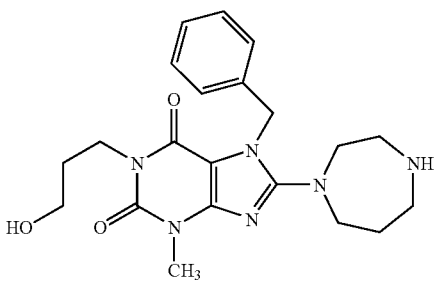

Example 166
7-Biphenyl-2-ylmethyl-8-[1,4]diazepan-1-yl-3-methyl-3,7-dihydro-purine-2,6-dione

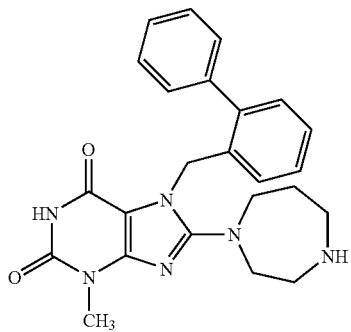

The invention claimed is:
1. A compound of formula I

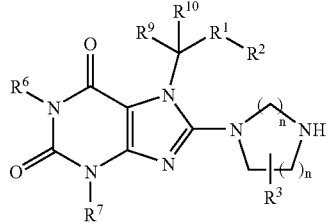

wherein
each n is one or two independently
$R^1$ is C=O; C=S; $C_1$–$C_2$ alkyl optionally substituted with one or more $R^4$ independently; $C_2$ alkenylene substituted with one or more $R^4$ independently; $C_2$ alkynylene; $C_3$–$C_7$ cycloalkylene optionally substituted with one or more $R^4$ independently; $C_3$–$C_7$ cycloheteroalkylene optionally substituted with one or more $R^4$ independently; arylene optionally substituted with one or more $R^4$ independently; arylene $C_1$–$C_3$ alkylene optionally substituted with one or more $R^4$ independently; heteroarylene optionally substituted with one or more $R^4$ independently; heteroarylene $C_1$–$C_3$ alkylene optionally substituted with one or more $R^4$ independently; perhalo $C_1$–$C_{10}$ alkylene; and, perhalo $C_1$–$C_{10}$ alkyloxyene;

$R^2$ is H; $C_1$ alkyl optionally substituted with one or more $R^4$ independently; $C_2$–$C_7$ alkenyl optionally substituted with one or more $R^4$ independently; $C_2$–$C_7$ alkynyl optionally substituted with one or more $R^4$ independently; $C_3$–$C_7$ cycloalkyl optionally substituted with one or more $R^4$ independently; $C_3$–$C_7$ cycloheteroalkyl optionally substituted with one or more $R^4$ independently; aryl optionally substituted with one or more $R^4$ independently; aryl $C_1$–$C_3$ alkyl optionally substituted with one or more $R^4$ independently, heteroaryl $C_1$–$C_3$ alkyl optionally substituted with one or more $R^4$ independently; heteroaryl optionally substituted with one or more $R^4$ independently, —SH; —SR$^5$; SOR$^5$; SO$_2$R$^5$; —CHO; —CH(OR$^5$)$_2$; carboxy; —CO$_2$R$^4$; NHCONNH$_2$; —NHCSNH$_2$; —NHCONH$_2$; —NHCOR$^4$; —NHSO$_2$R$^5$; —O—CO—(C$_1$–C$_5$) alkyl optionally substituted with one or more $R^4$ independently; cyano; nitro; halogen; hydroxy; perhalo $C_1$–$C_7$ alkyl; perhalo $C_1$–$C_7$ alkyloxy; —SO$_2$NH$_2$; —SO$_2$NH(R$^5$); —SO$_2$(R$^5$)$_2$; —CONH$_2$; —CSNH$_2$; —CON$_2$H$_3$; —CONH(R$^5$); —CON(R$^5$)$_2$; $C_1$–$C_{10}$ alkyloxy optionally substituted with $R^4$ independently; $C_2$–$C_{10}$ alkenyloxy optionally substituted with $R^4$; $C_2$–$C_{10}$ alkynyloxy optionally substituted with $R^4$ independently, aryloxy optionally substituted with $R^4$ independently; heteroaryloxy optionally substituted with $R^4$ independently;

$R^3$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$ alkynyl optionally substituted with one or more $R^4$ independently; $C_3$–$C_7$ cycloalkyl optionally substituted with one or more $R^4$ independently; $C_3$–$C_7$ cycloheteroalkyl optionally substituted with one or more $R^4$ independently; aryl optionally substituted with one or more $R^4$ independently; aryl $C_1$–$C_3$ alkyl optionally substituted with one or more $R^4$ independently; heteroaryl $C_1$–$C_3$ alkyl optionally substituted with one or more $R^4$ independently; heteroaryl optionally substituted with one or more $R^4$ independently; $C_1$–$C_{10}$ alkyl-NH(CH$_2$)$_{1-4}$NH-aryl optionally substituted with one or more $R^4$ independently; $C_1$–$C_{19}$ alkyl-NH(CH$_2$)$_{1-4}$NH-heteroaryl optionally substituted with one or more $R^4$ independently; $C_1$–$C_{10}$ alkyl-O(CH$_2$)$_{1-4}$NH-aryl optionally substituted with one or more $R^4$ independently; $C_1$–$C_{10}$ alkyl-O(CH$_2$)$_{1-4}$NH-heteroaryl optionally substituted with one or more $R^4$ independently; $C_1$–$C_{10}$ alkyl-O(CH$_2$)$_{1-4}$O-aryl optionally substituted with one or more $R^4$ independently; $C_1$–$C_{10}$ alkyl-O(CH$_2$)$_{1-4}$-heteroaryl optionally substituted with one or more $R^4$ independently; $C_1$–$C_{10}$ alkyl-S(CH$_2$)$_{1-4}$NH-aryl optionally substituted with one or more $R^4$ independently; $C_1$–$C_{10}$ alkyl-S(CH$_2$)$_{1-4}$NH-heteroaryl optionally substituted with one or more $R^4$ independently; $C_1$–$C_{10}$ alkyl-S(CH$_2$)$_{1-4}$S-aryl optionally substituted with one or more $R^4$ independently; $C_1$–$C_{10}$ alkyl-S(CH$_2$)$_{1-4}$S-heteroaryl optionally substituted with one or more $R^4$ independently; $C_1$–$C_{10}$ alkyl-O—$C_1$–$C_5$alkyl optionally substituted with one or more $R^4$; —NHCOR$^4$; —NHSO$_2$R$^5$; —O—SO—(C$_1$–C$_5$) alkyl optionally substituted with one or more $R^4$ independently; —SH; —SR$^5$; —SOR$^5$; —SO$_2$R$^5$; —CHO; —CH(OR$^5$)$_2$; carboxy; cyano; nitro; halogen; hydroxy; —SO$_2$NH$_2$; —SO$_2$NH(R$^5$); —SO$_2$N(R$^5$)$_2$; —CONH$_2$; —CONH(R$^5$); —CON(R$^5$)$_2$; —CSNH$_2$; —CONHNH$_2$; —CO$_2$R$^4$; —NHCNHNH$_2$; —NHCSNH$_2$; —NHCONH$_2$;

$R^4$ is $C_1$ alkyl optionally substituted with one or more $R^8$ independently; $C_2$–$C_{10}$alkenyl optionally substituted with one or more $R^8$ independently; $C_2$–$C_{10}$ alkynyl optionally substituted with one or more $R^8$ independently; $C_3$–$C_7$ cycloalkyl optionally substituted with one or more $R^8$ independently; $C_3$–$C_7$ cycloheteroalkyl optionally substituted with one or more $R^8$ independently; aryl optionally substituted with one or more $R^8$ independently; heteroaryl optionally substituted with one or more $R^8$ independently; amino; amino substituted with one or more $C_1$–$C_{10}$ alkyl optionally substituted with one or more $R^8$; amino substituted with one or two aryl optionally substituted with one or more $R^8$ independently; heteroaryl optionally substituted with one or more $R^8$ independently; =O; =S; —CO—$R^5$; —COO$R^5$; —O—CO—($C_1$–$C_5$) alkyl optionally substituted with one or more $R^8$ independently; NH(CH$_2$)$_{1-4}$NH-aryl; NH(CH$_2$)$_{1-4}$NH-heteroaryl; —NHCO$R^5$; —SO$R^5$; SO$_2$$R^5$; carboxy; cyano; N-hydroxyimino; nitro; halogen; hydroxy; perhalo $C_1$–$C_{10}$ alkyl; perhalo $C_1$–$C_{10}$ alkyloxy; —SH; —SR$^5$; —SO$_3$H; —SO$_3$R$^5$; —SO$_2$R$^5$; —SO$_2$NH$_2$; —SO$_2$NH(R$^5$); —SO$_2$N(R$^5$)$_2$; CONH$_2$; —CONH(R$^5$); —CON(R$^5$)$_2$; $C_1$–$C_{10}$ alkyloxy optionally substituted with one or more $R^8$ independently; $C_2$–$C_{10}$ alkenyloxy optionally substituted with one or more $R^8$ independently; $C_2$–$C_{10}$ alkynyloxy optionally substituted with one or more $R^8$ independently; aryloxy optionally substituted with one or more $R^8$ independently; heteroaryloxy optionally substituted with one or more $R^8$ independently;

and when two $R^4$ are attached to the same carbon atom, they together with the carbon atom, may form a spiroheterocyclic system selected from hydantoin; thiohydantoin; oxazolidine-2,5-dione;

$R^5$ is $C_1$–$C_{10}$ alkyl optionally substituted with one or more $R^8$ independently; $C_2$–$C_{10}$ alkenyl optionally substituted with one or more $R^8$ independently; $C_2$–$C_{10}$ alkynyl optionally substituted with one or more $R^8$ independently; $C_3$–$C_7$ cycloalkyl optionally substituted with one or more $R^8$ independently; $C_3$–$C_7$ cycloheteroalkyl optionally substituted with one or more $R^8$ independently; aryl optionally substituted with one or more $R^8$ independently; aryl $C_1$–$C_5$ alkyl optionally substituted with one or more $R^8$ independently; heteroaryl optionally substituted with one or more $R^8$ independently; heteroaryl $C_1$–$C_5$ alkyl optionally substituted with one or more $R^8$ independently;

$R^6$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$ alkynyl optionally substituted with one or more $R^4$ independently; $C_3$–$C_7$ cycloalkyl optionally substituted with one or more $R^4$ independently; $C_3$–$C_7$ cycloheteroalkyl optionally substituted with one or more $R^4$ independently; aryl optionally substituted with one or more $R^4$ independently; heteroaryl optionally substituted with one or more $R^4$ independently;

$R^7$ is H; $C_1$–$C_{10}$ alkyl optionally substituted with one or more $R^4$ independently; $C_2$–$C_{10}$ alkenyl optionally substituted with one or more $R^4$ independently; $C_2$–$C_{10}$alkynyl optionally substituted with one or more $R^4$ independently; $C_3$–$C_7$ cycloalkyl optionally substituted with one or more $R^4$ independently; $C_3$–$C_7$ cycloheteroalkyl optionally substituted with one or more $R^4$ independently; aryl optionally substituted with one or more $R^4$ independently; heteroaryl optionally substituted with one or more $R^4$ independently;

$R^8$ is H; nitro; tetrazole; pentafluorophenyl; —CH$_2$OH; —CHO; —C(OCH$_3$)$_2$; —COCH$_3$; —CF$_3$; —CCl$_3$; —OCF$_3$; —OCH$_3$; —CN; —CO$_2$H; —CO$_2$CH$_3$; —CONH$_2$; —CSNH$_2$; —CON$_2$H$_3$; —SO$_3$H; —SO$_2$NH$_2$; —SO$_2$NHCH$_3$; —SO$_2$N(CH$_3$)$_2$; —SO$_2$ (1-piperazinyl); —SO$_2$ (4-methylpiperazin-1-yl); —SO$_2$ (pyrrolidin-1-yl); —SO$_2$ (piperidin-1-yl); —SO$_2$ (morpholin-4-yl); N-hydroxyimino; —NH$_2$; —NHCH$_3$; —N(CH$_3$)$_2$; —NHCNHNH$_2$; —NHCNHNHCH$_3$; —NHCSNH$_2$; —NHCSNHCH$_3$; —NHCONH$_2$; —NHCONHCH$_3$; —NHCOCH$_3$; —NHSO$_2$CH$_3$; piperazinyl; morpholin-4-yl; thiomorpholin-4-yl; pyrrolidin-1-yl; piperidin-1-yl; halogen; —OH; —SH; —SCH$_3$; -aminoacetyl; —OPO$_3$H; —OPO$_2$OCH$_3$; —PO$_3$H$_2$; —PO(OCH$_3$)$_2$; PO(OH)(OCH$_3$);

$R^9$ is H; halogen; $C_1$–$C_{10}$ alkyl optionally substituted with one or more $R^4$ independently $R^{10}$ is H; halogen;

or, $R^9$ and $R^{10}$, together with the carbon atom to which they are attached, may be connected to form a cyclopropyl ring;

or a salt thereof with a pharmaceutically acceptable acid or base;

with the exception of the following compounds:

7-(3-Chloro-propyl)-1,3-dimethyl-8-piperazin-1-yl-3,7-dihydro-purine-2,6-dione;

7-(3-Amino-propyl)-1,3-dimethyl-8-piperazin-1-yl-3,7-dihydro-purine-2,6-dione;

3-(1,3-Dimethyl-2,6-dioxo-8-piperazin-1-yl-1,2,3,6-tetrahydro-purin-7-yl)-propionaldehyde;

1,3-dimethyl-7-(2-oxo-propyl)-8-piperazin-1-yl-3,7-dihydro-purine-2,6-dione, 1,3,1',3',7'-pentamethyl-8-piperazin-1-yl-3,7,3',7'-tetrahydro-7,8'-methanediyl-bis-purine-2,6-dione, 7-[2-Hydroxy-3-(4-methoxy-phenoxy)-propyl]-3-methyl-8-piperazin-1-yl-3,7-dihydro-purine-2,6-dione, 7-[2-hydroxy-2-(4-nitro-phenyl)-ethyl]-3-methyl-8-piperazin-1-yl-3,7,8,9-tetrahydro-purine-2,6-dione, 7-Benzyl-3-methyl-8-piperazin-1-yl-3,7-dihydro-purine-2,6-dione, 7-(4-Chloro-benzyl)-3-methyl-8-piperazin-1-yl-3,7-dihydro-purine-2,6-dione, 7-(2-Chloro-benzyl)-3-methyl-8-piperazin-1-yl-3,7-dihydro-purine-2,6-dione, 7-Ethyl-3-methyl-8-piperazin-1-yl-3,7-dihydro-purine-2,6-dione, 3-Methyl-8-piperazin-1-yl-1,7-dipropyl-3,7-dihydro-purine-2,6-dione, 3-Methyl-7-(3-methyl-butyl)-8-piperazin-1-yl-3,7-dihydro-purine-2,6-dione, 7-Butyl-3-methyl-8-piperazin-1-yl-3,1-dihydro-purine-2,6-dione, 3-Methyl-7-(3-phenyl-propyl)-8-piperazin-1-yl-3,7-dihydro-purine-2,6-dione, 7-But-2-enyl-3-methyl-8-piperazin-1-yl-3,7-dihydro-purine-2,6-dione, 7-(3-Chloro-but-2-enyl)-3-methyl-8-piperazin-1-yl-3,7-dihydro-purine-2,6-dione, 3-Methyl-7-(1-phenyl-ethyl)-8-piperazin-1-yl-3,7-dihydro-purine-2,6-dione, 3-Methyl-7-(3-methyl-benzyl)-8-piperazin-1-yl-3,7-dihydro-purine-2,6-dione, and 3-Methyl-7-propyl-8-piperazin-1-yl-3,7-dihydro-purine-2,6-dione.

2. A pharmaceutical composition comprising at least one compound according to claim 1 together with a pharmaceutically acceptable carrier or diluent.

3. A compound according to claim 1 selected from the following:
- 7-Benzyl-8-(6-hydroxymethyl-[1,4]diazepan-1-yl)-1,3-dimethyl-3,7-dihydropurine-2,6-dione,
- 7-Benzyl-8-(6-hydroxy-[1,4]diazepan-1-yl)-1,3-dimethyl-3,7-dihydropurine-2,6-dione,
- 7-Benzyl-8-(3-hydroxymethyl-[1,4]diezepan-1-yl)-1,3-dimethyl-3,7-dihydropurine-2,6-dione,
- 7-Benzyl-1,3-dimethyl-8-piperazin-1-yl-3,7-dihydropurine-2,6-dione,
- 1,3-Dimethyl-7-(4-methylbenzyl)-8-piperazin-1-yl-3,7-dihydropurine-2,6-dione,
- 3-(1,3-Dimethyl-2,6-dioxo-8-piperazin-1-yl-1,2,3,6-tetrahydropurin-7-ylmethyl) benzonitrile,
- 2-(1,3-Dimethyl-2,6-dioxo-8-piperazin-1-yl-1,2,3,6-tetrahydropurin-7-ylmethyl) benzonitrile,
- 1,3-Dimethyl-7-(1-phenylethyl)-8-piperazin-1-yl-3,7-dihydropurine-2,6-dione,
- 7-(2-Iodobenzyl)-1,3-dimethyl-8-piperazin-1-yl-3,7-dihydropurine-2,6-dione,
- 1,3-Dimethyl-8-piperazin-1-yl-7-(2-trifluoromethylbenzyl)-3,7-dihydropurine-2,6-dione,
- 1,3-Dimethyl-7-naphthaien-1-ylmethyl-8-piperazin-1-yl-3,7-dihydropurine-2,6-dione,
- 1,3-Dimethyl-7-naphthalen-2-ylmethyl-8-piperazin-1-yl-3,7-dihydropurine-2,6-dione,
- 7-(3-Bromobenzyl)-1,3-dimethyl-8-piperazin-1-yl-3,7-dihydropurine-2,6-dione,
- 7-Benzyl-8-(3-isopropylpiperazin-1-yl)-1,3-dimethyl-3,7-dihydropurine-2,6-dione,
- 7-Benzyl-8-[1,4]diazepan-1-yl-1,3-dimethyl-3,7-dihydro-purine-2,6-dione,
- 1,3-Dimethyl-7-(2-oxo-2-pyrrolidin-1-yl-ethyl)-8-piperazin-1-yl-3,7-dihydro-purine-2,6-dione,
- 2-(8-[1,4]Diazepan-1-yl-1,3-dimethyl-2,6-dioxo-1,2,3,6-tetrahydro-purin-7-ylmethyl) -benzonitrile,
- 8-[1,4]Diazepan-1-yl-7-(2-iodo-benzyl)-1,3-dimethyl-3,7-dihydro-purine-2,6-dione,
- 7-(2-Difluoromethoxy-benzyl)-1,3-dimethyl-8-piperazin-1-yl-3,7-dihydro-purine-2,6-dione,
- 7-(2,3-Dimethoxy-benzyl)-1,3-dimethyl-8-piperazin-1-yl-3,7-dihydro-purine-2,6-dione, and
- 1,3-Dimethyl-8-piperazin-1-yl-7-(2-trifluoromethoxy-benzyl)-3,7-dihydro-purine-2,6-dione.

4. A compound according to claim 1 selected from the following:
- 1,3-Dimethyl-8-piperazin-1-yl-7-(2-trifluoromethylsulfanyl-benzyl)-3,7-dihydro-purine-2,6-dione,
- 4-(1,3-Dimethyl-2,6-dioxo-8-piperazin-1-yl-1,2,3,6-tetrahydro-purin-7-yl)-butyronitrile,
- (R)-7-Benzyl-8-(3-isopropylpiperazin-1-yl)-1,3-dimethyl-3,7-dihydropurine-2,6-dione,
- (S)-7-Benzyl-8-(3-isopropylpiperazin-1-yl)-1,3-dimethyl-3,7-dihydropurine-2,6-dione,
- 7-Benzyl-8-(6,9-diazaspiro[4.5]dec-9-yl)-1,3-dimethyl-3,7-dihydropurine-2,6-dione,
- 7-Benzyl-8-(piperazin-3-spiro-3'-bicyclo[2,2,1]heptane-1-yl)-1,3-dimethyl-3,7-dihydropurine-2,6-dione,
- 8-[1,4]Diazepan-1-yl-7-(2-methoxy-benzyl)-1,3-dimethyl-3,7-dihydro-purine-2,6-dione,
- 8-[1,4]Diazepan-1-yl-1,3-dimethyl-7-nephthalen-1-ylmethyl-3,7-dihydro-purine-2,6-dione,
- 8-[1,4]Diazepan-1-yl-7-(2-fluoro-benzyl)-1,3-dimethyl-3,7-dihydro-purine-2,6-dione,
- 8-[1,4]Diazepan-1-yl-1,3-dimethyl-7-(2-methyl-benzyl)-3,7-dihydro-purine-2,6-dione,
- 7-(2-Chloro-benzyl)-8-[1,4]diazepan-1-yl-1,3-dimethyl-3,7-dihydro-purine-2,6-dione,
- 7-(2-Bromo-benzyl)-8-[1,4]diazepan-1-yl-1,3-dimethyl-3,7-dihydro-purine-2,6-dione,
- 8-[1,4]Diazepan-1-yl-1,3-dimethyl-7-(2-trifluoromethyl-benzyl)-3,7-dihydro-purine-2,6-dione,
- 8-[1,4]Diazepan-1-yl-1,3-dimethyl-7-(2-nitro-benzyl)-3,7-dihydro-purine-2,6-dione,
- 3-Benzyl-8-piperazin-1-yl-7-(2-trifluoromethyl-benzyl)-3,7-dihydro-purine-2,6-dione,
- 3,7-Dibenzyl-1-(2-hydroxy-ethyl)-8-piperazin-1-yl-3,7-dihydro-purine-2,6-dione,
- 3-Benzyl-7-phenethyl-8-piperazin-1-yl-3,7-dihydro-purine-2,6-dione,
- 3,7-Dibenzyl-8-[1,4]diazepan-1-yl-3,7-dihydro-purine-2,6-dione, and
- 7-Benzyl-8-[1,4]diazepan-1-yl-3-methyl-3,7-dihydro-purine-216-dione.

5. A compound according to claim 1 selected from the following:
- 3,7-Dibenzyl-8-[1,4]diazepan-1-yl-1-propyl-3,7-dihydro-purine-2,6-dione,
- 3,7-Dibenzyl-8-[1,4]diazepan-1-yl-1-(2-hydroxy-ethyl)-3,7-dihydro-purine-2,6-dione,
- 2-(3,7-Dibenzyl-8-[1,4]diazepan-1-yl-2,6-dioxo-2,3,6,7-tetrahydro-purin-1-yl)-N,N-diethyl-acetamide,
- 1,3,7-Tribenzyl-8-piperazin-1-yl-3,7-dihydro-purine-2,6-dione,
- 1,3,7-Tribenzyl-8-[1,4]diazepan-1-yl-3,7-dihydro-purine-2,6-dione,
- (S)-7-Benzyl-8-(3-benzyloxymethylpiperazin-1-yl)-1,3-dimethyl-3,7-dihydropurine-2,6-dione,
- 3,7-Dibenzyl-8-piperazin-1-yl-1-propyl-3,7-dihydro-purine-2,6-dione,
- 3,7-Dibenzyl-8-[1,4]diazepan-1-yl-1-propyl-3,7-dihydro-purine-2,6-dione,
- 3,7-Dibenzyl-8-piperazin-1-yl-3,7-dihydro-purine-2,6-dione,
- 3,7-Dibenzyl-8-[1,4]diazepan-1-yl-3,7-dihydro-purine-2,6-dione,
- 2-(3-Benzyl-2,6-dioxo-8-piperazin-1-yl-1-propyl-1,2,3,6-tetrahydro-purin-7-ylmethyl) -benzonitrile,
- 2-(3-Benzyl-8-[1,4]diazepan-1-yl-2,6-dioxo-1-propyl-1,2,3,6-tetrahydro-purin-7-ylmethyl)-benzonitrile,
- 2-(3-Benzyl-2,6-dioxo-8-piperazin-1-yl-1,2,3,6-tetrahydro-purin-7-ylmethyl)-benzonitrile,
- 2-(3-Benzyl-8-[1,4]diazepan-1-yl-2,6-dioxo-1,2,3,6-tetrahydro-purin-7-ylmethyl)-benzonitrile,
- 3-Benzyl-7-(2-iodo-benzyl)-8-piperazin-1-yl-1-propyl-3,7-dihydro-purine-2,6-dione,
- 3-Benzyl-8-[1,4]diazepan-1-yl-7-(2-iodo-benzyl)-1-propyl-3,7-dihydro-purine-2,6-dione,
- 3-Benzyl-7-(2-iodo-benzyl)-8-piperazin-1-yl-3,7-dihydro-purine-2,6-dione,
- 3-Benzyl-8-[1,4]diazepan-1-yl-7-(2-iodo-benzyl)-3,7-dihydro-purine-2,6-dione,
- 7-Benzyl-3-methyl-8-piperazin-1-yl-1-propyl-3,7-dihydro-purine-2,6-dione,
- 7-Benzyl-8-[1,4]diazepan-1-yl-3-methyl-1-propyl-3,7-dihydro-purine-2,6-dione, and
- 7-Benzyl-3-methyl-8-piperazin-1-yl-3,7-dihydro-purine-2,6-dione.

6. A compound according to claim 1 selected from the following:
- 7-Benzyl-8-[1,4]diazepan-1-yl-3-methyl-3,7-dihydro-purine-2,6-dione,
- 2-(3-Methyl-2,6-dioxo-8-piperazin-1-yl-1-propyl-1,2,3,6-tetrahydro-purin-7-ylmethyl) -benzonitrile,
- 2-(8-[1,4]Diazepan-1-yl-3-methyl-2,6-dioxo-1-propyl-1,2,3,6-tetrahydro-purin-7-ylmethyl)-benzonitrile,
- 2-(8-[1,4]Diazepan-1-yl-3-methyl-2,6-dioxo-1,2,3,6-tetrahydro-purin-7-ylmethyl) -benzonitrile,
- 7-(2-Iodo-benzyl)-3-methyl-8-piperazin-1-yl-1-propyl-3,7-dihydro-purine-2,6-dione,
- 8-[1,4]Diazepan-1-yl-7-(2-iodo-benzyl)-3-methyl-1-propyl-3,7-dihydro-purine-2,6-dione,
- 7-(2-Iodo-benzyl)-3-methyl-8-piperazin-1-yl-3,7-dihydro-purine-2,6-dione,
- 8-[1,4]Diazepan-1-yl-7-(2-iodo-benzyl)-3-methyl-3,7-dihydro-purine-2,6-dione,
- 3-Benzyl-8-[1,4]diazepan-1-yl-1-(3-hydroxy-propyl)-7-(2-iodo-benzyl)-3,7-dihydro-purine-2,6-dione,
- 3-Benzyl-8-[1,4]diazepan-1-yl-1-(2-ethoxy-ethyl)-7-(2-iodo-benzyl)-3,7-dihydro-purine-2,6-dione,
- 7-Benzyl-8-[1,4]diazepan-1-yl-3-methyl-1-(3-phenyl-allyl)-3,7-dihydro-purine-2,6-dione,
- 7-Benzyl-8-[1,4]diazepan-1-yl-3-methyl-1-(2-oxo-2-phenyl-ethyl)-3,7-dihydro-purine-2,6-dione,
- 2-(7-Benzyl-8-[1,4]diazepan-1-yl-3-methyl-2,6-dioxo-2,3,6,7-tetrahydro-purin-1-ylmethyl)-benzonitrile,
- (7-Benzyl-8-[1,4]diazepan-1-yl-3-methyl-2,6-dioxo-2,3,6,7-tetrahydro-purin-1-yl) -acetonitrile,
- 3-Methyl-7-(2-methyl-thiazol-4-ylmethyl)-8-piperazin-1-yl-3,7-dihydro-purine-2,6-dione,
- 8-[1,4]Diazepan-1-yl-3-methyl-7-(2-methyl-thiazol-4-ylmethyl)-3,7-dihydro-purine-2,6-dione,
- 3-Methyl-7-(2-oxo-2-phenyl-ethyl)-8-piperazin-1-yl-3,7-dihydro-purine-2,6-dione,
- 8-[1,4]Diazepan-1-yl-3-methyl-7-(2-oxo-2-phenyl-ethyl)-3,7-dihydro-purine-2,6-dione,
- 8-[1,4]Diazepan-1-yl-3-methyl-7-phenethyl-3,7-dihydro-purine-2,6-dione,
- 8-[1,4]Diazepan-1-yl-1-(3-hydroxy-propyl)-7-(2-iodo-benzyl)-3-methyl-3,7-dihydro-purine-2,6-dione, and
- 1-(3-Hydroxy-propyl)-7-(2-iodo-benzyl)-3-methyl-8-piperazin-1-yl-3,7-dihydro-purine-2,6-dione.

7. A compound according to claim 1 selected from the following:
- 8-[1,4]Diazepan-1-yl-1-(2-ethoxy-ethyl)-7-(2-iodo-benzyl)-3-methyl-3,7-dihydro-purine-2,6-dione,
- 1-(2-Ethoxy-ethyl)-7-(2-iodo-benzyl)-3-methyl-8-piperazin-1-yl-3,7-dihydro-purine-2,6-dione,
- 8-[1,4]Diazepan-1-yl-7-(2-iodo-benzyl)-3-methyl-1-(2-phenoxy-ethyl)-3,7-dihydro-purine-2,6-dione,
- 8-[1,4]Diazepan-1-yl-7-(2-iodo-benzyl)-1-[2-(2-methoxy-ethoxy)-ethyl]-3-methyl-3,7-dihydro-purine-2,6-dione,
- 7-(2-Iodo-benzyl)-1-[2-(2-methoxy-ethoxy)-ethyl]-3-methyl-8-piperazin-1-yl-3,7-dihydro-purine-2,6-dione,
- 8-[1,4]Diazepan-1-yl-1-(3,5-dimethoxy-benzyl)-7-(2-iodo-benzyl)-3-methyl-3,7-dihydro-purine-2,6-dione,
- 8-[1,4]Diazepan-1-yl-7-(2-iodo-benzyl)-1-(3-methoxy-benzyl)-3-methyl-3,7-dihydro-purine-2,6-dione,
- 7-Biphenyl-2-ylmethyl-8-[1,4]diazepan-1-yl-3-methyl-3,7-dihydro-purine-2,6-dione,
- 7-(2-Bromo-benzyl)-8-[1,4]diazepan-1-yl-3-methyl-3,7-dihydro-purine-2,6-dione,
- 7-(2-Chloro-benzyl)-8-[1,4]diazepan-1-yl-3-methyl-3,7-dihydro-purine-2,6-dione,
- 7-Benzyl-8-(3,5-dimethyl-piperazin-1-yl)-1,3-dimethyl-3,7-dihydro-purine-2,6-dione,
- 7-(4-Methoxybenzyl)-1,3-dimethyl-8-piperazin-1-yl-3,7-dihydropurine-2,6-dione,
- (1,3-Dimethyl-2,6-dioxo-8-piperazin-1-yl-1,2,3,6-tetrahydropurin-7-yl)-phenylacetic acid methyl ester,
- 7-(5-Chloro-2-nitrobenzyl)-1,3-dimethyl-8-piperazin-1-yl-3,7-dihydropurine-2,6-dione,
- 4-(1,3-Dimethyl-2,6-dioxo-8-piperazin-1-yl-1,2,3,6-tetrahydropurin-7-ylmethyl) benzonitrile,
- 7-(4-Methanesulfonylbenzyl)-1,3-dimethyl-8-piperazin-1-yl-3,7-dihydropurine-2,6-dione,
- 7-(2-Fluoro-6-nitrobenzyl)-1,3-dimethyl-8-piperazin-1-yl-3,7-dihydropurine-2,6-dione;
- 7-(4-Benzyloxybenzyl)-1,3-dimethyl-8-piperazin-1-yl-3,7-dihydropurine-2,6-dione,
- 7-(2,4-Dichlorobenzyl)-1,3-dimethyl-8-piperazin-1-yl-3,7-dihydropurine-2,6-dione,
- 1,3-Dimethyl-8-piperazin-1-yl-7-(4-trifluoromethylbenzyl)-3,7-dihydropurine-2,6-dione, and
- 7-Biphenyl-4-ylmethyl-1,3-dimethyl-8-piperazin-1-yl-3,7-dihydropurine-2,6-dione.

8. A compound according to claim 1 selected from the following:
- 3-(1,3-Dimethyl-2,6-dioxo-8-piperazin-1-yl-1,2,3,6-tetrahydropurin-7-ylmethyl) benzoic acid methyl ester,
- 4-(1,3-Dimethyl-2,6-dioxo-8-piperazin-1-yl-1,2,3,6-tetrahydropurin-7-ylmethyl) benzoic acid methyl ester,
- 7-Biphenyl-2-ylmethyl-1,3-dimethyl-8-piperazin-1-yl-3,7-dihydropurine-2,6-dione,
- 7-(4-tert-Butylbenzyl)-1,3-dimethyl-8-piperazin-1-yl-3,7-dihydropurine-2,6-dione,
- 1,3-Dimethyl-8-piperazin-1-yl-7-(4-trifluoromethoxybenzyl)-3,7-dihydropurine-2,6-dione,
- 7-(3,4-Dichlorobenzyl)-1,3-dimethyl-8-piperazin-1-yl-3,7-dihydropurine-2,6-dione,
- 1,3-Dimethyl-8-piperazin-1-yl-7-(4-[1,2,3]thiadiazol-4-ylbenzyl)-3,7-dihydropurine-2,6-dione,
- 4-(1,3-Dimethyl-2,6-dioxo-8-piperazin-1-yl-1,2,3,6-tetrahydropurin-7-ylmethyl)-3-methoxybenzoic acid methyl ester,
- 7-Cyclohexylmethyl-1,3-dimethyl-8-piperazin-1-yl-3,7-dihydro-purine-2,6-dione,
- 7-Benzyl-8-(2,5-diaza-bicyclo[2.2.1]hept-2-yl)-1,3-dimethyl-3,7-dihydro-purine-2,6-dione,
- 8-(6-Benzyl-[1,4]diazepan-1-yl)-7-(2-iodo-benzyl)-1,3-dimethyl-3,7-dihydro-purine-2,6-dione,
- (S)-7-Benzyl-8-(3-hydroxymethylpiperazin-1-yl)-1,3-dimethyl-3,7-dihydropurine-2,6-dione,
- 8-[1,4]Diazepan-1-yl-1,3-dimethyl-7-(2-oxo-2-pyrrolidin-1-yl-ethyl)-3,7-dihydro-purine-2,6-dione,
- 7-(2-Iodo-benzyl)-1,3-dimethyl-8-(6-pyridin-2-ylmethyl-[1,4]diazepan-1-yl)-3,7-dihydro-purine-2,6-dione,
- 7-(2-Bromo-benzyl)-1,3-dimethyl-8-(6-pyridin-2-ylmethyl-[1,4]diazepan-1-yl)-3,7-dihydro-purine-2,6-dione,
- (S) 7-Benzyl-8-(3-benzyl-piperazin-1-yl)-1,3-dimethyl-3,7-dihydro-purine-2,6-dione,
- 7-Benzyl-1,3-dimethyl-8-(3-phenethyl-piperazin-1-yl)-3,7-dihydro-purine-2,6-dione,
- (R)-7-Benzyl-8-(3-benzylpiperazin-1-yl)-1,3-dimethyl-3,7-dihydro-purine-2,6-dione,
- 7-Benzyl-8-(3-(2-hydroxy-benzyl)-piperazin-1-yl)-1,3-dimethyl-3,7-dihydro-purine-2,6-dione, and
- 7-Benzyl-8-(3-(2-methoxy-benzyl)-piperazin-1-yl) 1,3-dimethyl-3,7-dihydro-purine-2,6-dione.

9. A compound according to claim 1 selected from the following:
- (R) 7-Benzyl-8-(3-(4-methoxy-benzyl)-piperazin-1-yl)1,3-dimethyl-3,7-dihydro-purine-2,6-dione,
- (R)-7-Benzyl-8-(3-(4-hydroxy-benzyl)-piperazin-1-yl)-1,3-dimethyl-3,7-dihydro-purine-2.6-dione,
- (R)-7-Benzyl-1,3-dimethyl-8-(3-(4-nitro-benzyl)-piperazin-1-yl)-3,7-dihydro-purine-2,6-dione,
- (R)-7-Benzyl-8-(3-(4-fluoro-benzyl)-piperazin-1-yl)-1,3-dimethyl-3,7-dihydro-purine-2,6-dione,
- (R)-4-(4-(7-Benzyl-1,3-dimethyl-2,6-dioxo-2,3,6,7-tetrahydro-1H-purin-8-yl)-piperazin-2-ylmethyl)-benzonitrile,
- (R)-6-(8-(3-Benzyl-piperazin-1-yl)-1,3-dimethyl-2,6-dioxo-1,2,3,6-tetrahydro-purin-7-ylmethyl)-nicotinonitrile,
- (R)-7-Benzyl-1,3-dimethyl-8-(3-thiazol-4-ylmethyl-piperazin-1-yl)-3,7-dihydro-purine-2,6-dione,
- (R)-2-[1,3-Dimethyl-2,6-dioxo-8-(3-thiophen-2-ylmethyl-piperazin-1-yl)-1,2,3,6-tetrahydro-purin-7-ylmethyl]-benzonitrile,
- 7-Benzyl-8-[1,4]diazepan-1-yl-3-methyl-1-(tetrahydrofuran-2-ylmethyl)-3,7-dihydro-purine-2,6-dione,
- 7-Benzyl-1-(2-cyclohexyl-ethyl)-8-[1,4]diazepan-1-yl-3-methyl-3,7-dihydro-purine-2,6-dione,
- 7-Benzyl-8-[1,4]diazepan-1-yl-3-methyl-1-(5-methylhexyl)-3,7-dihydro-purine-2,6-dione,
- 7-Benzyl-8-[1,4]diazepan-1-yl-3-methyl-1-(3-methyl-butyl)-3,7-dihydro-purine-2,6-dione,
- 7-Benzyl-8-[1,4]diazepan-1-yl-1-(2-ethoxy-ethyl)-3-methyl-3,7-dihydro-purine-2,6-dione,
- 8-[1,4]Diazepan-1-yl-7-(2-iodo-benzyl)-3-methyl-1-(tetrahydro-furan-2-ylmethyl)-3,7-dihydro-purine-2,6-dione,
- 7-(2-Iodo-benzyl)-3-methyl-8-piperazin-1-yl-1-(tetrahydro-furan-2-ylmethyl)-3,7-dihydro-purine-2,6-dione,
- 8-[1,4]Diazepan-1-yl-7-(2-iodo-benzyl)-3-methyl-1-(tetrahydro-pyran-2-ylmethyl)-3,7-dihydro-purine-2,6-dione,
- 7-(2-Iodo-benzyl)-3-methyl-8-piperazin-1-yl-1-(tetrahydro-pyran-2-ylmethyl)-3,7-dihydro -purine-2,6-dione,
- 7-(2-Iodo-benzyl)-3-methyl-1-(2-phenoxy-ethyl)-8-piperazin-1-yl-3,7-dihydro-purine-2,6-dione, and
- 8-[1,4]Diazepan-1-yl-7-(2-iodo-benzyl)-1-(2-methoxy-ethyl)-3-methyl-3,7-dihydro-purine-2,6-dione.

10. A compound according to claim 1 selected from the following:
- 7-(2-Iodo-benzyl)-1-(2-methoxy-ethyl)-3-methyl-8-piperazin-1-yl-3,7-dihydro-purine-2,6-dione,
- 1-(2-Benzyloxy-ethyl)-8-[1,4]diazepan-1-yl-7-(2-iodobenzyl)-3-methyl-3,7-dihydro-purine-2,6-dione,
- 1-(2-Benzyloxy-ethyl)-7-(2-iodo-benzyl)-3-methyl-8-piperazin-1-yl-3,7-dihydro-purine-2,6-dione,
- 1-(3,5-Dimethoxy-benzyl)-7-(2-iodo-benzyl)-3-methyl-8-piperazin-1-yl-3,7-dihydro-purine-2,6-dione,
- 7-(2-Iodo-benzyl)-1-(3-methoxy-benzyl)-3-methyl-8-piperazin-1-yl-3,7-dihydro-purine-2,6-dione,
- 8-[1,4]Diazepan-1-yl-7-(2-iodo-benzyl)-3-methyl-1-(3-trifluoromethoxy-benzyl)-3,7-dihydro-purine-2,6-dione,
- 7-(2-Iodo-benzyl)-3-methyl-8-piperazin-1-yl-1-(3-trifluoromethoxy-benzyl)-3,7-dihydro-purine-2,6-dione,
- 8-[1,4]Diazepan-1-yl-1-(2-hydroxy-propyl)-7-(2-iodobenzyl)-3-methyl-3,7-dihydro-purine-2,6-dione,
- 8-[1,4]Diazepan-1-yl-1-(2,2-diethoxy-ethyl)-7-(2-iodobenzyl)-3-methyl-3,7-dihydro-purine-2,6-dion,
- 8-[1,4]Diazepan-1-yl-1-(2,2-dimethoxy-ethyl)-7-(2-iodobenzyl)-3-methyl-3,7-dihydro-purine-2,6-dione,
- 8-[1,4]Diazepan-1-yl-1-(2-[1,3]dioxolan-2-yl-ethyl)-7-(2-iodo-benzyl)-3-methyl-3,7-dihydro-purine-2,6-dione,
- 1-(2-[1,3]Dioxolan-2-yl-ethyl)-7-(2-iodo-benzyl)-3-methyl-8-piperazin-1-yl-3,7-dihydro-purine-2,6-dione,
- 1-[1,3]Dioxolan-2-ylmethyl-7-(2-iodo-benzyl)-3-methyl-8-piperazin-1-yl-3,7-dihydro-purine-2,6-dione,
- 8-[1,4]Diazepan-1-yl-1-(2-[1,3]dioxan-2-yl-ethyl)-7-(2-iodo-benzyl)-3-methyl-3,7-dihydro-purine-2,6-dione,
- 1-(2-[1,3]Dioxan-2-yl-ethyl)-7-(2-iodo-benzyl)-3-methyl-8-piperazin-1-yl-3,7-dihydro-purine-2,6-dione,
- 8-[1,4]Diazepan-1-yl-1-(2,3-dihydroxy-propyl)-7-(2-iodo-benzyl)-3-methyl-3,7-dihydro-purine-2,6-dione,
- 1-(2,3-Dihydroxy-propyl)-7-(2-iodo-benzyl)-3-methyl-8-piperazin-1-yl-3,7-dihydro-purine-2,6-dione,
- 8-[1,4]Diazepan-1-yl-1-(3-hydroxy-2-methyl-propyl)-7-(2-iodo-benzyl)-3-methyl-3,7-dihydro-purine-2,6-dione,
- 1-(3-Hydroxy-2-methyl-propyl)-7-(2-iodo-benzyl)-3-methyl-8-piperazin-1-yl-3,7-dihydro-purine-2,6-dione,
- 8-[1,4]Diazepan-1-yl-7-(2-iodo-benzyl)-3-methyl-1-[3-(tetrahydro-pyran-2-yloxy)-propyl]-3,7-dihydro-purine-2,6-dione,
- 8-[1,4]Diazepan-1-yl-1-(2-fluoro-ethyl)-7-(2-iodo-benzyl)-3-methyl-3,7-dihydro-purine-2,6-dione,
- 7-Benzyl-8-[1,4]diazepan-1-yl-1-(3-hydroxy-propyl)-3-methyl-3,7-dihydro-purine-2,6-dione, and
- 7-Biphenyl-2-ylmethyl-8-[1,4]diazepan-1-yl-3-methyl-3,7-dihydro-purine-2,6-dione.

* * * * *